US010988501B2

(12) United States Patent
Li et al.

(10) Patent No.: US 10,988,501 B2
(45) Date of Patent: Apr. 27, 2021

(54) REVERSIBLY BLOCKED NUCLEOSIDE ANALOGUES AND THEIR USE

(71) Applicants: Complete Genomics, Inc., San Jose, CA (US); BGI Shenzhen, Shenzhen (CN)

(72) Inventors: Handong Li, San Jose, CA (US); Snezana Drmanac, Los Altos Hills, CA (US); Radoje Drmanac, Los Altos Hills, CA (US); Xun Xu, Sunnyvale, CA (US); Lingling Peng, San Jose, CA (US); Scott Gablenz, San Jose, CA (US)

(73) Assignees: MGI Tech Co., Ltd.; BGI Shenzhen

( * ) Notice: Subject to any disclaimer, the term of this patent is extended or adjusted under 35 U.S.C. 154(b) by 177 days.

(21) Appl. No.: 16/094,845

(22) PCT Filed: Apr. 21, 2017

(86) PCT No.: PCT/US2017/028930
§ 371 (c)(1),
(2) Date: Oct. 18, 2018

(87) PCT Pub. No.: WO2017/185026
PCT Pub. Date: Oct. 26, 2017

(65) Prior Publication Data
US 2019/0144482 A1 May 16, 2019

Related U.S. Application Data

(60) Provisional application No. 62/326,620, filed on Apr. 22, 2016, provisional application No. 62/471,547, filed on Mar. 15, 2017.

(51) Int. Cl.
| | | |
|---|---|---|
| *C07H 19/10* | (2006.01) | |
| *C07H 19/20* | (2006.01) | |
| *C07H 15/04* | (2006.01) | |
| *C12Q 1/6869* | (2018.01) | |
| *C07H 21/04* | (2006.01) | |

(52) U.S. Cl.
CPC ............ *C07H 15/04* (2013.01); *C07H 19/10* (2013.01); *C07H 19/20* (2013.01); *C07H 21/04* (2013.01); *C12Q 1/6869* (2013.01)

(58) Field of Classification Search
None
See application file for complete search history.

(56) References Cited

U.S. PATENT DOCUMENTS

| | | | | |
|---|---|---|---|---|
| 5,543,507 A | * | 8/1996 | Cook | ............ C07H 21/00 435/91.1 |
| 7,816,503 B2 | * | 10/2010 | Milton | ............ C12Q 1/686 536/23.1 |
| 2016/0139133 A1 | * | 5/2016 | O'Halloran | ............ C07H 19/10 536/26.26 |
| 2017/0240961 A1 | * | 8/2017 | Drmanac | ............ C12Q 1/6876 |

FOREIGN PATENT DOCUMENTS

| | | | |
|---|---|---|---|
| WO | 2004/018497 A2 | 3/2004 | |
| WO | 2007/053719 A2 | 5/2007 | |
| WO | 2010/110775 A1 | 9/2010 | |
| WO | 2013/044018 A1 | 3/2013 | |
| WO | WO2016/164762 | * 10/2016 | ............ C07K 14/705 |

OTHER PUBLICATIONS

Misiura et al., "Synthesis of Nucleoside r-Thiotriphosphates via an Oxathiaphospholane Approach" Organic Letters vol. 7 No. 11 pp. 2217-2220 (Year: 2005).*
Keller et al., "Synthesis of 3'-O-Cyanoethyl-2'-Deoxythymidine-5'-Monophosphate and Its Use for the Sequencing-by-Synthesis Technology" Collection Symposium Series vol. 10 pp. 376-377 (Year: 2008).*
International Preliminary Report on Patentability received in International Application No. PCT/US2017/028930, dated Nov. 1, 2018; 9 pages.
Bi, L. et al., Design and Synthesis of a Chemically Cleavable Fluorescent Nucleotide, 3'-O-Allyl-dGTP-allyl-Bodipy-FL-510, as a Reversible Terminator for DNA Sequencing by Synthesis, Journal of the American Chemical Society, vol. 128, No. 8. Published Mar. 2006. pp. 2542-2543.
CAS RN 1288999-26-7, STN Entry Date May 2, 2011.
CAS RN 1288999-24-5, STN Entry Date May 2, 2011.
CAS RN 1288998-62-8, STN Entry Date May 2, 2011.
CAS RN 1288998-56-0, STN Entry Date May 2, 2011.
International Search Report and Written Opinion received in International Application No. PCT/US2017/028930, dated Jul. 20, 2017. 15 pages.
Knapp, D. C. et al., Fluoride-Cleavable, Fluorescently Labeled Reversible Terminators:Synthesis and Use in Primer Extension, Chemistry—A European Journal, vol. 17, No. 10. Published Mar. 2011. pp. 2903-2915.
Knapp, D. C. et al., Fluorescent labeling of (Oligo)nucleotides by a new fluoride cleavable linker capable of versatile attachment modes, Bioconjugate Chemistry, vol. 21, No. 6. Published Jun. 2010. pp. 1043-1055.
Wicke, L. et al. Postsynthetic on Column RNA Labeling via Stille Coupling. Bioconjugate Chemistry, vol. 23, No. 3. Published Mar. 2012. pp. 627-642.

* cited by examiner

*Primary Examiner* — Eric Olson
(74) *Attorney, Agent, or Firm* — Kilpatrick Townsend & Stockton LLP

(57) ABSTRACT

Reversibly blocked nucleoside analogues and methods of using such nucleoside analogues for sequencing of nucleic acids are provided.

18 Claims, 3 Drawing Sheets

| Row Labels | Average of Percent BIC | Average of Fit Score | Average of Mean signal TxR | Average of Mean signal FITC | Average of Mean signal Cy5 | Average of Mean signal Cy3 | Average of Mean Rho C | Average of Mean Rho T | Average of Mean Rho A | Average of Mean Rho G | Average of Mean Local Bgnd. TxrD | Average of Mean Local Bgnd. Fitc | Average of Mean Local Bgnd. Cy5 | Average of Mean Local Bgnd. Cy3 | Sum of Registration Status | Lane Condition |
|---|---|---|---|---|---|---|---|---|---|---|---|---|---|---|---|---|
| 1 | 23.1433 | 0.21863 | 4419.803 | 6780.877 | 4596.43 | 5042.498 | 2701.999 | 1243.67 | 1480.09 | 1238.37 | 2584 | 3018.961 | 2717.56 | 2751.58 | 1059 | Control Scan |
| 1 | 92.96 | 0.87 | 8901.00 | 15910.82 | 9083.36 | 10151.83 | 10786.67 | 4971.76 | 5874.50 | 4873.24 | 3378.23 | 3875.69 | 3632.86 | 3376.33 | 530.00 | Control |
| 2 | 0.00 | 0.00 | 2891.65 | 3716.15 | 3107.48 | 3328.18 | 0.00 | 0.00 | 0.00 | 0.00 | 2299.70 | 2735.63 | 2438.23 | 2547.65 | 0.00 | Allenyl dTTP Fresh |
| 3 | 0.00 | 0.00 | 2829.48 | 3716.04 | 3029.19 | 3322.02 | 0.00 | 0.00 | 0.00 | 0.00 | 2272.61 | 2741.99 | 2388.72 | 2549.76 | 0.00 | Allenyl dTTP Room Temp |
| 4 | 0.00 | 0.00 | 2863.88 | 3734.19 | 3040.61 | 3334.22 | 0.00 | 0.00 | 0.00 | 0.00 | 2297.09 | 2745.40 | 2393.76 | 2558.17 | 0.00 | Allenyl dTTP 65C |
| 5 | 0.00 | 0.00 | 2868.46 | 3736.33 | 3082.46 | 3313.95 | 0.00 | 0.00 | 0.00 | 0.00 | 2294.71 | 2745.68 | 2422.04 | 2540.21 | 0.00 | Cyanoethenyl-dTTP Fresh |
| 6 | 0.00 | 0.00 | 3033.43 | 3715.02 | 3088.22 | 3319.66 | 0.00 | 0.00 | 0.00 | 0.00 | 2342.75 | 2725.15 | 2421.40 | 2544.51 | 0.00 | Cyanoethenyl-dTTP Room Temp |
| 7 | 0.00 | 0.00 | 2937.56 | 3747.99 | 3113.53 | 3321.38 | 0.00 | 0.00 | 0.00 | 0.00 | 2332.05 | 2743.48 | 2435.69 | 2540.56 | 0.00 | Cyanoethenyl-dTTP 65C |
| 8 | 92.19 | 0.88 | 9032.96 | 15970.48 | 9226.59 | 10248.73 | 10829.32 | 4977.56 | 5966.20 | 5033.73 | 3454.71 | 3638.67 | 3607.80 | 3355.42 | 529.00 | Control |
| 2 | 23.0955 | 0.21615 | 4441.666 | 6691.734 | 4685.86 | 4855.715 | 2595.915 | 1207.21 | 1428.97 | 1227.41 | 2826.33 | 2984.961 | 2784.84 | 2744.71 | 1059 | After hot chase |
| 1 | 92.88 | 0.87 | 8896.14 | 15473.52 | 9098.29 | 9892.74 | 10369.26 | 4924.34 | 5727.10 | 4910.50 | 3415.17 | 3838.61 | 3659.38 | 3329.67 | 530.00 | Control |
| 2 | 0.00 | 0.00 | 3007.42 | 3642.41 | 3219.38 | 3308.75 | 0.00 | 0.00 | 0.00 | 0.00 | 2360.88 | 2697.82 | 2500.34 | 2553.12 | 0.00 | Allenyl dTTP Fresh |
| 3 | 0.00 | 0.00 | 2949.10 | 3855.75 | 3210.08 | 3301.94 | 0.00 | 0.00 | 0.00 | 0.00 | 2349.77 | 2716.71 | 2504.75 | 2552.69 | 0.00 | Allenyl dTTP Room Temp |
| 4 | 0.00 | 0.00 | 2928.77 | 3624.94 | 3205.27 | 3302.74 | 0.00 | 0.00 | 0.00 | 0.00 | 2335.16 | 2680.71 | 2503.06 | 2558.94 | 0.00 | Allenyl dTTP 65C |
| 5 | 0.00 | 0.00 | 2957.49 | 3640.86 | 3188.97 | 3271.50 | 0.00 | 0.00 | 0.00 | 0.00 | 2348.50 | 2687.02 | 2479.68 | 2522.39 | 0.00 | Cyanoethenyl-dTTP Fresh |
| 6 | 0.00 | 0.00 | 2979.92 | 3684.04 | 3200.65 | 3305.25 | 0.00 | 0.00 | 0.00 | 0.00 | 2349.06 | 2706.94 | 2480.05 | 2540.91 | 0.00 | Cyanoethenyl-dTTP Room Temp |
| 7 | 0.00 | 0.00 | 2975.58 | 3697.34 | 3217.72 | 3316.09 | 0.00 | 0.00 | 0.00 | 0.00 | 2344.80 | 2709.44 | 2469.39 | 2542.88 | 0.00 | Cyanoethenyl-dTTP 65C |
| 8 | 91.89 | 0.86 | 8838.92 | 15395.02 | 9146.49 | 9946.71 | 10298.07 | 4733.30 | 5704.69 | 4908.74 | 3487.33 | 3842.43 | 3662.09 | 3357.04 | 529.00 | Control |
| Grand Total | 23.1194 | 0.21739 | 4430.735 | 6691.305 | 4641.14 | 4899.106 | 2643.957 | 1225.44 | 1454.53 | 1232.89 | 2605.17 | 3001.961 | 2751.2 | 2748.14 | 2118 | |

Figure 1

| P(100 mM) | pH | Buffer | Salt (M) | Temp. (°C) | Time (min) | Cleavage % |
|---|---|---|---|---|---|---|
| THPP | 9.49 | 1M K₂HPO₄ | 1M KCl | 55 | 2 | 77 |
| THPP | 9.27 | 1M K4PPi | 1M KCl | 55 | 2 | 95 |
| 200 mM TCEP | 7.01 | 1M K₂HPO₄ | 1M KCl | 55 | 2 | 12 |
| 200 mM TCEP | 9.15 | 1M K₂HPO₄ | 1M KCl | 55 | 2 | 22 |
| 200 mM THMP | 9.06 | 1M K₂HPO₄ | 1M KCl | 55 | 2 | 11 |

Figure 2

| THPP(mM) | pH | New (1 M) | Salt (M) | Tris (mM) | Tween 20 | Temp. (°C) | Time (min) | Cleavage % |
|---|---|---|---|---|---|---|---|---|
| 200 | 9.04 | K₂HPO₄ | 0 | 0 | 0.10% | 60 | 2 | 85 |
| 200 | 9.85 | K₂HPO₄ | 0 | 200 | 0.10% | 60 | 2 | 82 |
| 200 | 8.97 | K₂HPO₄ | 1M NaCl | 0 | 0.10% | 60 | 2 | 87 |
| 200 | 9.04 | K₂HPO₄ | 1M KF | 0 | 0.10% | 60 | 2 | 93 |
| 200 | 9.04 | K₂HPO₄ | 1M CsF | 0 | 0.10% | 60 | 2 | 101 |

Figure 3

| THPP(mM) | pH | KF (M) | NaCl (M) | Tris (mM) | glycerol | Tween 20 | Temp. (°C) | Time (min) | Cleavage % |
|---|---|---|---|---|---|---|---|---|---|
| 20 | 9 | 1.5 | 0 | 200 | 5% | 0.10% | 55 | 10 | 46 |
| 40 | 9 | 1.5 | 0 | 200 | 5% | 0.10% | 55 | 10 | 64 |
| 60 | 9 | 1.5 | 0 | 200 | 5% | 0.10% | 55 | 10 | 77 |
| 80 | 9 | 1.5 | 0 | 200 | 5% | 0.10% | 55 | 10 | 84 |
| 100 | 9 | 1.5 | 0 | 200 | 5% | 0.10% | 55 | 10 | 89 |

Figure 4

| THPP(mM) | pH | KF (M) | NaCl (M) | Tris (mM) | glycerol | Tween 20 | Temp. (°C) | Time (min) | Cleavage % |
|---|---|---|---|---|---|---|---|---|---|
| 100 | 9 | 1.5 | 0 | 200 | 5% | 0.10% | 55 | 2 | 44 |
| 100 | 9 | 1.5 | 0 | 200 | 5% | 0.10% | 55 | 4 | 62 |
| 100 | 9 | 1.5 | 0 | 200 | 5% | 0.10% | 55 | 6 | 74 |
| 100 | 9 | 1.5 | 0 | 200 | 5% | 0.10% | 55 | 8 | 82 |
| 100 | 9 | 1.5 | 0 | 200 | 5% | 0.10% | 55 | 10 | 89 |

Figure 5

| THPP(mM) | pH | K₂HPO₄ (M) | CsF (M) | Tween 20 | Temp. (°C) | Time (min) | Cleavage % |
|---|---|---|---|---|---|---|---|
| 100 | 8.33 | 1 | 1 | 0.05% | 60 | 1min15s | 46 |
| 100 | 8.76 | 1 | 1 | 0.05% | 60 | 1min15s | 52 |
| 100 | 9.02 | 1 | 1 | 0.05% | 60 | 1min15s | 58 |
| 100 | 9.61 | 1 | 1 | 0.05% | 60 | 1min15s | 71 |
| 100 | 10.06 | 1 | 1 | 0.05% | 60 | 1min15s | 71 |

REVERSIBLY BLOCKED NUCLEOSIDE ANALOGUES AND THEIR USE

REFERENCE TO RELATED APPLICATIONS

This application claims the priority benefit of U.S. Provisional Application Nos. 62/326,620, filed Apr. 22, 2016, and 62/471,547, filed Mar. 15, 2017. The priority applications are incorporated herein in their entireties for all purposes.

BACKGROUND

The need for low cost, high-throughput, methods for nucleic acid sequencing and re-sequencing has led to the development of "massively parallel sequencing" (MPS) technologies. Improvements in such sequencing methods are of great value in science, medicine and agriculture.

BRIEF SUMMARY

The present invention relates to novel nucleoside analogues, and methods of their use for nucleic acid sequencing. In one aspect, the invention relates to nucleoside analogues having a reversible 3'-O blocking group and an affinity tag linked to the nucleobase through a linker.

In some embodiments, the present invention provides a nucleoside analogue of the following formula:

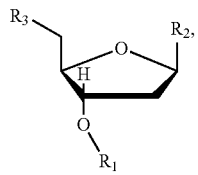

wherein
$R_1$ is a reversible blocking group selected from the group consisting of allenyl, cyanoethyl, cyanoethenyl, formaldehyde oximyl, acrylaldehyde oximyl, propionaldehyde oximyl, and cyanoethenaldehyde oximyl; $R_2$ comprises a nucleobase; and $R_3$ is a cleavable linking moiety comprising at least three (e.g., 3-10) phosphates, or analogues thereof.

In some cases, $R_3$ comprises a 5'-O-1-thio triphosphate. In some cases, the nucleoside has the formula of Formula VIII:

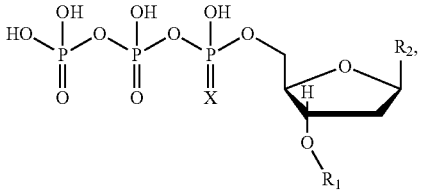

Formula VIII wherein
X is O or S and the nucleoside analogue is a substrate for a DNA polymerase. In some cases, $R_2$ consists of a nucleobase. In some cases, $R_2$ and/or $R_3$ is detectably labeled. In some cases, the nucleoside has the following formula:

wherein $R_2$ consists of the nucleobase; L is a linker; and D is a detectable fluorescent label.

In some cases, the nucleoside analogue has the following formula:

wherein
X is selected from the group consisting of O and S.

In some cases, the nucleoside analogue comprises the following formula:

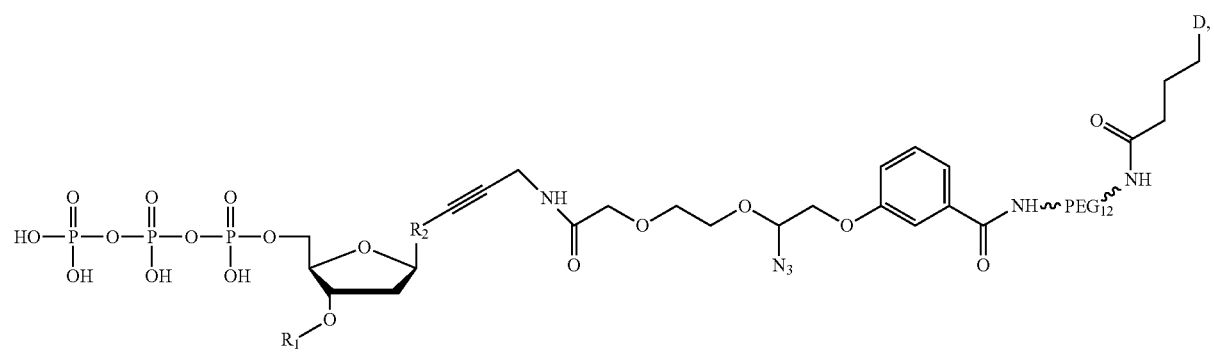

wherein R₂ is the nucleobase; R₁ is selected from the group consisting of allenyl, cyanoethyl, cyanoethenyl, formalde- In some cases, the nucleoside analogue comprises the following formula:

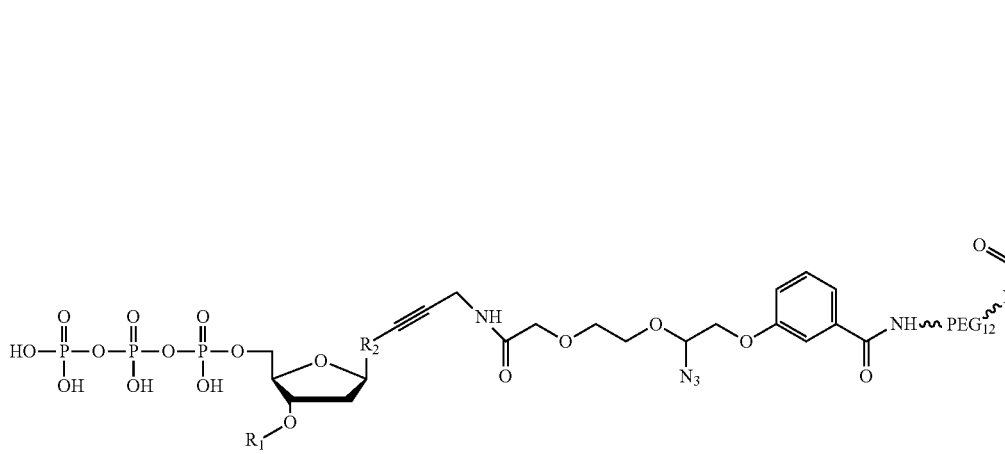

hyde oximyl, acrylaldehyde oximyl, propionaldehyde oximyl, and cyanoethenaldehyde oximyl; and D comprises a rhodamine dye (e.g., ROX) or a derivative thereof.

In some embodiments, the present invention provides a nucleoside analogue of Formula VI:

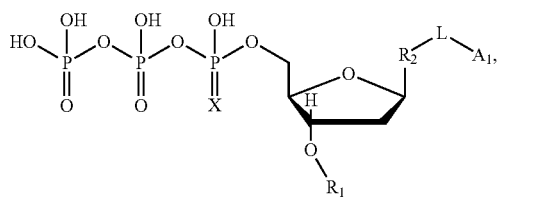

Formula VI wherein
R₁ is a reversible blocking group selected from the group consisting of allenyl, cyanoethyl, cyanoethenyl, formaldehyde oximyl, acrylaldehyde oximyl, propionaldehyde oximyl, and cyanoethenaldehyde oximyl; R₂ is a nucleobase; L is a linker; A₁ comprises an affinity tag; X is selected from the group consisting of O and S; and the nucleoside analogue is a substrate for a DNA polymerase.

In some cases, L is a cleavable linker. In some cases, R₁ and L can be cleaved from the nucleoside analogue under the same conditions. In some cases, A₁ comprises a nitrilotriacetic acid (NTA) affinity tag, or a peptide affinity tag comprising at least six contiguous histidine amino acids. In some cases, A₁ comprises an affinity tag selected from the group consisting of biotin, a small molecule antigen, and a peptide. In some cases, the small molecule antigen is selected from the group consisting of a fluorophore, an amphetamine, a barbituate, a benzodiazepine, a cocaine metabolite, a cannabinoid, a cannabinoid metabolite, tetrahydrocannabinol, methadone, an opiate, propoxyphene, phencyclidine, digoxigenin, and DNP. In some cases, the peptide is selected from the group consisting of a His tag, a Myc tag, a Flag tag, an HA tag, a V5 tag, an AviTag, a calmodulin tag, an E tag, an S tag, an SBP tag, a Softag, a Strep tag, a TC tag, a VSV tag, an Xpress tag, glutathione, an isopeptag, and a SpyTag.

wherein R₂ is a nucleobase and R₁ is selected from the group consisting of allenyl, cyanoethyl, cyanoethenyl, formaldehyde oximyl, acrylaldehyde oximyl, propionaldehyde oximyl, and cyanoethenaldehyde oximyl. In some cases, the nucleobase is selected from the group consisting of a 7-substituted 7-deaza adenine analogue, a 7 substituted 7-deaza guanine analogue, a 5-substituted thymine, and a 5-substituted cytosine.

In some embodiments, the present invention provides a composition comprising a nucleoside analogue of the following formula:

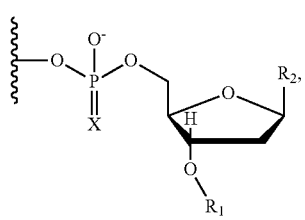

wherein
R₁ is a reversible blocking group selected from the group consisting of allenyl, cyanoethyl, cyanoethenyl, formaldehyde oximyl, acrylaldehyde oximyl, propionaldehyde oximyl, and cyanoethenaldehyde oximyl; X is selected from the group consisting of O and S; and R₂ comprises a nucleobase, and optionally a linker and a detectable label or affinity agent, wherein the nucleoside analogue is covalently linked via the 5' phosphate or thiophosphate to an oligonucleotide. In some cases, R₂ consists of a nucleobase. In some cases, R₂ comprises a nucleobase, a linker, and a detectable label or affinity agent.

In some embodiments, the present invention provides a composition comprising
i) a nucleoside analogue of the following formula:

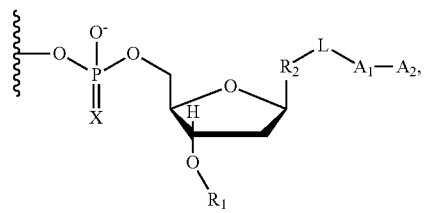

or
ii) a nucleoside analogue of Formula IX:

Formula IX

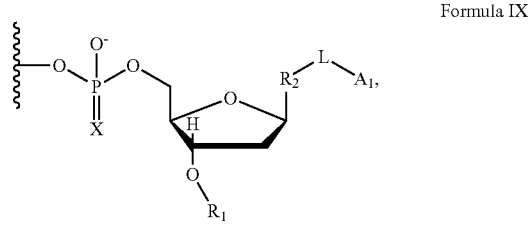

wherein $R_1$ is a reversible blocking group selected from the group consisting of allenyl, cyanoethyl, cyanoethenyl, formaldehyde oximyl, acrylaldehyde oximyl, propionaldehyde oximyl, and cyanoethenaldehyde oximyl; X is selected from the group consisting of O and S; $R_2$ is a nucleobase; L is a linker; $A_1$ comprises an affinity tag; and $A_2$ comprises a detectably labeled affinity agent that forms a specific and non-covalent complex with $A_1$, wherein the nucleoside analogue is covalently linked via the 5' phosphate or thiophosphate to an oligonucleotide. In some cases, $A_1$ comprises a fluorescent dye selected from the group consisting of a fluorone dye, a rhodamine dye, a cyanine dye, a coumarin dye, a phycoerythrin, and an allophycocyanine.

In some embodiments, the present invention provides a method of sequencing comprising: i) providing a reaction mixture comprising a template nucleic acid, a primer, a polymerase, and a first nucleoside analogue of Formula VI:

Formula VI

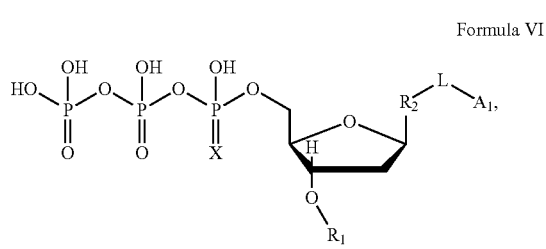

wherein $R_1$ is a reversible blocking group selected from the group consisting of allenyl, cyanoethyl, cyanoethenyl, formaldehyde oximyl, acrylaldehyde oximyl, propionaldehyde oximyl, and cyanoethenaldehyde oximyl; X is selected from the group consisting of O and S; $R_2$ is a nucleobase; L is a linker; and $A_1$ comprises an affinity tag; ii) extending the primer by incorporating the first nucleoside analogue with the polymerase; iii) contacting the incorporated first nucleoside analogue with a detectably labeled affinity agent that forms a specific and non-covalent complex with $A_1$ of the incorporated first nucleoside analogue, thereby specifically labeling the incorporated first nucleoside analogue; and iv) detecting the specifically labeled incorporated first nucleoside analogue.

In some cases, the detectably labeled affinity agent is fluorescently labeled, and the detection comprises detecting a fluorescence emission from the fluorescently labeled affinity agent in complex with $A_1$ of the incorporated first nucleoside analogue. In some cases, the method further comprises: v) cleaving the reversible blocking group $R_1$ of the incorporated first nucleoside analogue thereby removing the blocking group from the incorporated first nucleoside analogue; vi) cleaving the linker L thereby removing the affinity tag $A_1$ of the incorporated first nucleoside analogue, or quenching the label of the detectably labeled affinity agent in complex with $A_1$ of the incorporated first nucleoside analogue; vii) providing a second nucleoside analogue of Formula VI and a polymerase; viii) extending the primer by incorporating the second nucleoside analogue with the polymerase; ix) contacting the incorporated second nucleoside analogue with a detectably labeled affinity agent that forms a specific and non-covalent complex with $A_1$ of the incorporated second nucleoside analogue, thereby specifically labeling the incorporated second nucleoside analogue; and x) detecting the specifically labeled incorporated second nucleoside analogue.

In some embodiments, the present invention provides a method of sequencing comprising: i) providing a reaction mixture comprising template nucleic acid, a primer, a polymerase, and a first nucleoside analogue of Formula VII:

Formula VII

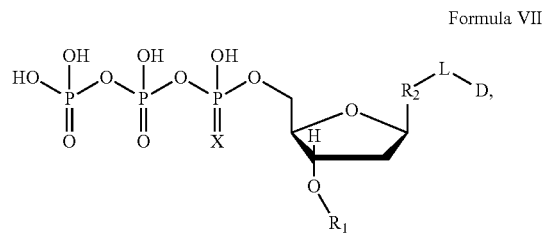

wherein $R_1$ is a reversible blocking group selected from the group consisting of allenyl, cyanoethyl, cyanoethenyl, formaldehyde oximyl, acrylaldehyde oximyl, propionaldehyde oximyl, and cyanoethenaldehyde oximyl; X is selected from the group consisting of O and S; and $R_2$ comprises a nucleobase; L is a linker; and D comprises a detectable fluorescent label; ii) extending the primer by incorporating the first nucleoside analogue with the polymerase; and iv) detecting the labeled incorporated first nucleoside analogue by detecting a fluorescence emission from the fluorescent label.

In some cases, the method further comprises: v) cleaving the reversible blocking group $R_1$ of the incorporated first nucleoside analogue thereby removing the blocking group from the incorporated first nucleoside analogue; vi) providing a second detectably labeled nucleoside analogue of Formula VII and a polymerase; vii) extending the primer by incorporating the second nucleoside analogue with the polymerase; and viii) detecting incorporation of the second nucleoside analogue by detecting a fluorescence emission from the labeled incorporated second nucleoside analogue.

In some embodiments, the present invention provides a method of sequencing comprising: i) providing a reaction mixture comprising a template nucleic acid, a primer, a polymerase, and a first nucleoside analogue of Formula VIII:

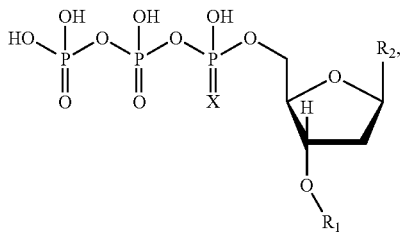

wherein $R_1$ is a reversible blocking group selected from the group consisting of allenyl, cyanoethyl, cyanoethenyl, formaldehyde oximyl, acrylaldehyde oximyl, propionaldehyde oximyl, and cyanoethenaldehyde oximyl; X is selected from the group consisting of O and S; and $R_2$ comprises or consists of a nucleobase; and ii) extending the primer by incorporating the first nucleoside analogue with the polymerase, thereby generating pyrophosphate; and iii) detecting incorporation of the first nucleoside analogue by detecting the pyrophosphate.

In some cases, the method further comprises: iv) cleaving the reversible blocking group $R_1$ of the incorporated first nucleoside analogue thereby removing the blocking group from the incorporated first nucleoside analogue; v) providing a second nucleoside analogue of Formula VIII and a polymerase; vi) extending the primer by incorporating the second nucleoside analogue with the polymerase, thereby generating pyrophosphate; and vii) detecting incorporation of the second nucleoside analogue by detecting the pyrophosphate.

In some embodiments, the present invention provides a method of sequencing comprising: i) providing a reaction mixture comprising a template nucleic acid, a primer, a ligase, and an oligonucleotide comprising a first nucleoside analogue of Formula IX:

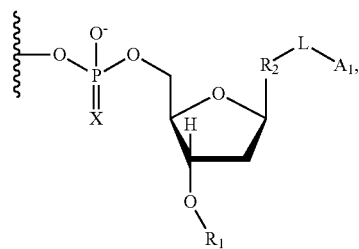

Formula IX wherein $R_1$ is a reversible blocking group selected from the group consisting of allenyl, cyanoethyl, cyanoethenyl, formaldehyde oximyl, acrylaldehyde oximyl, propionaldehyde oximyl, and cyanoethenaldehyde oximyl; X is selected from the group consisting of O and S; $R_2$ is a nucleobase; L is a linker; and $A_1$ comprises an affinity tag; ii) hybridizing the oligonucleotide comprising the first nucleoside analogue of Formula IX to the template nucleic acid at a position 3' of, and adjacent to, the primer; iii) cleaving the reversible blocking group $R_1$ of the hybridized oligonucleotide comprising the first nucleoside analogue of Formula IX; iv) ligating the hybridized oligonucleotide to the adjacent primer with the ligase, thereby incorporating the first nucleoside analogue of Formula IX into the primer; v) contacting the incorporated first nucleoside analogue with a detectably labeled affinity agent that forms a specific and non-covalent complex with A of the incorporated first nucleoside analogue, thereby specifically labeling the incorporated first nucleoside analogue; and vi) detecting the specifically labeled incorporated first nucleoside analogue.

In some cases, the detectably labeled affinity agent is fluorescently labeled, and the detection comprises detecting a fluorescence emission from the fluorescently labeled affinity agent in complex with A of the incorporated first nucleoside analogue. In some cases, the method further comprises: vii) cleaving the linker L thereby removing the affinity tag $A_1$ of the incorporated first nucleoside analogue, or quenching the label of the detectably labeled affinity agent in complex with $A_1$ of the incorporated first nucleoside analogue; viii) providing a second nucleoside analogue of Formula IX and a ligase; ix) hybridizing an oligonucleotide comprising a second nucleoside analogue of Formula IX to the template nucleic acid at a position 3' of, and adjacent to, the primer; x) ligating the hybridized oligonucleotide to the adjacent primer with the ligase, thereby incorporating the second nucleoside analogue of Formula IX into the primer; xi) contacting the incorporated second nucleoside analogue with a detectably labeled affinity agent that forms a specific and non-covalent complex with $A_1$ of the incorporated second nucleoside analogue, thereby specifically labeling the incorporated second nucleoside analogue; and xii) detecting the specifically labeled incorporated second nucleoside analogue.

In some embodiments, the present invention provides a method of sequencing comprising: i) providing a reaction mixture comprising a template nucleic acid, a primer, a ligase, and an oligonucleotide comprising a first nucleoside analogue of Formula X:

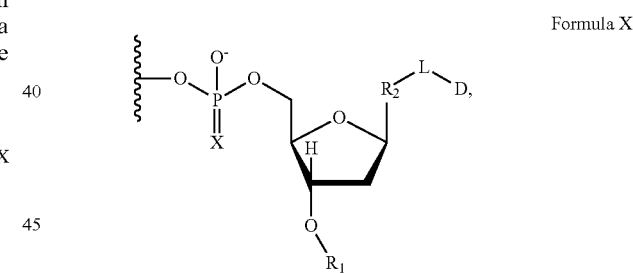

Formula X wherein $R_1$ is a reversible blocking group selected from the group consisting of allenyl, cyanoethyl, cyanoethenyl, formaldehyde oximyl, acrylaldehyde oximyl, propionaldehyde oximyl, and cyanoethenaldehyde oximyl; X is selected from the group consisting of O and S; $R_2$ is a nucleobase; L is a linker; and D comprises a fluorescent detectable label; ii) hybridizing the oligonucleotide comprising the first nucleoside analogue of Formula X to the template nucleic acid at a position 3' of, and adjacent to, the primer; iii) cleaving the reversible blocking group $R_1$ of the hybridized oligonucleotide comprising the first nucleoside analogue of Formula X; iv) ligating the hybridized oligonucleotide to the adjacent primer with the ligase, thereby incorporating the first nucleoside analogue of Formula X into the primer; and v) detecting the labeled incorporated first nucleoside analogue.

In some cases, the method further comprises: vi) cleaving the linker, thereby releasing the label of the labeled incorporated first nucleoside analogue; vii) providing a ligase, and a second oligonucleotide comprising a second nucleoside analogue of Formula X; viii) hybridizing the second oligonucleotide to the template nucleic acid at a position 3' of, and adjacent to, the primer; ix) cleaving the reversible blocking group $R_1$ of the hybridized second oligonucleotide; x) ligating the hybridized second oligonucleotide to the adjacent primer with the ligase, thereby incorporating the second nucleoside analogue of Formula X into the primer; and xi) detecting the labeled incorporated second nucleoside analogue.

BRIEF DESCRIPTION OF THE DRAWINGS

FIG. 1: shows polymerase-mediated incorporation of allenyl-dTTP and cyanoethenyl dTTP analogues during a sequencing by synthesis reaction. Both allenyl-dTTP and cyanoethyl-dTTP are as effective polymerase substrates for sequencing as the cold control, 3'-azidomethyl-dTTP.

FIG. 2: shows cleavage efficiency in the presence of buffers.

FIG. 3: shows cleavage efficiency in the presence of THPP with different buffer formulations.

FIG. 4: shows the effect of increasing a cleavage reagent concentration on cleavage efficiency.

FIG. 5: shows the effect of increasing the cleavage time on cleavage efficiency.

DETAILED DESCRIPTION

I. Overview

Figures 6, 7:
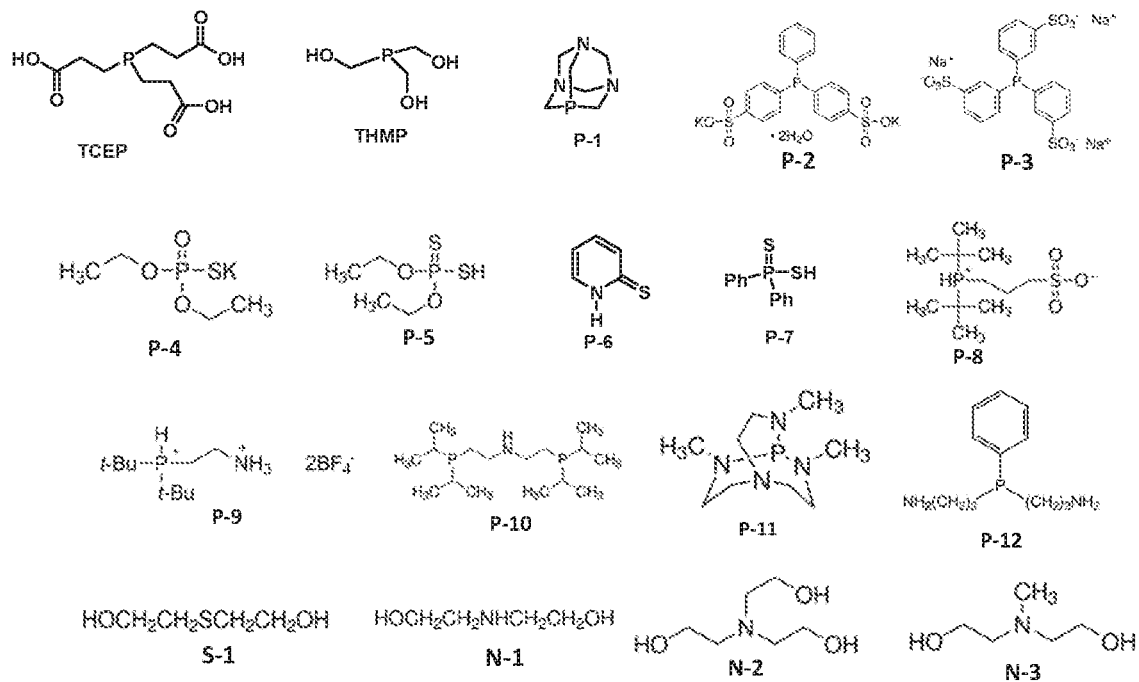
FIG. 6: shows the effect of increasing the cleavage pH on cleavage efficiency.
FIG. 7: shows structures of cleavage reagents tested.

In certain aspects, the present invention provides 3'-O reversibly blocked nucleoside analogues for nucleic acid sequencing, as well as polynucleotides containing such nucleoside analogues incorporated therein. Such nucleoside analogues can be incorporated by, e.g., polymerization, ligation, or chemical synthesis. In other aspects, the present invention provides methods of using such nucleoside analogues for nucleic acid sequencing. The 3'-O reversibly blocked nucleoside analogues can be used in any compatible sequencing by synthesis or sequencing by ligation method known in the art.

In one aspect, the nucleoside analogue includes a detectable label (e.g., fluorophore). In some embodiments, the detectable label can be attached to the 3'-O reversibly blocked nucleobase. In some embodiments, the detectable label can be attached to a 5' $CH_2O$— moiety of the nucleoside. The detectably labeled nucleoside analogue can be used in sequencing-by-synthesis or sequencing-by-ligation methods that include a step of detecting the detectable label. For example, the nucleoside analogue can be incorporated into a primer by a polymerase-mediated primer extension reaction. Alternatively, an oligonucleotide containing an incorporated analogue can be ligated to an anchor primer. The detectable label in the extended primer or ligated oligonucleotide may then be detected.

In another aspect, the nucleoside analogue includes an affinity tag (e.g., biotin) attached via a cleavable linker to the 3'-O reversibly blocked nucleobase. The affinity tagged nucleoside analogue can be used in sequencing-by-synthesis or sequencing-by-ligation methods that include a step of detecting the affinity tag with a detectably labeled affinity agent. For example, the nucleoside analogue can be incorporated into a primer by a polymerase-mediated primer extension reaction. Alternatively, an oligonucleotide containing an incorporated analogue can be ligated to an anchor primer. The affinity tag in the extended primer or ligated oligonucleotide may then be bound by a detectably labeled affinity agent. The incorporated nucleoside or oligonucleotide containing the nucleoside can then be detected by detecting the bound affinity agent.

II. Definitions

As used herein, the term "complementary polynucleotide" refers to a polynucleotide complementary to a target nucleic acid. In one approach, the complementary polynucleotide is formed in a sequencing-by-synthesis reaction by sequential addition of nucleosides (e.g., naturally occurring nucleoside monophosphate molecules or analogs thereof) or groups of nucleosides to a primer using the target nucleic acid as a template.

As used herein, the term "nucleobase" refers to a nitrogenous base that can base-pair with a complementary nitrogenous base of a template nucleic acid. Exemplary nucleobases include adenine (A), cytosine (C), guanine (G), thymine (T), uracil (U), inosine (I) and derivatives of these. In one aspect, the nucleobase is a 7-deaza derivative of adenine, inosine, or guanine. In some cases, the 7-deaza adenine, inosine, and/or guanine derivatives are 7-substituted. In some cases, uracil, cytosine, thymine, and/or derivatives thereof are 5-substituted. Exemplary substitutions at the 7 position for adenine, inosine, or guanine derivatives or at the 5 position for cytosine, uracil, or thymine derivatives include an alkyne substitution (e.g., —C≡C—$CH_2$—NHR). In some cases, the 7-deaza derivative of guanine is a 7-alkyne substituted compound, such as found in compound 11, wherein $R_1$ is selected from allenyl, cyanoethyl, cyanoethenyl, formaldehyde oximyl, acrylaldehyde oximyl, propionaldehyde oximyl, and cyanoethenaldehyde oximyl.

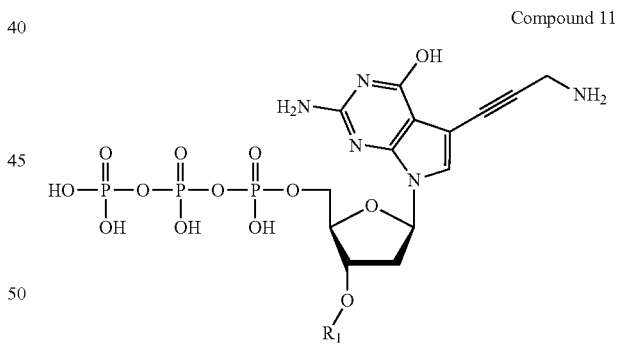

Compound 11

As used herein, the term "fluorescent dye" refers to a dye fluorophore (a chemical compound that absorbs light energy of a specific wavelength and re-emits light at a longer wavelength). Fluorescent dyes typically have a maximal molar extinction coefficient at a wavelength between about 300 nm to about 1,000 nm or at least about 5,000, more preferably at least about 10,000, and most preferably at least about 50,000 $cm^{-1}$ $M^{-1}$, and a quantum yield of at least about 0.05, preferably at least about 0.1, more preferably at least about 0.5, and most preferably from about 0.1 to about 1. Exemplary fluorescent dyes include, without limitation, acridine dyes, cyanine dyes, fluorone dyes, oxazine dyes, phenanthridine dyes, and rhodamine dyes. Exemplary fluorescent dyes include, without limitation, fluorescein, FITC, Texas Red, ROX, Cy3, Alexa Fluor 647, ATT0532, Alexa Fluor 488, ATT0647, and Cy5.

As used herein, the terms "affinity agent" and "affinity tag" refer to first and second members of a specific binding pair (SBP) or ligand-anti-ligand binding pair, where the members of the pair specifically bind to each other. For convenience, the term "affinity tag" is used to refer to the SBP member that is part of the nucleoside analog structure, and the term "affinity agent" is used to refer to the SBP member that specifically binds the affinity tag. The binding between the members of the binding pair is generally noncovalent, although a covalent disulfide linkage between binding pair members can also be used. Binding between specific binding pairs results in the formation of a binding complex, sometimes referred to as a ligand/antiligand complex or simply as ligand/antiligand. Exemplary binding pairs include, but are not limited to: (a) a haptenic or antigenic compound in combination with a corresponding antibody, or binding portion or fragment thereof; (b) a nucleic acid aptamer and protein; (c) nonimmunological binding pairs (e.g., biotin-avidin, biotin-streptavidin, biotin-Neutravidin, biotin-Tamavidin, streptavidin binding peptide-streptavidin, glutathione-glutathione S-transferase); (d) hormone-hormone binding protein; (e) receptor-receptor agonist or antagonist; (f) lectin-carbohydrate; (g) enzyme-enzyme cofactor; (h) enzyme-enzyme inhibitor; (i) complementary oligonucleotide or polynucleotide pairs capable of forming nucleic acid duplexes; (j) thio (—S—) or thiol (—SH) containing binding member pairs capable of forming an intramolecular disulfide bond; and (k) complementary metal chelating groups and a metal (e.g., metal chelated by the binding pairs nitrilotriacetate (NTA) and a 6×-His tag). Specific binding pair members need not be limited to pairs of single molecules. For example, a single ligand can be bound by the coordinated action of two or more antiligands. Affinity agents can be detectably labeled.

In the context of the binding of an affinity agent to the affinity tag of a nucleoside analogue, the terms "specific binding," "specifically binds," and the like refer to the preferential association of an affinity agent with a nucleoside analogue bearing a particular target affinity tag in comparison to a nucleoside analogue base lacking the affinity tag or having an alternative affinity tag. Specific binding between an affinity agent and affinity tag generally means an affinity of at least $10^{-6}$ $M^{-1}$ (i.e., an affinity having a lower numerical value than $10^{-6}$ $M^{-1}$ as measured by the dissociation constant $K_d$). Affinities greater than $10^{-8}$ $M^{-1}$ are preferred. Specific binding can be determined using any assay for antibody binding known in the art, including Western Blot, enzyme-linked immunosorbent assay (ELISA), flow cytometry, immunohistochemistry, and detection of fluorescently labeled affinity agent bound to a nucleoside analogue bearing a target affinity tag in a sequencing reaction.

As used herein, the term "non-fluorescent affinity tag" refers to an affinity tag that is not a fluorescent dye (i.e., does not comprise a fluorophore). In various exemplary embodiments, "non-fluorescent affinity tag" refers an affinity tag that is not fluorescein or a fluorescein derivative, not a rhodamine fluorescent dye (e.g., Texas Red), not a cyanine fluorescent dye (e.g., Cy 2, Cy 3, Cy 3.5, Cy 5, Cy 5.5, Cy 7, Cy 7.5, and the like), not a boron-dipyrromethene fluorescent dye (e.g., BODIPY 493/503), not a fluorescent coumarin dye, not a phenoxazine fluorescent dye, not an acridine fluorescent dye, not an ALEXA FLUOR® fluorescent dye, not a DYLIGHT® fluorescent dye, not a phycoerythrin fluorescent dye, or is not an allophycocyanine fluorescent dye.

As used herein, the term "antigen" refers to a compound that can be specifically bound by an antibody. Some antigens are immunogens (see, Janeway, et al., Immunobiology, 5th Edition, 2001, Garland Publishing). Exemplary antigens used in the practice of the present invention, include polypeptides, small molecules, or nucleic acids (e.g., aptamers).

As used herein, the term "small molecule antigen" refers to a small molecule that can specifically bind an antibody. A "small molecule" in the context of a small molecule antigen refers to a molecule having a mass of less than about 1,000 Daltons (e.g., at least 50 Daltons and no more than about 1,000 Daltons). In some cases, the small molecule antigen is a small organic molecule. Exemplary small organic molecules include, but are not limited to, biotin or a derivative thereof (e.g., iminobiotin or biotin carboxylate), fluorescein or a derivative thereof (e.g., carboxyfluorescein or fluorescein isothiocyanate (FITC)), an amphetamine, a barbituate, a benzodiazepine, a cocaine metabolite, a marijuana metabolites, tetrahydrocannabinol (THC), methadone, an opiate, propoxyphene, phencyclidine (PCP), digoxigenin, digoxin, peptide antigens of less than about 1,000 Daltons, cholesterol or a derivative thereof, and a steroid hormone.

As used herein, the term "peptide antigen" refers to a primary sequence of amino acids that can specifically bind an antibody. Exemplary peptide antigens include, but are not limited to, a His tag, a Myc tag, a Flag tag, an HA tag, a V5 tag, an AviTag, a calmodulin tag, an E tag, an S tag, an SBP tag, a Softag, a Strep tag, a TC tag, a VSV tag, an Xpress tag, glutathione, an isopeptag, and a SpyTag.

As used herein, "antibody" refers to an immunoglobulin molecule (e.g., polyclonal and monoclonal antibodies), as well as genetically engineered forms such as chimeric antibodies (e.g., humanized murine antibodies), heteroconjugate antibodies (e.g., bispecific antibodies), and recombinant single chain Fv fragments (scFv), and antigen binding forms of antibody fragments (e.g., Fab, F(ab)2, VH-VL Fab fragments).

The term "detectable label," or "detection label," as used herein, refers to any atom or molecule that can be used to provide a detectable and/or quantifiable signal. Suitable labels include radioisotopes, fluorophores, chromophores, mass labels, electron dense particles, magnetic particles, spin labels, molecules that emit chemiluminescence, electrochemically active molecules, enzymes, cofactors, and enzyme substrates. In some embodiments, the detection label is a molecule containing a charged group (e.g., a molecule containing a cationic group or a molecule containing an anionic group), a fluorescent molecule (e.g., a fluorescent dye), a fluorogenic molecule, or a metal. Optionally, the detection label is a fluorogenic label. A fluorogenic label can be any label that is capable of emitting light when in an unquenched form (e.g., when not quenched by another agent). The fluorescent moiety emits light energy (i.e., fluoresces) at a specific emission wavelength when excited by an appropriate excitation wavelength. When the fluorescent moiety and a quencher moiety are in close proximity, light energy emitted by the fluorescent moiety is absorbed by the quencher moiety. Optionally, the detection label is a fluorogenic dye. In some embodiments, the fluorogenic dye is a fluorescein, a rhodamine, a phenoxazine, an acridine, a coumarin, or a derivative thereof. In some embodiments, the fluorogenic dye is a carboxyfluorescein. Further examples of suitable fluorogenic dyes include the fluorogenic dyes commercially available under the ALEXA FLUOR product line (Life Technologies; Carlsbad, Calif.). Optionally, the label is a redoxgenic label. Optionally, the label is a reduction tag, a thio- or thiol-containing molecule, or a substituted or unsubstituted alkyl.

As used herein, the term "linker" refers to a chemical moiety that links a nucleoside analogue to an affinity tag and/or detectable label. Generally, linkers useful in the present invention can be up to 30 carbon atoms in length. Preferably, the linkers are 5-15 carbon atoms in length. The types of bonds between the linker and the nucleobase, the linker and the affinity tag, and/or the linker and the detectable label include, but are not limited to, amides, amines, esters, carbamates, ureas, thioethers, thiocarbamates, thiocarbonates, and thioureas, and other bonds known by those of ordinary skill in the art.

As used herein, the term "cleavable linker" refers to a chemical moiety that links a nucleoside analogue to an affinity tag and/or detectable label, and that can be cleaved to remove the affinity tag and/or detectable label from the nucleoside analogue. Cleavage can be performed using chemical or enzymatic methods.

As used herein, the terms "alkyl," "alkenyl," and "alkynyl" include straight- and branched-chain monovalent substituents. Examples include methyl, ethyl, isobutyl, 3-butynyl, and the like. Ranges of these groups useful with the compounds and methods described herein include $C_1$-$C_{10}$ alkyl, $C_2$-$C_{10}$ alkenyl, and $C_2$-$C_{10}$ alkynyl. Additional ranges of these groups useful with the compounds and methods described herein include $C_1$-$C_8$ alkyl, $C_2$-$C_8$ alkenyl, $C_2$-$C_8$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl. "Heteroalkyl," "heteroalkenyl," and "heteroalkynyl" are defined similarly as alkyl, alkenyl, and alkynyl, but can contain O, S, or N heteroatoms or combinations thereof within the backbone. Ranges of these groups useful with the compounds and methods described herein include $C_1$-$C_{10}$ heteroalkyl, $C_2$-$C_{10}$ heteroalkenyl, and $C_2$-$C_{10}$ heteroalkynyl. Additional ranges of these groups useful with the compounds and methods described herein include $C_1$-$C_8$ heteroalkyl, $C_2$-$C_8$ heteroalkenyl, $C_2$-$C_8$ heteroalkynyl, $C_1$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl. The alkyl, alkenyl, alkynyl, heteroalkyl, heteroalkenyl, or heteroalkynyl molecules used herein can be substituted or unsubstituted. As used herein, the term "substituted" includes the addition of an alkoxy, aryloxy, amino, alkyl, alkenyl, alkynyl, aryl, heteroalkyl, heteroalkenyl, heteroalkynyl, heteroaryl, cycloalkyl, or heterocycloalkyl group to a position attached to the main chain of the alkoxy, aryloxy, amino, alkyl, alkenyl, alkynyl, aryl, heteroalkyl, heteroalkenyl, heteroalkynyl, heteroaryl, cycloalkyl, or heterocycloalkyl, e.g., the replacement of a hydrogen by one of these molecules. Examples of substitution groups include, but are not limited to, hydroxy, halogen (e.g., F, Br, Cl, or I), and carboxyl groups. Conversely, as used herein, the term "unsubstituted" indicates the alkyl, alkenyl, alkynyl, heteroalkyl, heteroalkenyl, or heteroalkynyl has a full complement of hydrogens, i.e., commensurate with its saturation level, with no substitutions, e.g., linear butane (—$(CH_2)_3$—$CH_3$).

III. Compositions

Nucleoside Analogues

Described herein are deoxyribose nucleoside analogues having a 3'-O reversible blocking group and a nucleobase. As used herein, the term "reversible blocking group" refers to a group that can be cleaved to provide a hydroxyl group at the 3'-position of the nucleoside analogue. The reversible blocking group can be cleavable by an enzyme, a chemical reaction, heat, and/or light. These 3'-O reversibly blocked deoxyribose nucleoside analogues can be used in a wide variety of nucleic acid sequencing methods, including but not limited to, sequencing by synthesis methods, and sequencing by ligation methods.

Such nucleoside analogues include but are not limited to those of Formula I:

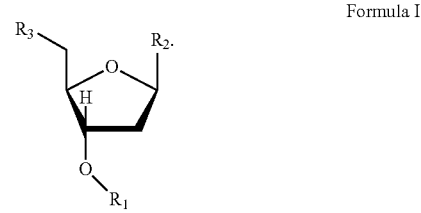

Formula I

In Formula I, $R_1$ is the 3'-O reversible blocking group (e.g., allenyl, cyanoethyl, cyanoethenyl, formaldehyde oximyl, acrylaldehyde oximyl, propionaldehyde oximyl, or cyanoethenaldehyde oximyl), $R_2$ is, or includes, the nucleobase; and $R_3$ is a cleavable linking moiety comprising at least one (e.g., 1-10), at least two (e.g., 2-10), or at least three (e.g., 3-10), phosphates, or analogues thereof (e.g., a 5'-O-1-thiophosphate). The nucleoside analogue can be suitable as a substrate for an enzyme with DNA polymerase activity. In some cases, $R_3$ is a cleavable linking moiety comprising at least three (e.g., 3-10) phosphates, or analogues thereof, and the nucleoside analogue is suitable as a substrate for a DNA polymerase. $R_2$ can, e.g., be a base selected from adenine (A), cytosine (C), guanine (G), thymine (T), uracil (U), and derivatives thereof. In some cases, the nucleoside analogue is a nucleoside triphosphate (i.e., $R_3$ consists of three consecutive phosphates). In some cases, $R_3$ is a cleavable linking moiety comprising at least three (e.g., 3-10) phosphates, or analogues thereof, and a detectable label (e.g., a fluorophore or quenched fluorophore), and the nucleoside analogue is suitable as a substrate for a DNA polymerase.

Optionally, the reversible blocking group (i.e., $R_1$) is a substituted or unsubstituted alkyl, substituted or unsubstituted alkenyl, substituted or unsubstituted alkynyl, substituted or unsubstituted heteroalkyl, substituted or unsubstituted heteroalkenyl, or substituted or unsubstituted heteroalkynyl.

In some embodiments, the reversible blocking group can be represented by Structure A, as shown below:

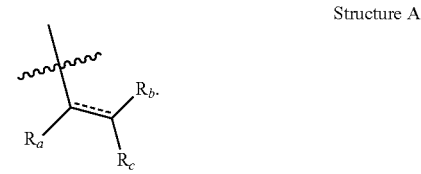

Structure A

In Structure A, $R_a$, $R_b$, and $R_c$ are each individually selected from the group consisting of hydrogen, cyano, halogen (e.g., fluoro, chloro, or bromo), nitro, alkoxy, substituted or unsubstituted amino, substituted or unsubstituted sulfonyl, substituted or unsubstituted alkyl, substituted or unsubstituted alkenyl, substituted or unsubstituted alkynyl, and substituted or unsubstituted carbonyl. Also in Structure, ≡≡≡ represents a single bond or a double bond and "∿∿" indicates where the moiety is connected to the remainder of the molecule.

In some embodiments, the reversible blocking group can be represented by Structure B, as shown below:

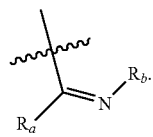

Structure B

In Structure B, $R_a$ is hydrogen, cyano, halogen (e.g., fluoro, chloro, or bromo), nitro, alkoxy, substituted or unsubstituted amino, substituted or unsubstituted alkyl, substituted or unsubstituted alkenyl, or substituted or unsubstituted alkynyl. Also in Structure B, $R_b$ is hydrogen, substituted or unsubstituted alkyl, or substituted or unsubstituted alkoxy. Additionally in Structure B, "∿∿" indicates where the moiety is connected to the remainder of the molecule.

In some embodiments, the reversible blocking group can be represented by Structure C, as shown below:

Structure C

In Structure C, $R_a$ is hydrogen, cyano, halogen (e.g., fluoro, chloro, or bromo), nitro, alkoxy, substituted or unsubstituted amino, substituted or unsubstituted sulfonyl, substituted or unsubstituted alkyl, substituted or unsubstituted alkenyl, substituted or unsubstituted alkynyl, or substituted or unsubstituted carbonyl. Also in Structure C, "∿∿" indicates where the moiety is connected to the remainder of the molecule.

Exemplary reversible blocking groups for use with the nucleoside analogues described herein include the following compounds:

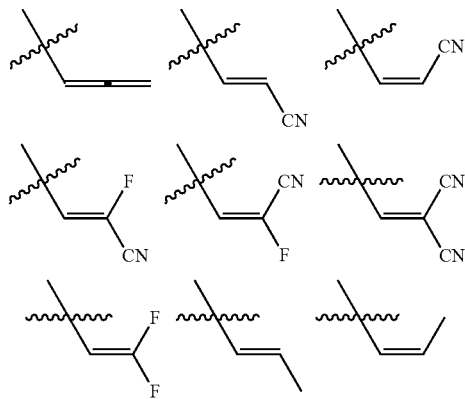

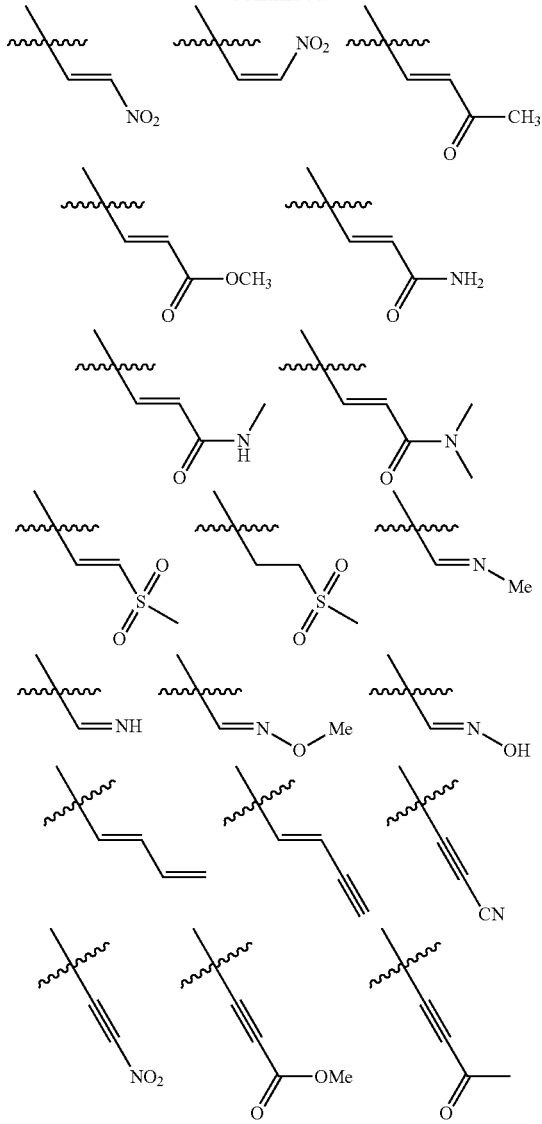

In some embodiments, the reversible blocking group is or contains allenyl (e.g., $CH_2=C=CH-$). In some embodiments, the reversible blocking group is or contains cyanoethyl (e.g., $N\equiv CCH_2CH_2-$). In some embodiments, the reversible blocking group is or contains cyanoethenyl (e.g., $N\equiv CCH=CH-$). In some embodiments, the reversible blocking group is or contains formaldehyde oximyl (e.g., $CH_2=N-$). In some embodiments, the reversible blocking group is or contains acrylaldehyde oximyl (e.g., $CH_2=CH-CH=N-$). In some embodiments, the reversible blocking group is or contains propionaldehyde oximyl (e.g., $CH\equiv C-CH=N-$). In some embodiments, the reversible blocking group is or contains cyanoethenaldehyde oximyl (e.g., $N\equiv C-CH=N-$). In some embodiments, the reversible blocking group is selected from the group consisting of allenyl, cyanoethyl, and cyanoethenyl. In some embodiments, the reversible blocking group is selected from the group consisting of formaldehyde oximyl, acrylaldehyde oximyl, propionaldehyde oximyl, and cyanoethenaldehyde oximyl. In some embodiments, the reversible blocking group is selected from the group consisting of allenyl, cyanoethyl, cyanoethenyl, formaldehyde oximyl, acrylaldehyde oximyl, propionaldehyde oximyl, and cyanoethenaldehyde oximyl.

In some embodiments, the reversible blocking group is or contains an allenyl, cyanoethyl, or cyanoethenyl moiety and a polyethylene glycol (PEG) moiety. In some embodiments, the reversible blocking group is or contains a formaldehyde oximyl, acrylaldehyde oximyl, propionaldehyde oximyl, or cyanoethenaldehyde oximyl moiety and a polyethylene glycol (PEG) moiety. In some embodiments, the reversible blocking group is or contains an allenyl, cyanoethyl, cyanoethenyl, formaldehyde oximyl, acrylaldehyde oximyl, propionaldehyde oximyl, or cyanoethenaldehyde oximyl moiety and a polyethylene glycol (PEG) moiety. In some embodiments, the reversible blocking group contains an allenyl, cyanoethyl, or cyanoethenyl moiety and a substituted or unsubstituted alkyl (i.e., a substituted or unsubstituted hydrocarbon). In some embodiments, the reversible blocking group contains a formaldehyde oximyl, acrylaldehyde oximyl, propionaldehyde oximyl, or cyanoethenaldehyde oximyl moiety and a substituted or unsubstituted alkyl (i.e., a substituted or unsubstituted hydrocarbon). In some embodiments, the reversible blocking group contains an allenyl, cyanoethyl, cyanoethenyl, formaldehyde oximyl, acrylaldehyde oximyl, propionaldehyde oximyl, or cyanoethenaldehyde oximyl moiety and a substituted or unsubstituted alkyl (i.e., a substituted or unsubstituted hydrocarbon).

The nucleoside analogues of Formula I can be labeled with a detectable label (e.g., a fluorescent label) at the $R_2$ and/or $R_3$ position. In an exemplary embodiment, the nucleoside analogues of Formula I are labeled with fluorescein, or Texas Red. In an another exemplary embodiment, the nucleoside analogues are labeled with fluorescein, FITC, Texas Red, ROX, Cy3, Alexa Fluor 647, ATTO532, Alexa Fluor 488, ATTO647, or Cy5. Methods and compositions for labeling and detecting a nucleoside analogue with a detectable label such as a fluorophore, or a fluorophore/quencher pair, at the $R_2$ and/or $R_3$ position are described, e.g., in co-pending International Patent Application PCT/US2015/057094, entitled "Signal Confinement Sequencing (SCS) and Nucleotide Analogues for Signal Confinement Sequencing," filed on Oct. 23, 2015, the content of which is hereby incorporated by reference in its entirety for all purposes.

In an exemplary embodiment, the nucleoside analogue of Formula I is a compound of Formula IA:

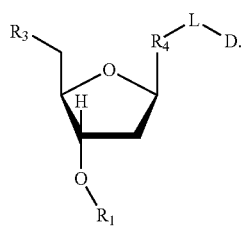

Formula IA

In Formula IA, $R_1$ is or contains a 3'-O reversible blocking group selected from allenyl, cyanoethyl, cyanoethenyl, formaldehyde oximyl, acrylaldehyde oximyl, propionaldehyde oximyl, and cyanoethenaldehyde oximyl, $R_4$ is a nucleobase; $R_3$ is a cleavable linking moiety containing three, or at least three (e.g., 3-10), phosphates, or analogues thereof; L is a linker; and D contains a detectable label (e.g., a fluorescent label). In some cases, $R_3$ contains at least one thiophosphate, such as a 5'-O-1-thiophosphate. $R_4$ can, e.g., be a base selected from adenine (A), cytosine (C), guanine (G), thymine (T), uracil (U), and derivatives of these. In some cases, $R_3$ is a cleavable linking moiety containing three phosphates, or analogues thereof, and the nucleoside analogue of Formula Ia is suitable as a substrate of a DNA polymerase.

In some cases, the deoxyribose nucleoside analogues include but are not limited to deoxyribose nucleoside triphosphate analogues of Formula II:

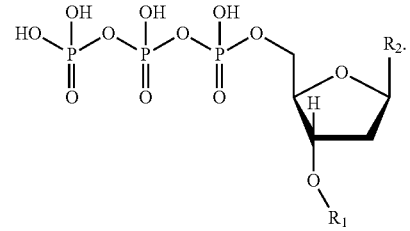

Formula II where $R_1$ is the 3'-O reversible blocking group (e.g., allenyl, cyanoethyl, cyanoethenyl, formaldehyde oximyl, acrylaldehyde oximyl, propionaldehyde oximyl, or cyanoethenaldehyde oximyl), and $R_2$ is the nucleobase.

In some cases, the deoxyribose nucleoside analogues include but are not limited to those of Formula III:

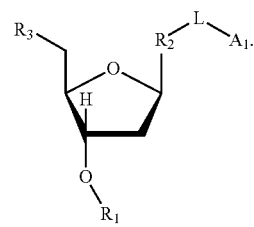

Formula III

In Formula III, $R_1$ is or contains a 3'-O reversible blocking group selected from allenyl, cyanoethyl, cyanoethenyl, formaldehyde oximyl, acrylaldehyde oximyl, propionaldehyde oximyl, and cyanoethenaldehyde oximyl; $R_2$ is a nucleobase; $R_3$ is a cleavable linking moiety containing at least one (e.g., 1-10), at least two (e.g., 2-10), or at least three (e.g., 3-10), phosphates, or analogues thereof; L is a linker; and $A_1$ is a fluorescent or non-fluorescent affinity tag. In some cases, $R_3$ is a cleavable linking moiety comprising at least three (e.g., 3-10), phosphates, or analogues thereof, and the nucleoside analogue is suitable as a substrate of a DNA polymerase. In some cases, $R_3$ comprises at least one thiophosphate, such as a 5'-O-1-thiophosphate.

The affinity tag can be, e.g., any of the affinity tags, ligands, or antiligands described herein. In some cases, $A_1$ is an antigen that can be specifically bound by an antibody. In some cases, $A_1$ is a non-fluorescent affinity tag. In some cases, $A_1$ is biotin. In some cases, $A_1$ is not biotin. In some embodiments, the affinity tag is an antibody, an amino acid, cholesterol, FITC, Texas Red, an antigen, a peptide, a peptide antigen, or a small molecule antigen. Optionally, the affinity tag contains an oligonucleotide. In some cases, the affinity tag contains a thio (—S—) or a thiol (—SH) moiety. In some cases, the affinity tag is or contains a metal chelating group (e.g., nitriloacetic acid (NTA), iminodiacetic acid (IDA), or a six-His peptide tag), optionally in complex with a metal (e.g., nickel, zinc, cobalt, copper, etc.). Such metal chelating groups, when in complex with a metal, can be detected with an detectably labeled affinity agent containing a complementary metal chelating group.

Nucleoside Analogue Mixtures

The nucleoside analogues described herein can be provided or used in the form of a mixture. For example, the mixture can contain two, three, or four structurally different nucleoside analogues. The structurally different nucleoside analogues can differ at the nucleobase. For example, the mixture can contain four structurally different nucleoside analogues containing the four natural DNA nucleobases (i.e., adenine, cytosine, guanine, and thymine), or derivatives thereof. In some cases, each nucleoside analogue having a structurally different nucleobase can have a distinguishable detectable label or affinity tag. Alternatively, the mixture can contain four different nucleoside analogues but only three different detectable labels or affinity tags, wherein the fourth nucleoside analogue is unlabeled and/or untagged. Alternatively, the mixture can contain four structurally different nucleoside analogues that are used for two-color sequencing, such that a first nucleoside analogue is labeled with a first affinity tag or detectable label, the second nucleoside analogue is labeled with a second affinity tag or detectable label, the third nucleoside analogue is labeled with the first and second affinity tag or detectable label (e.g., is a mixture of third nucleoside analogues labeled with the first affinity tag or label and third nucleotide analogues labeled with the second affinity tag or label), and the fourth nucleoside analogue is unlabeled and/or untagged.

Linkers

A nucleoside analogue as described herein can be attached to a label (e.g., an affinity label and/or a detectable label) via a linker. Optionally, the linker used for attaching the nucleoside analogue to the label can be a cleavable linker. The linker can optionally be attached to the nucleobase of the nucleoside analogue. For example, the linker can be attached to the 5-position in a pyrimidine nucleobase or to the 7-position in a purine or deazapurine nucleobase. The linker can optionally be attached to a phosphate group located at the 5'-position of the nucleoside analogue.

Optionally, the linkers can be cleavable linkers. In nucleic acid sequencing and resequencing methods, the use of cleavable linkers between the nucleoside analogue and the label (e.g., the affinity label and/or the detectable label) allows the removal of the label after incorporation and detection of the nucleoside analogue. Optionally, the cleavable linkers are attached (e.g., covalently bonded) to the nucleoside analogue through the nucleobase of the nucleoside analogue. Optionally, the cleavable linkers are attached (e.g., covalently bonded) to the nucleoside analogue through a phosphate group at the 5' position of the nucleoside analogue. The cleavable linkers as described herein can be cleaved to remove the label from the nucleoside analogue without otherwise altering the nucleoside analogue.

Cleavage can be performed using chemical or enzymatic methods. For example, cleavage can be performed by acid treatment, base treatment, oxidation, reduction, hydrolysis, or by photobleaching. Optionally, cleavage can be performed using phosphine-containing compounds or systems (e.g., phosphine-based transition metal catalysts or water-soluble phosphines). The appropriate cleavage method depends on the nature of the linkage, which can be determined by those of ordinary skill in the art.

The cleavable linkers can include, for example, an azido group, an allyl group, a disulfide bond, an amide group, or an alkoxy group. Optionally, the cleavable linker contains at least one moiety that is present in the 3'-O reversible blocking group. For example, the cleavable linker can contain at least one of the following groups: allenyl, cyanoethyl, cyanoethenyl, formaldehyde oximyl, acrylaldehyde oximyl, propionaldehyde oximyl, or cyanoethenaldehyde oximyl groups. Exemplary linkers for use as cleavable linkers in the nucleotide analogues described herein include the following moieties:

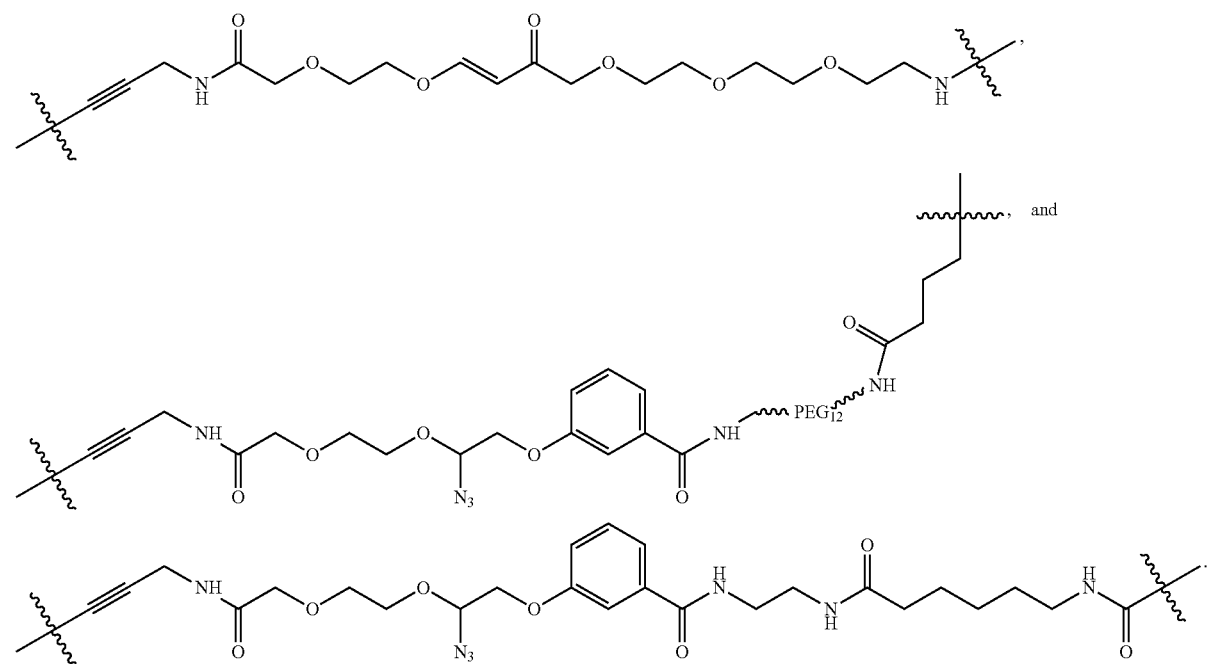

Optionally, an exemplary linker for including in the nucleoside analogues described herein can be prepared from a reagent as shown below:

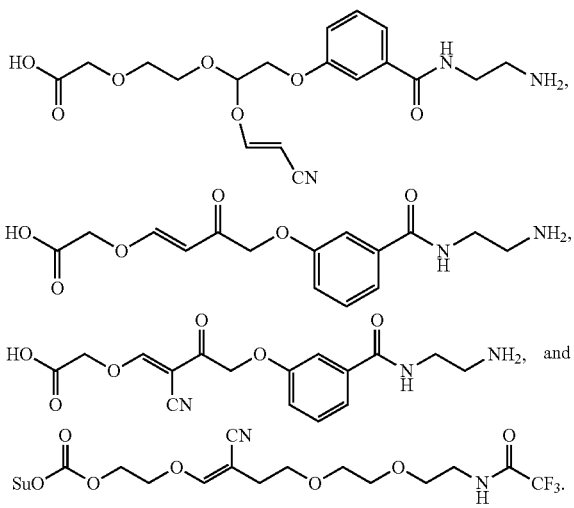

Detectable Labels

Nucleobases or nucleoside analogues containing the nucleobase, as described herein, can be covalently linked to a detectable label (e.g., via a linker, as described above). The presence or absence of the detectable label can be detected to determine the sequence of a template nucleic acid. Similarly, affinity agents described herein can be detectably labeled. Detectably labeled affinity agents can be used to detect the presence or absence of a nucleoside analogue, or a reaction product thereof, having a corresponding affinity tag. Thus, the presence or absence of a detectably labeled nucleobase, nucleoside analogue, affinity agent bound to a nucleobase or nucleoside analogue, or reaction product thereof, can be detected to determine the sequence of a template nucleic acid. In some embodiments, the detectable label is a reporter molecule capable of generating a fluorescence signal. Exemplary reporter molecules are fluorescent organic dyes, which may be derivatized for attachment to an affinity agent, nucleobase, or nucleoside analogue.

There is a great deal of practical guidance available in the literature for selecting appropriate detectable labels for attachment to an affinity agent or nucleoside analogue, as exemplified by the following references: Grimm et al., 2013, "The chemistry of small-molecule fluorogenic probes," Prog Mol Biol Transl Sci. 113:1-34, incorporated herein by reference, and Oushiki et al., 2012, "Near-infrared fluorescence probes for enzymes based on binding affinity modulation of squarylium dye scaffold," Anal Chem. 84:4404-10; Medintz & Hildebrandt, editors, 2013, "FRET—Förster Resonance Energy Transfer: from theory to applications," (John Wiley & Sons), and the like. The literature also includes references providing lists of fluorescent molecules, and their relevant optical properties for choosing fluorophores or reporter-quencher pairs, e.g., Haugland, Handbook of Fluorescent Probes and Research Chemicals (Molecular Probes, Eugene, 2005); and the like. Further, there is extensive guidance in the literature for derivatizing reporter molecules for covalent attachment via common reactive groups that can be added to a nucleoside, nucleobase, or affinity agent, as exemplified by the following references: Ullman et al., U.S. Pat. No. 3,996,345; Khanna et al., U.S. Pat. No. 4,351,760; and the like. Each of the aforementioned publications is incorporated herein by reference in its entirety for all purposes.

Exemplary reporter molecules may be selected from xanthene dyes, including fluoresceins, and rhodamine dyes. Many suitable forms of these compounds are widely available commercially with substituents on their phenyl moieties which can be used as the site for linking to an affinity agent. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate, and 2-p-toluidinyl-6-naphthalene sulfonate. Other dyes include 3-phenyl-7-isocyanatocoumarin; acridines, such as 9-isothiocyanatoacridine and acridine orange; N-(p-(2-benzoxazolyl)phenyl)maleimide; benzoxadiazoles; stilbenes; pyrenes; and the like.

In some embodiments, reporter molecules are selected from fluorescein and rhodamine dyes. These dyes and appropriate linking methodologies are described in many references, e.g., Khanna et al. (cited above); Marshall, Histochemical J., 7:299-303 (1975); Menchen et al., U.S. Pat. No. 5,188,934; Menchen et al., European Patent Application 87310256.0; and Bergot et al., International Application PCT/US90/05565. Fluorophores that can be used as detectable labels for affinity agents or nucleoside analogues include, but are not limited to, rhodamine, cyanine 3 (Cy 3), cyanine 5 (Cy 5), fluorescein, Vic®, Liz®, Tamra®, 5-Fam®, 6-Fam®, 6-HEX, CAL Fluor Green 520, CAL Fluor Gold 540, CAL Fluor Orange 560, CAL Fluor Red 590, CAL Fluor Red 610, CAL Fluor Red 615, CAL Fluor Red 635, and Texas Red (Molecular Probes).

By judicious choice of labels, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 1972; and Haugland, Handbook of Fluorescent Probes and Research Chemicals, Molecular Probes, Eugene (2005). In some embodiments, the presence or absence of nucleoside analogues having distinct affinity tags can be simultaneously and differentially detected with corresponding differentially labeled affinity agents. Such nucleoside analogue/affinity agent pairs can be used in two-, three-, or four-color sequencing.

Similarly, two-, three-, or four-color sequencing can be performed using differentially labeled nucleoside analogues having an, e.g., fluorescent, detectable label covalently linked (e.g., via a linker) to the nucleobase and/or 5' phosphate. For example, nucleoside analogues comprising a reversible 3'-O blocking group selected from the group consisting of allenyl, cyanoethyl, cyanoethenyl, formaldehyde oximyl, acrylaldehyde oximyl, propionaldehyde oximyl, and cyanoethenaldehyde oximyl and a detectable label covalently linked (e.g., via a linker) to the nucleobase or 5' phosphate can be used in two-, three-, or four-color sequencing as described below.

Affinity Agents

Affinity agents can be used to detect the presence or absence of a nucleoside analogue, or a reaction product thereof, having a corresponding affinity tag. For example, the affinity agents can be used to detect incorporation of a nucleoside analogue having a corresponding affinity tag in a polynucleotide generated by a sequencing by synthesis or sequencing by ligation reaction.

In some embodiments, the affinity agent is a thio- or thiol-containing molecule, a protein, or a dendrimer. In some embodiments, the affinity agent is streptavidin, neutravidin, a tamavidin, glutathione S-transferase, thioredoxin, maltose binding protein, a lectin, or calmodulin binding protein. In some embodiments, the affinity agent is an antibody. In some embodiments, the affinity agent comprises an oligonucleotide complementary to an oligonucleotide affinity tag that is covalently linked to the nucleoside analogue. In some embodiments, the affinity agent comprises an oligonucleotide aptamer that specifically binds to an affinity tag (e.g., a peptide or protein affinity tag) that is covalently linked to the nucleoside analogue. In some embodiments, the affinity agent is a polynucleotide concatemer comprising multiple copies of a complementary affinity agent sequence or multiple copies of an aptamer affinity agent sequence. In some embodiments, the affinity agent contains a metal chelating group (e.g., a six-His tag, or an NTA, or IDA group) capable of forming a ternary metal-chelate complex (chelate-metal-chelate) with a corresponding metal chelating group affinity tag covalently linked to the nucleoside analogue (e.g., a six-His tag, or an NTA, or IDA group).

One of ordinary skill in the art will recognize that an affinity agent and affinity tag binding pair can be interchanged. Thus the affinity agents described herein (e.g., unlabeled affinity agents) can be used as affinity tags (e.g., covalently linked to a nucleoside analogue). Moreover, the affinity tags described herein (e.g., detectably labeled affinity tags) can be used as affinity agents to detect the presence or absence of a nucleoside analogue.

Labeled Oligonucleotides

Nucleoside analogues described herein can be used to sequence a template nucleic acid by a variety of methods. A variety of different oligonucleotides containing the nucleoside analogue, or a reaction product thereof, can be generated, depending on the sequencing method used and the nucleoside analogue employed. Examples of such oligonucleotides containing a nucleoside analogue of the present invention, or a reaction product thereof, are further described herein. Nucleoside analogues described herein, including those incorporated into an oligonucleotide, can also be useful in a variety of applications other than sequencing, as will be apparent to those of skill in the art. For example, nucleoside analogues described herein that include a fluorescent label covalently linked to a nucleobase can be used in a single nucleotide primer extension assay, such as described in Synvänen, AC, Nature Reviews Genetics 2, 930-942 (December 2001). As another example, nucleoside analogues described herein that include a fluorescent label covalently linked to an affinity tag can be used to hybridize to and isolate target nucleic acid fragments.

In one aspect, an oligonucleotide containing a nucleoside analogue, can be hybridized to a template nucleic acid adjacent to an anchor sequence. The oligonucleotide may be ligated to the anchor sequence and the oligonucleotide detected. Detection of the nucleoside analogue identifies the oligonucleotide and thus the sequence of bases complementary to the template nucleic acid, thereby providing the sequence of the template nucleic acid. A 3'-O reversible blocking group of the incorporated nucleoside analogue, and optionally a detectable label or affinity tag, can be removed for further rounds of hybridization, ligation, and detection. In some embodiments, the nucleoside analogue comprises a fluorescent detectable label or affinity tag (e.g., linked to a nucleobase) and is incorporated into an oligonucleotide. In some cases, the nucleoside analogue is incorporated at the 3' end of the oligonucleotide. Such 3' end incorporation can be useful, e.g., for sequencing by ligation in the 5' to 3' direction.

Such oligonucleotides can comprise a nucleoside analogue of Formula IV:

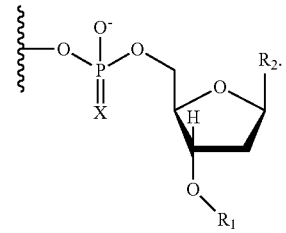

Formula IV

In some cases, $R_1$ is or contains a reversible blocking group selected from allenyl, cyanoethyl, cyanoethenyl, formaldehyde oximyl, acrylaldehyde oximyl, propionaldehyde oximyl, and cyanoethenaldehyde oximyl; $R_2$ is or contains a nucleobase; and the nucleoside analogue is covalently linked via the 5' phosphate to an oligonucleotide, wherein:

indicates the location of the 5' phosphodiester bond to the oligonucleotide. X can be selected from O and S.

In an exemplary embodiment, $R_2$ contains or is a nucleobase, a linker, and a detectable label; or a nucleobase, a linker, and an affinity tag. In some cases, cleavage of the linker between nucleobase and detectable label or affinity tag can be performed under the same conditions as cleavage of the reversible blocking group. In some cases, the linker is not cleavable. In some cases, the linker is cleavable under orthogonal conditions relative to cleavage of the reversible blocking group.

In another aspect, a nucleoside analogue complementary to a template nucleic acid position and comprising a detectable label or an affinity tag (e.g., linked to a nucleobase) is incorporated into an oligonucleotide during a sequencing by synthesis reaction via a polymerase enzyme. Detection of the nucleoside analogue indicates the sequence of the base complementary to the template nucleic acid, thereby providing the sequence of the template nucleic acid. In some embodiments, the nucleoside analogue contains a fluorescent detectable label or affinity tag (e.g., linked to a nucleobase) and is incorporated into a oligonucleotide.

Nucleoside analogues of Formula IV, wherein $R_2$ includes or is a nucleobase (e.g., a nucleobase that is not labeled with an affinity agent or detectable label) can also be utilized for sequencing by synthesis reaction schemes that do not rely on a specific step of detecting a distinguishable label. For example, pyrosequencing reaction schemes—in which nucleoside analogues of each of the four DNA nucleobases (A, G, C, and T) are delivered in succession and detected by a coupled assay for detection of pyrophosphate produced during incorporation of the nucleoside analogue by a polymerase—do not require a labeled or affinity tagged nucleobase. As such, the present invention also includes such nucleoside analogues of Formula IV wherein $R_2$ is a nucleobase, and their use in "label-free" (e.g., pyrosequencing) sequencing reactions.

Nucleoside analogues of Formula IV, wherein $R_2$ includes a nucleobase, a linker, and a detectable label can be covalently (e.g., via disulfide linkage) or non-covalently bound to a detectably labeled affinity agent. The presence or absence of the detectably labeled affinity agent can be determined to identify the sequence of the complementary base of the template nucleic acid in a sequencing by ligation or sequencing by synthesis reaction. Such oligonucleotides can contain a nucleoside analogue of Formula V:

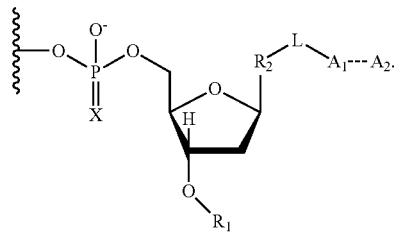

Formula V

In Formula V, $R_1$ is or contains a reversible blocking group selected from allenyl, cyanoethyl, cyanoethenyl, formaldehyde oximyl, acrylaldehyde oximyl, propionaldehyde oximyl, and cyanoethenaldehyde oximyl; $R_2$ is a nucleobase; L is a linker; $A_1$ is or contains a fluorescent or non-fluorescent affinity tag; and $A_2$ is or includes a detectably labeled affinity agent that forms a specific complex with $A_1$. X can be selected from O and S.

In some cases, $A_2$ includes a detectably labeled affinity agent that forms a specific and non-covalent complex with $A_1$. In some cases, $A_1$ includes one or more thio (—S—) or thiol (—SH) groups, $A_2$ includes a detectably labeled affinity agent containing one or more thio (—S—) or thiol (—SH) groups, and $A_2$ forms a specific and covalent disulfide-mediated complex with $A_1$.

Exemplary Nucleoside Analogues

Exemplary nucleoside analogues as described herein include the following compounds:

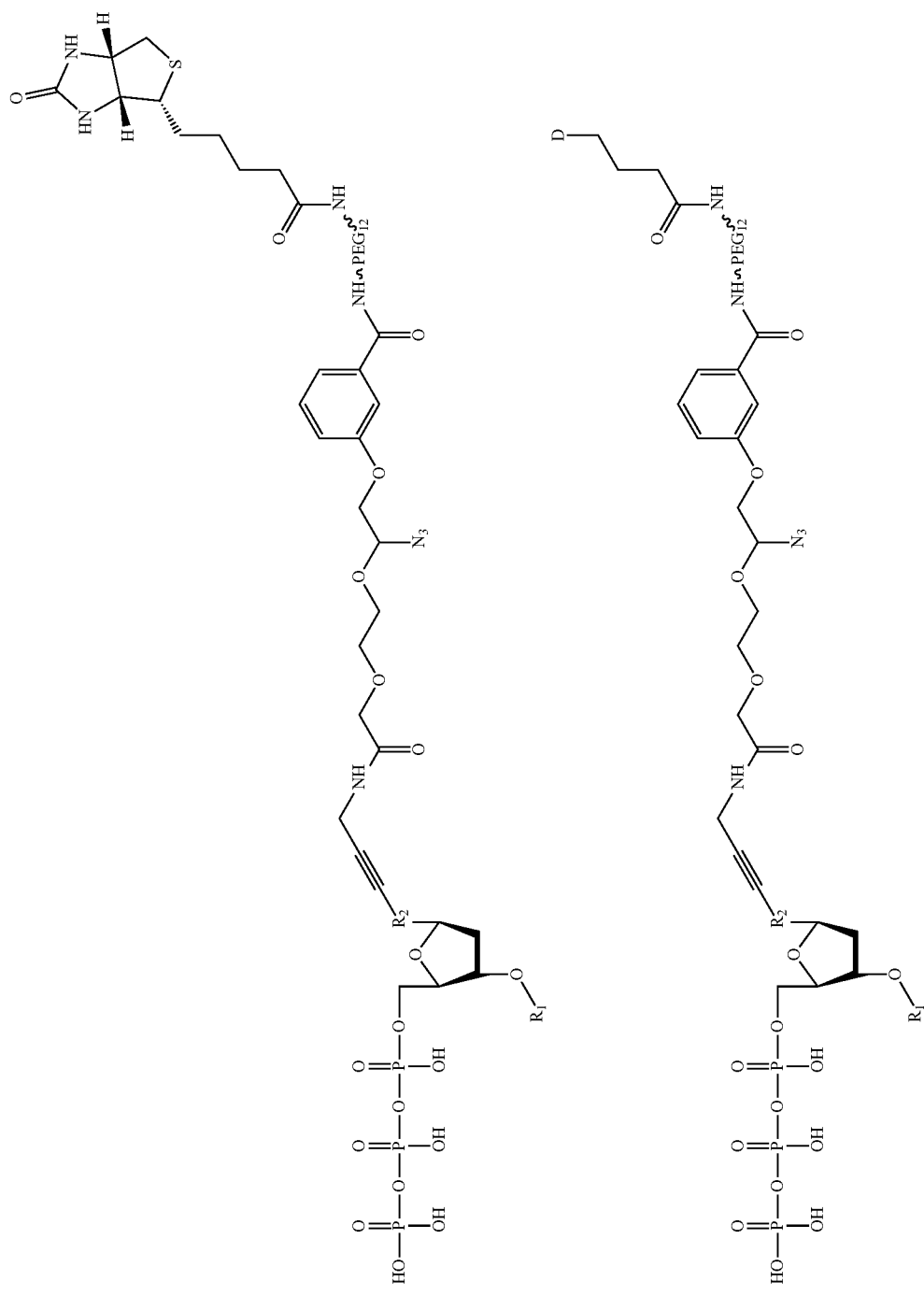

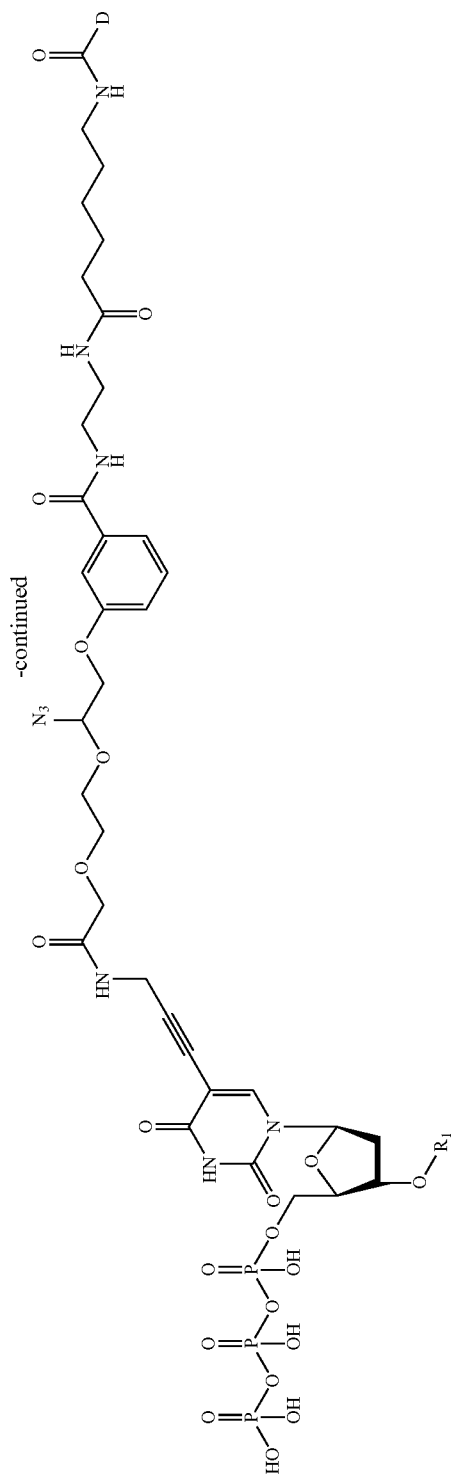
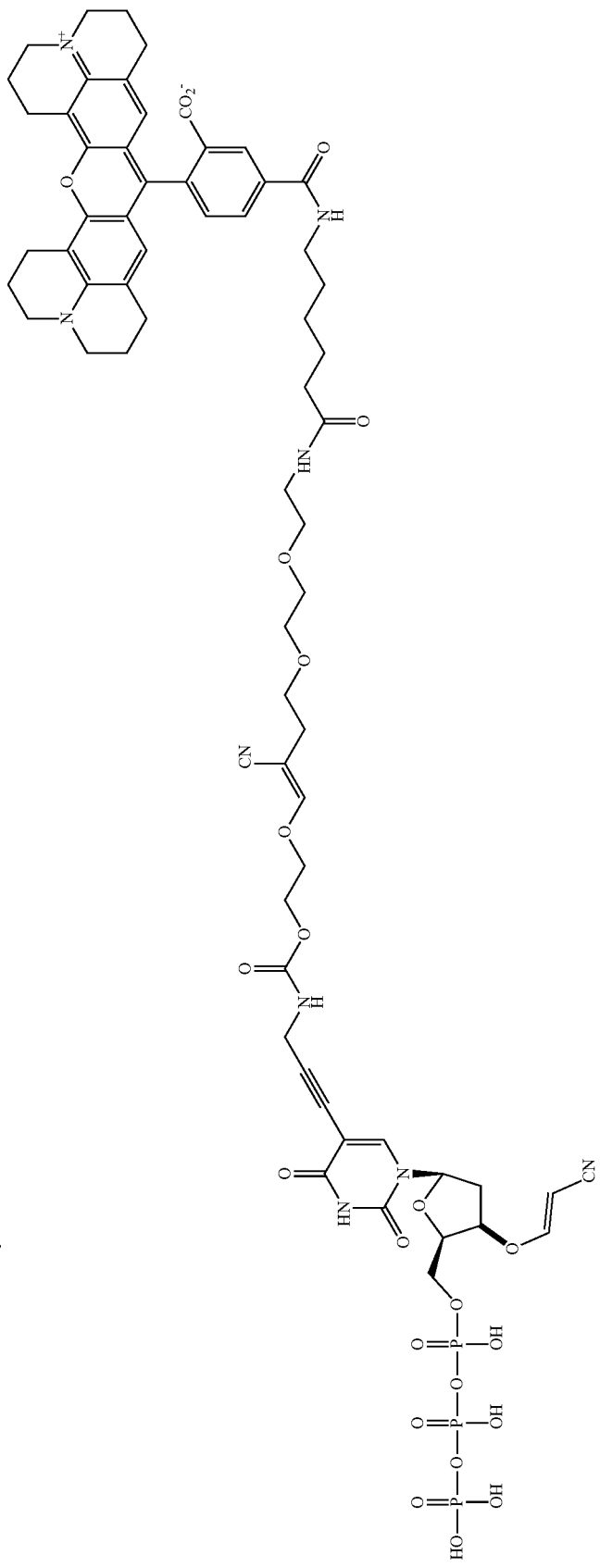

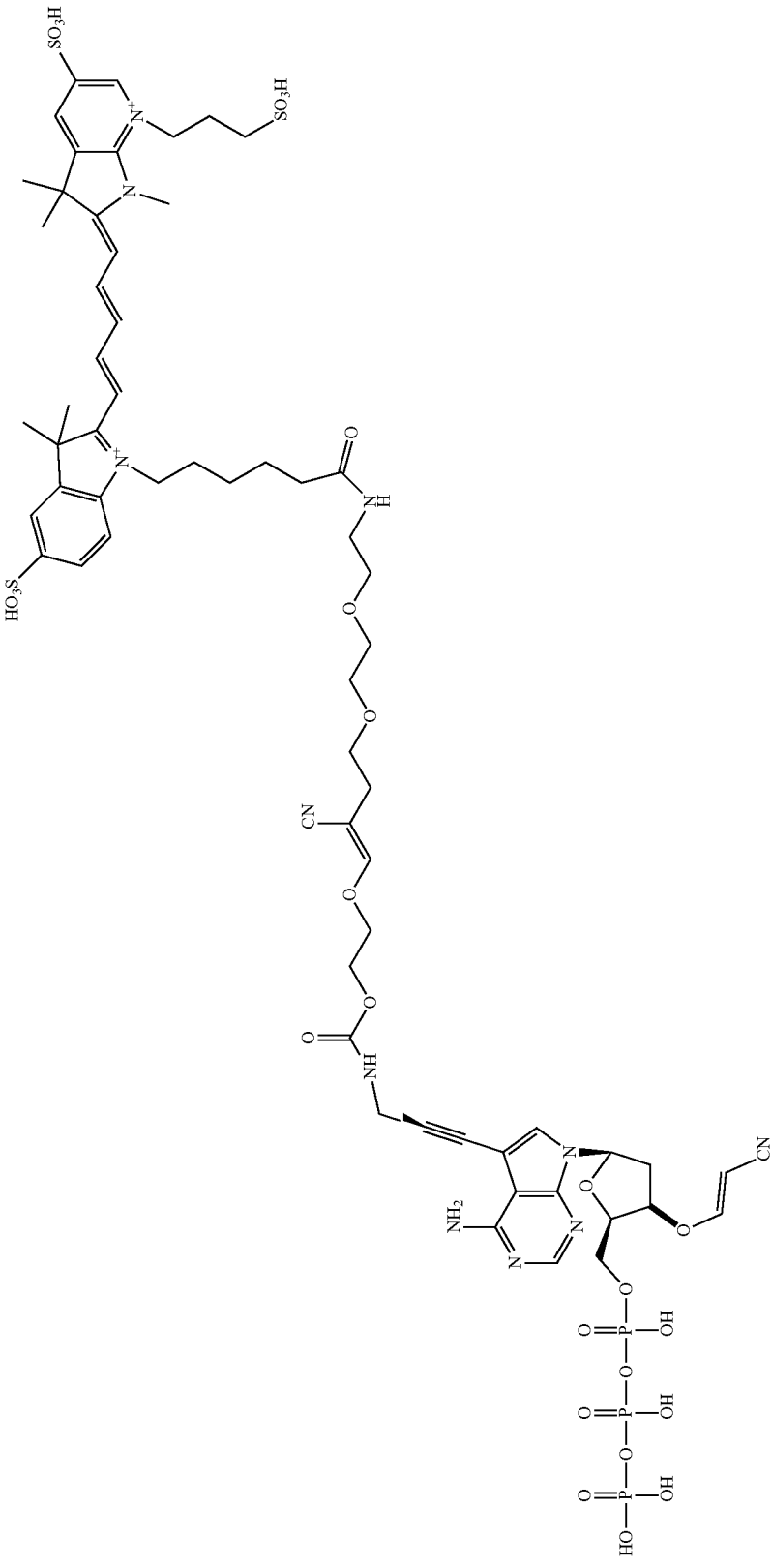

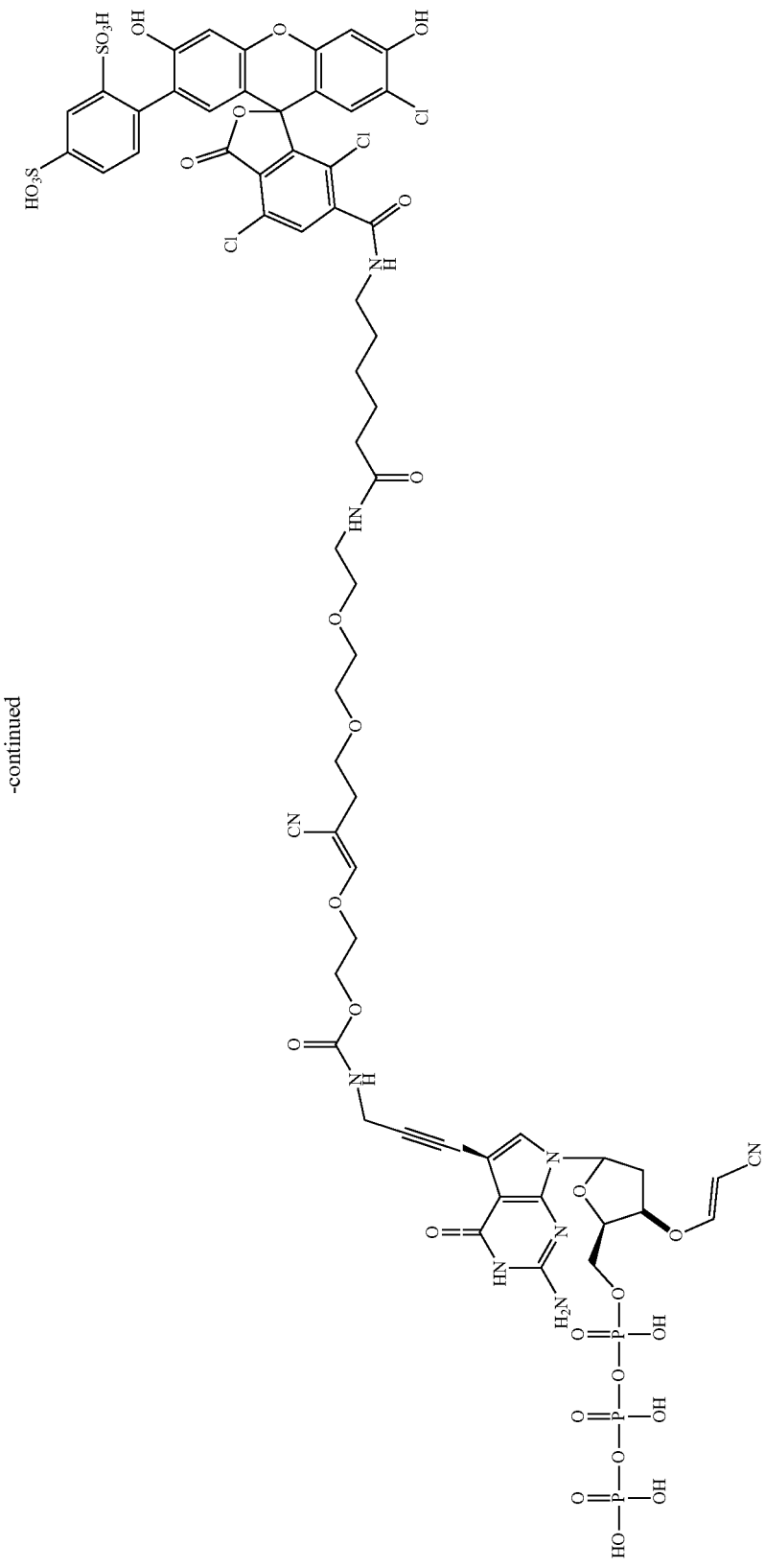

-continued
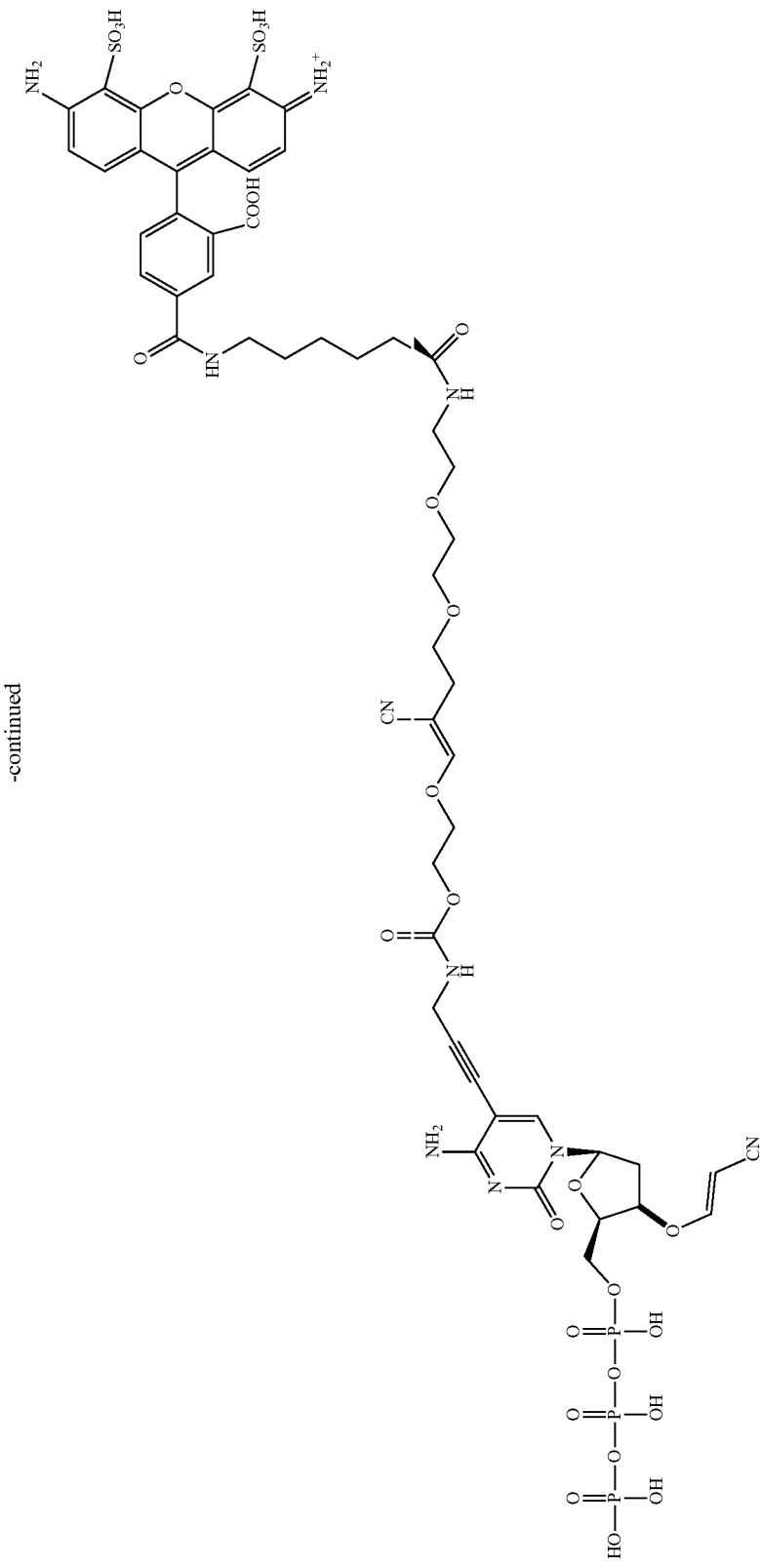

Reaction Mixtures

Nucleoside analogues and oligonucleotides containing such nucleoside analogues or reaction products thereof can be used as a component of a reaction mixture. For example, such components can be used in reaction mixtures for nucleic acid sequencing (e.g., sequencing by synthesis or by ligation). Exemplary reaction mixtures include, but are not limited to, those containing (a) template nucleic acid; (b) polymerase; (c) oligonucleotide primer; and (d) a 3'-O reversibly blocked nucleoside analogue, or a mixture of such 3'-O reversibly blocked nucleoside analogues having structurally different nucleobases. The 3'-O reversible blocking group can be, or contain, an allenyl, cyanoethyl, cyanoethenyl, formaldehyde oximyl, acrylaldehyde oximyl, propionaldehyde oximyl, or cyanoethenaldehyde oximyl moiety, or a combination thereof.

The reaction mixture can further optionally contain one or more of: ATP sulfurylase, luciferase, apyrase, adenosine 5' phosphosulfate; and luciferin. In some cases, such a reaction mixture includes (a) template nucleic acid; (b) polymerase; (c) oligonucleotide primer; (d) a 3'-O reversibly blocked adenosine nucleoside analogue having an alpha thiophosphate; (e) ATP sulfurylase, (f) luciferase, (g) apyrase, (h) adenosine 5' phosphosulfate; and (i) luciferin. In some cases, the adenosine nucleoside analogue having an alpha thiophosphate is an adenine nucleotide or derivative thereof that is not detectably labeled with a fluorophore or affinity tag, and contains a 3'-O reversible blocking group selected from allenyl, cyanoethyl, cyanoethenyl, formaldehyde oximyl, acrylaldehyde oximyl, propionaldehyde oximyl, and cyanoethenaldehyde oximyl.

Alternatively, the reaction mixture can contain a 3'-O reversibly blocked nucleoside analogue, where the nucleobase is covalently linked to a linker, and the linker is linked to an affinity tag or detectable label. In some cases, the reaction mixture contains a mixture of nucleoside analogues having different nucleobases, where the nucleobases are covalently linked to a detectable and distinguishable label or affinity tag via a linker. In some cases, the reaction mixture further contains one or more detectably and distinguishably labeled affinity agents. Labeled nucleobases or labeled affinity agents can, e.g., be labeled with detectable fluorescent organic dyes, e.g., detectable and distinguishable fluorescent organic dyes.

Template Nucleic Acids

In various embodiments, the template polynucleotide is DNA (e.g., cDNA, genomic DNA, or amplification products) or RNA. In various embodiments, the polynucleotide is double stranded or single stranded.

In some embodiments, the template nucleic acid is immobilized on a solid surface. In some embodiments, the template nucleic acid is immobilized on a substrate (e.g., a bead, flow cell, pad, channel in a microfluidic device and the like). The substrate may comprise silicon, glass, gold, a polymer, PDMF, and the like.

In some embodiments, the template nucleic acid is immobilized or contained within a droplet (optionally immobilized on a bead or other substrate within the droplet).

In some embodiments, the template nucleic acid is an immobilized DNA concatemer comprising multiple copies of a target sequence. In some embodiments, the template nucleic acid is represented as a DNA concatemer, such as a DNA nanoball (DNB) comprising multiple copies of a target sequence and an "adaptor sequence". See International Patent Publication No. WO 2007133831, the content of which are hereby incorporated by reference in its entirety for all purposes. In some embodiments the template is a single polynucleotide molecule. In some embodiments the template is present as a clonal population of template molecules (e.g., a clonal population produced by bridge amplification or Wildfire amplification).

It will be understood that the method is not limited to a particular form of template, and the template can be any template such as, for example, a DNA concatemer, a dendrimer, a clonal population of templates (e.g., as produced by bridge amplification or Wildfire amplification) or a single polynucleotide molecule. Thus, importantly, the specification should be read as if each reference to a template can alternatively refer to a concatemer template, a clonal population of short linear templates, a single molecule template (e.g., in a zero-mode waveguide), and templates in other forms.

Suitable template nucleic acids, including DNBs, clusters, polonys, and arrays or groups thereof, are further described in U.S. Pat. Nos. 8,440,397; 8,445,194; 8,133,719; 8,445,196; 8,445,197; 7,709,197; 12/335,168, 7,901,891; 7,960,104; 7,910,354; 7,910,302; 8,105,771; 7,910,304; 7,906,285; 8,278,039; 7,901,890; 7,897,344; 8,298,768; 8,415,099; 8,671,811; 7,115,400; 8,236,499, and U.S. Patent Publication Nos. 2015/0353926; 2010/0311602; 2014/0228223; and 2013/0338008, all of which are hereby incorporated by reference in their entirety for all purposes and particularly for all disclosure related to nucleic acid templates, concatemers and arrays according to the present invention.

IV. Methods

Cleavage of Blocking Groups or Linkers

Nucleoside analogues described herein are 3'-O reversibly blocked. In some aspects, the blocking group provides for controlled incorporation of a single 3'-O reversibly blocked nucleoside analogue into a sequencing by synthesis primer, e.g., a sequencing by synthesis primer that has been extended in a previous cycle. Similarly, the blocking group provides for controlled incorporation of a single oligonucleotide containing a 3'-O reversibly blocked nucleoside analogue into an adjacent sequencing by ligation anchor primer or previously extended anchor primer. After incorporation and detection, the reversibly blocked nucleoside analogue, or an oligonucleotide containing such an analogue, can be treated to cleave the blocking group and allow further rounds of extension by polymerase or ligase.

The 3'-O reversible blocking group can be removed by enzymatic cleavage or chemical cleavage (e.g., hydrolysis). The conditions for removal can be selected by one of ordinary skill in the art based on the descriptions provided herein, the chemical identity of the blocking group to be cleaved, and nucleic acid chemistry principles known in the art. In some embodiments, the blocking group is removed by contacting the reversibly blocked nucleoside with a reducing agent such as dithiothreitol (DTT), or a phosphine reagent such as tris(2-carboxyethyl)phosphine (TCEP), tris(hydroxymethyl)phosphine (THP), tris(3-hydroxypropyl)phosphine (THPP), 1,3,5-triaza-7-phosphaadamantane (PTA), 1,4,7-triaza-9-phosphatricyclo[5.3.2.1]-tridecane (CAP), proazaphosphatrane, trialkylphosphines, and aminophosphines.

Exemplary reducing agents include $Na_2S_2O_3$, $Na_2SO_3$, $NaN_3$, $EtNO_2$, $CH_2(CN)_2$, and $NEt_3$. Further examples of suitable reducing agents are shown below:

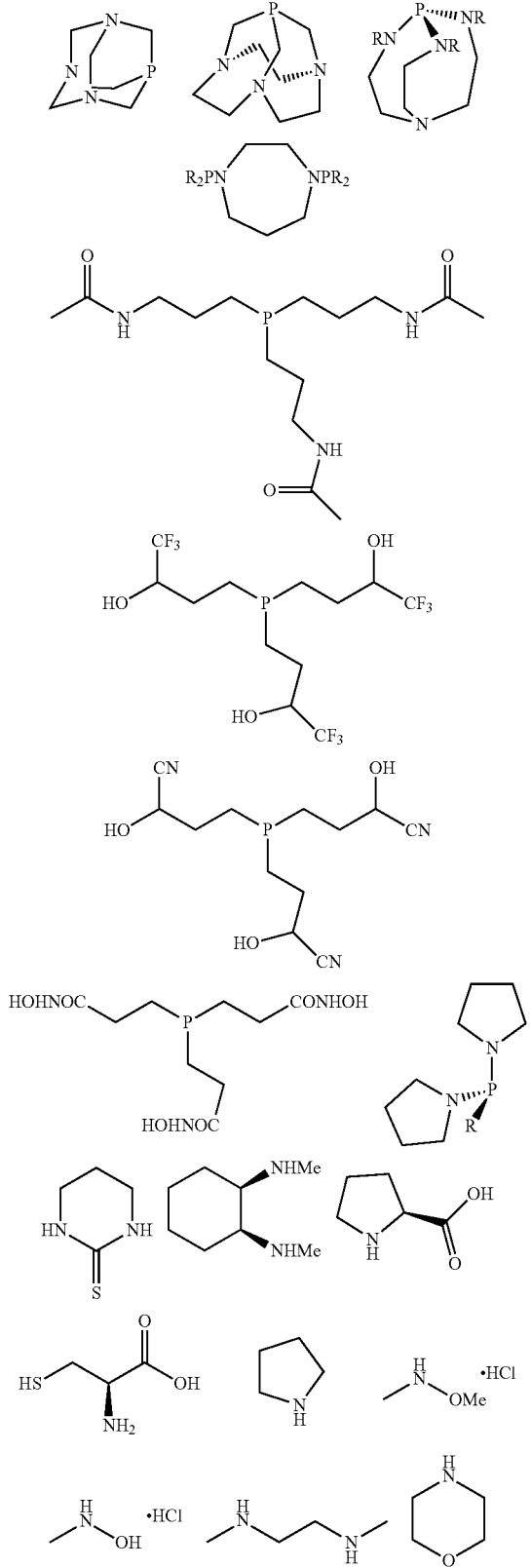

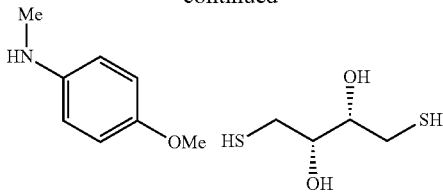

In the structures above, each R group is independently hydrogen or a substituted or unsubstituted alkyl group (e.g., methyl, ethyl, or isopropyl).

In some cases, the blocking group is removed by washing the blocking group from the incorporated nucleotide analogue using a reducing agent such as a phosphine reagent. In some cases, the blocking group is photolabile, and the blocking group can be removed by application of, e.g., UV light. In some cases, the blocking group can be removed by contacting the nucleoside analogue with a transition metal catalyzed reaction using, e.g., an aqueous palladium (Pd) solution. In some cases, the blocking group can be removed by contacting the nucleoside analogue with an aqueous nitrite solution. Additionally, or alternatively, the blocking group can be removed by changing the pH of the solution or mixture containing the incorporated nucleotide analogue. For example, in some cases, the blocking group can be removed by contacting the nucleoside analogue with acid or a low pH (e.g., less than 4) buffered aqueous solution.

In some cases, the blocking group can be removed by use of a strongly electronegative or strongly basic solution. For example, in some cases, the 3'-O reversible blocking groups that can be cleaved by a fluoride or hydroxide containing solution. 3'-O reversible blocking groups that can be cleaved by contacting with a hydroxide or fluoride containing solution include, but are not limited to, allenyl, cyanoethyl, cyanoethenyl, formaldehyde oximyl, acrylaldehyde oximyl, propionaldehyde oximyl, and cyanoethenaldehyde oximyl blocking groups or blocking groups that contain an allenyl, cyanoethyl, cyanoethenyl, formaldehyde oximyl, acrylaldehyde oximyl, propionaldehyde oximyl, or cyanoethenaldehyde oximyl moiety.

In some cases, the 3'-O reversible blocking group (e.g., allenyl, cyanoethyl, cyanoethenyl, formaldehyde oximyl, acrylaldehyde oximyl, propionaldehyde oximyl, or cyanoethenaldehyde oximyl) can be cleaved by contacting with a nucleophile or base containing solution. In some cases, an allenyl or allenyl containing 3'-O reversible blocking group can be cleaved by contacting with a nucleophile or base containing solution. In some cases, a cyanoethyl or cyanoethyl containing 3'-O reversible blocking group can be cleaved by contacting with a nucleophile or base containing solution. In some cases, a cyanoethenyl or cyanoethenyl containing 3'-O reversible blocking group can be cleaved by contacting with a nucleophile or base containing solution. In some cases, a formaldehyde oximyl or formaldehyde oximyl containing 3'-O reversible blocking group can be cleaved by contacting with a nucleophile or base containing solution. In some cases, an acrylaldehyde oximyl or acrylaldehyde oximyl containing 3'-O reversible blocking group can be cleaved by contacting with a nucleophile or base containing solution. In some cases, a propionaldehyde oximyl or propionaldehyde oximyl containing 3'-O reversible blocking group can be cleaved by contacting with a nucleophile or base containing solution. In some cases, a cyanoethenaldehyde oximyl or cyanoethenaldehyde oximyl containing 3'-O reversible blocking group can be cleaved by contacting with a nucleophile or base containing solution.

Exemplary nucleophile or base containing solutions for cleavage include, but are not limited to solutions having one or more of dimethylamine, diethylamine, N,N'-dimethylene diamine, methylhydroxyl amine, morpholine, 4-methoxy-N-methylaniline, dithiothreitol, N,N'-dimethyl-cis-cyclohexane-1,2-diamine, proline (e.g., L-proline), pyrrolidine, cysteine (e.g., L-cysteine), thiosulfate (e.g., sodium thiosulfate), tetrahydropyrimidine-2(1H)-thione, dicyanomethane carbanion, nitro(4-(trifluoromethyl)phenyl)methanide, nitroethane carbanion (e.g., nitroethane), azide (e.g., sodium azide), sulfite (e.g., sodium sulfite), $NH_2OH$, imidazole, cyclic thiourea, N,O-dimethylhydroxylamine, malononitrile,

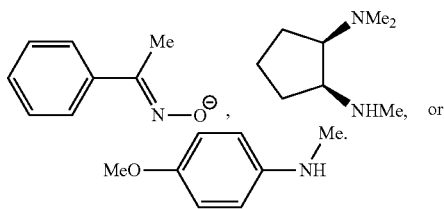

In an exemplary embodiment, 3'-O reversible blocking group (e.g., cyanoethenyl) cleavage conditions are 10-40 equivalents of a nucleophile or base containing solution such as dimethylamine in acetonitrile/0.1 M TEAB for 5-90 minutes. In some cases, 10 equivalents of dimethylamine in acetonitrile/0.1 M TEAB provides complete cleavage after about 30 minutes. In some cases, 40 equivalents of dimethylamine in acetonitrile/0.1 M TEAB provides complete cleavage after about 10 minutes.

In some aspects, the nucleoside analogue contains a 3'-O reversible blocking group and a linker between the nucleobase and an affinity tag or detectable label. In such cases, it can be advantageous to cleave the linker and thereby remove the affinity tag or detectable label from the nucleobase. In some embodiments, the cleavage is performed under the same conditions as the cleavage of the 3'-O reversible blocking group, providing simultaneous cleavage of blocking group and label or affinity tag. Simultaneous cleavage can be used to reduce the number of processing steps required during multiple rounds of nucleoside incorporation, detection, and cleavage. Alternatively, the cleavage can be performed under orthogonal conditions. Orthogonal cleavage can be used to control the relative order in which the nucleoside analogue is unblocked and label or labeled affinity agent is removed. The cleavage can be performed according to any of the methods described above for cleavable linkers, including chemical or enzymatic methods. For example, cleavage can be performed by acid treatment, base treatment, oxidation, reduction, hydrolysis, or by photobleaching. Optionally, cleavage can be performed using phosphine-containing compounds or systems (e.g., phosphine-based transition metal catalysts or water-soluble phosphines). In some cases, the label or labeled affinity agent is removed by linker cleavage prior to cleavage of reversible blocking group. In some cases, the label or labeled affinity agent is removed by linker cleavage before cleavage of reversible blocking group.

Detection is generally performed prior to linker cleavage, if linker cleavage is employed. However, detection can be performed before or after reversible blocking group cleavage. Moreover, in some embodiments, although the nucleoside analogue can contain a group comprising a nucleobase that is covalently linked to a cleavable linker (which in turn is covalently linked to a detectable label or affinity tag), cleavage of the linker is not universally employed or required for performing additional cycles of sequencing-by-synthesis or sequencing-by-ligation. For example, detectable label covalently linked to the linker or detectably labeled affinity agent can be quenched in lieu of, or in addition to, linker cleavage. Additionally, or alternatively, detectably labeled affinity agent can be stripped from the affinity agent.

Sequencing

The nucleoside analogues described herein can be used in a variety of sequencing methods. For example, the analogues can be used in no-label, 2-label, 3-label, or 4-label sequencing methods. Exemplary no-label sequencing methods include, but are not limited to, methods in which nucleoside analogues having different nucleobases (e.g., A, C, G, T) are delivered in succession and incorporation is detected be detecting the presence or absence of the same signal or label for each different nucleobase. Thus, no-label methods are sometimes known as one-label, or one-color methods because the detection signal and/or label is the same for all nucleobases. For example, incorporation of a nucleoside into a primer by DNA polymerase mediated template directed polymerization can be detected by detecting a pyrophosphate cleaved from the nucleoside pyrophosphate. Pyrophosphate can be detected using a coupled assay in which ATP sulfurylase converts pyrophosphate to ATP, in the presence of adenosine 5' phosphosulfate, which in turn acts as a substrate for luciferase-mediated conversion of luciferin to oxyluciferin, generating visible light in amounts proportional to ATP generation.

In an alternative no-label system, an inducer that is released by polymerase-mediated cleavage between alpha and beta phosphate of a nucleoside analogue, and optionally further processed by a second enzyme such as a phosphatase or sulfurylase, then activates a quenched dye on a capture element. This system, method, and compositions for performing the method, is further described, e.g., in co-pending International Patent Application PCT/US2015/057094, entitled "Signal Confinement Sequencing (SCS) and Nucleotide Analogues for Signal Confinement Sequencing," filed on Oct. 23, 2015, the contents of which are hereby incorporated by reference in their entirety for all purposes.

One of skill in the art will recognize that, although a nucleoside analogue containing a nucleobase-linker moiety attached to a detectable label or affinity agent group is not required for such no-label methods, such nucleoside analogues are compatible with no-label methods in general. As such, no-label sequencing methods can employ any one of the following nucleoside analogues, or mixtures thereof.

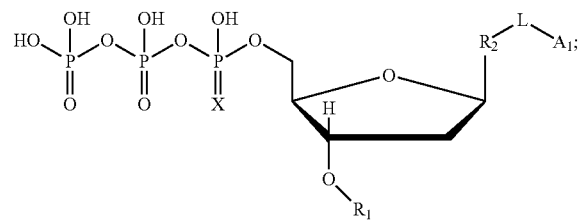

Formula VI

Formula VII

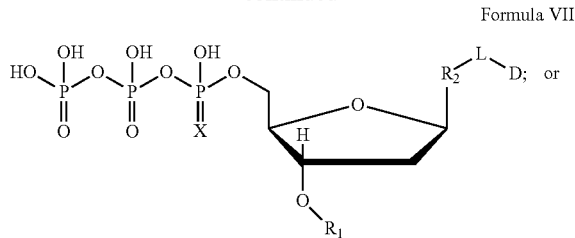

Formula VIII

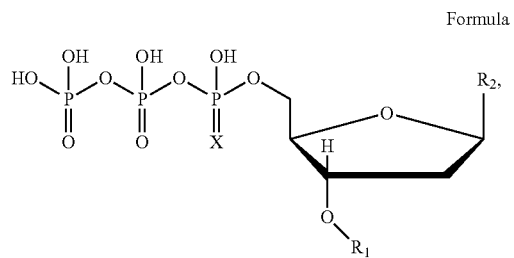

wherein
X is selected from O and S; $R_1$ is or includes a 3'-O reversible blocking group (e.g., allenyl, cyanoethyl, cyanoethenyl, formaldehyde oximyl, acrylaldehyde oximyl, propionaldehyde oximyl, or cyanoethenaldehyde oximyl); $R_2$ is or includes a nucleobase; L is or includes a linker (e.g., a cleavable linker); D is or includes a detectable label (e.g., detectable fluorescent label); and $A_1$ is or includes an affinity tag.

Alternatively, 2-label sequencing can be performed with the nucleoside analogues described herein, using two distinguishable signals in a combinatorial fashion to detect incorporation of four different nucleobases. Exemplary 2-label systems, methods, and compositions include, without limitation, those described in U.S. Pat. No. 8,617,811, the contents of which are hereby incorporated by reference in the entirety for all purposes and particularly for disclosure related to 2-label sequencing. Briefly, in 2-label sequencing, incorporation of a first nucleobase (e.g., A) is detected by detecting the presence of a first label; and, incorporation of a second nucleobase (e.g., C) is detected by detecting the presence of a second label. Incorporation of a third nucleobase (e.g., T) is detected by detecting the presence of both the first and second label attached to the third nucleobase; and, incorporation of a fourth unlabeled nucleobase (e.g., G) is detected by detecting the absence of both first and second labels. The labels of the nucleoside analogues utilized in a 2-label sequencing method can be attached to affinity agents specifically bound to affinity tags linked (e.g., cleavably linked) to a nucleobase, or directly attached to via a covalent linker (e.g., cleavable linker) to the nucleobase.

Similarly, 3- and 4-label sequencing can be performed with the nucleoside analogues described herein, using three or four distinguishable signals to detect incorporation of four different nucleobases. For example, 3-label sequencing can employ a first nucleobase labeled with a first label, a second nucleobase labeled with a second label, a third nucleobase labeled with a third label, and a fourth nucleobase that is either not labeled or labeled with a combination of first and second, first and third, or second and third labels. The labels of the nucleoside analogues utilized in a 3-label sequencing method can be attached to affinity agents specifically bound to affinity tags that are in turn linked (e.g., cleavably linked) to a nucleobase, or directly attached to via a covalent linker (e.g., cleavable linker) to the nucleobase. Similarly, 4-label sequencing can employ a first nucleobase labeled with a first label, a second nucleobase labeled with a second label, a third nucleobase labeled with a third label, and a fourth nucleobase labeled with a fourth label. The labels of the nucleoside analogues utilized in a 4-label sequencing method can be attached to affinity agents specifically bound to affinity tags that are in turn linked (e.g., cleavably linked) to a nucleobase, or directly attached to via a covalent linker (e.g., cleavable linker) to the nucleobase.

Such 2-, 3-, and 4-label, also referred to as 2-, 3-, and 4-color, sequencing methods can be used in both sequencing by synthesis and sequencing by ligation. For example, nucleoside analogues of Formulas VI or VII can be utilized for sequencing by synthesis in a 2-, 3-, or 4-label method. Similarly, oligonucleotides containing nucleoside analogues of the following formulas can be used for sequencing by ligation in a 2-, 3-, or 4-label method:

Formula IX

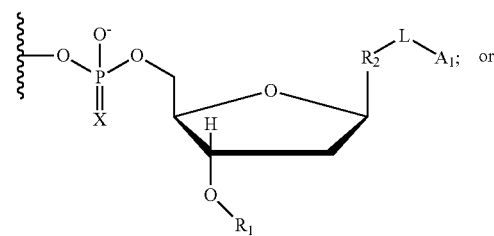

Formula X

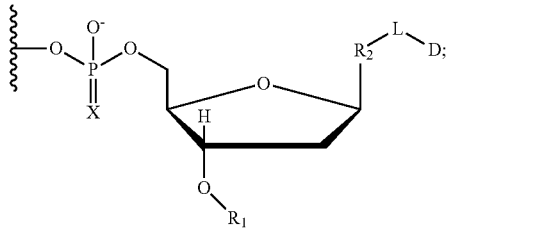

wherein X is selected from S and O; $R_1$ is or contains a 3'-O reversible blocking group selected from allenyl, cyanoethyl, cyanoethenyl, formaldehyde oximyl, acrylaldehyde oximyl, propionaldehyde oximyl, and cyanoethenaldehyde oximyl; $R_2$ is or includes a nucleobase; L is or includes a linker; D is or includes a detectable label (e.g., a detectable fluorescent label); and $A_1$ is or includes an affinity tag.

Various sequencing by synthesis and sequencing by ligation methods can be used with the nucleoside analogues of the present invention. In some aspects, the sequencing by synthesis methods can be selected from those described in U.S. Pat. Nos. 6,210,891; 6,828,100, 6,833,246; 6,911,345; 6,969,488; 6,897,023; 6,833,246; and 6,787,308; Patent Publication Nos. 2003/0,064,398; and 2003/0,022,207; Margulies et al., 2005, Nature 437:376-380; Ronaghi et al., 1996, Anal. Biochem. 242:84-89; Constans, A, 2003, The Scientist 17(13):36; and Bentley et al., 2008, Nature 456 (7218): 53-59. In some aspects, sequencing by ligation methods can be selected from those described in International Patent Publication WO 1999/019,341; WO 2005/082, 098; WO 2006/073,504; and Shendure et al., 2005, Science, 309: 1728-1739. In an exemplary embodiment, the sequencing by synthesis or sequencing by ligation is performed using one or more nucleoside analogues described herein with a method described in U.S. Provisional Patent Application No. 62/194,741, entitled "DNA Sequencing Using Controlled Strand Displacement," filed on Jul. 20, 2015, the contents of which are hereby incorporated by reference in the entirety for all purposes, and particularly for the template preparation and sequencing methods and compositions described therein.

For example, a DNA strand for sequencing can be produced by a) providing a template DNA polynucleotide containing a first target DNA sequence interposed between a first adaptor 3' to the first target DNA sequence and a second adaptor 5' to the first target DNA sequence, and optionally comprising a third adaptor 3' to the first adaptor and a second target DNA sequence interposed between the first adaptor and the third adaptor, wherein the template DNA polynucleotide is immobilized on a substrate; b) combining a first primer with the immobilized template DNA polynucleotide, and hybridizing the first primer to a first primer binding sequence in the first adaptor, wherein the first primer is not immobilized on the substrate when it is combined with the immobilized template DNA polynucleotide; c) extending the first primer using a first DNA polymerase to generate a second strand, wherein the second strand comprises a sequence complementary to the first target DNA sequence and a sequence complementary to at least part of the second adaptor; d) combining a second primer with the immobilized template DNA polynucleotide, hybridizing a second primer to a second primer binding sequence, wherein the second primer binding sequence is 3' to the first primer binding sequence, wherein the second primer is not immobilized on the substrate when it is combined with the immobilized template DNA polynucleotide; e) extending the second primer using a DNA polymerase having strand-displacement activity to generate a third strand, wherein extending the second primer to generate the third strand partially displaces the second strand, thereby producing a partially hybridized second strand having: (i) a hybridized portion that is hybridized to the template DNA polynucleotide; and (ii) an unhybridized overhang portion that contains a sequence that is complementary to the first target DNA sequence and a sequence that is complementary to at least part of the second adaptor, wherein the unhybridized portion is 5' in the second strand to the hybridized portion.

The prepared template can be then sequenced by, e.g., hybridizing a sequencing oligonucleotide to the sequence in the third strand that is complementary to at least part of the second adaptor. The sequencing oligonucleotide can be an anchor primer for hybridizing to template nucleic acid and ligating to an adjacent hybridized oligonucleotide containing a nucleoside analogue described herein. Thus, the method can be used for sequencing by ligation. Alternatively, the sequencing oligonucleotide can be a polymerase primer that is extended by incorporating a nucleoside analogue described herein. Thus, the method can be used for sequencing by synthesis.

EXAMPLES

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

Example 1: Synthesis of Nucleoside Analogues

General Procedure for the Preparation of 3'-O-Cyanoethenyl-Thymidine Triphosphate Treatment of 5'-O-TBDMS-thymidine (1) with formic acid, using EDCI as the coupling reagent, gave 346 mg of 5'-O-TBDMS-3'-O-formyl-thymidine (6) in 64% yield. Wittig reaction between the formate ester (6) and (triphenylphosphoranylidene)acetonitrile in refluxing toluene afforded a 5 to 1 mixture of trans/cis 5'-O-TBDMS-3'-O-cyanoethenyl-thymidine (7) (trans shown for simplicity) in good yield.

The isomers were readily separated by column chromatography. A 257 mg quantity (58% yield) of the trans-isomer (7) was isolated. Deprotection of trans-isomer (7) with TBAF gave 143 mg of 3'-O-cyanoethenyl-thymidine (8) (>99% pure by HPLC) in good yield. Synthesis of a second batch of 3'-O-cyanoethenyl-thymidine (8) was successfully completed to give a further 90 mg quantity (>99% pure by HPLC). Phosphorylation of 3'-O-cyanoethenyl-thymidine (8) (50 mg scale) gave impure triphosphate and this was purified to give 14 mg of 3'-O-cyanoethenyl-thymidine triphosphate (9) at >99% purity by HPLC. The $^1$H-NMR, MS and $^{31}$P-NMR spectral data confirmed the structure.

Scheme:

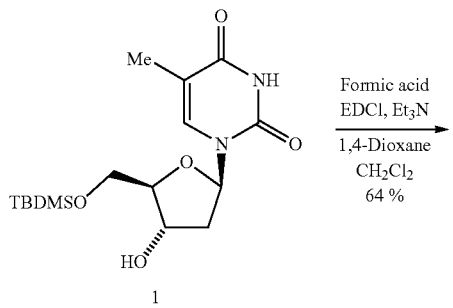

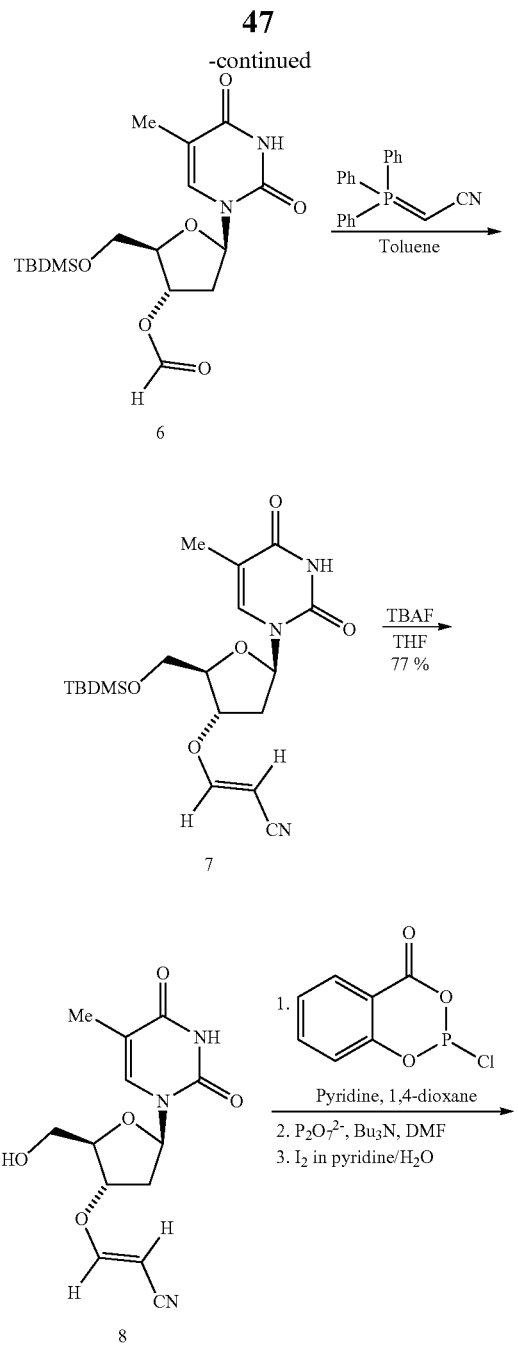

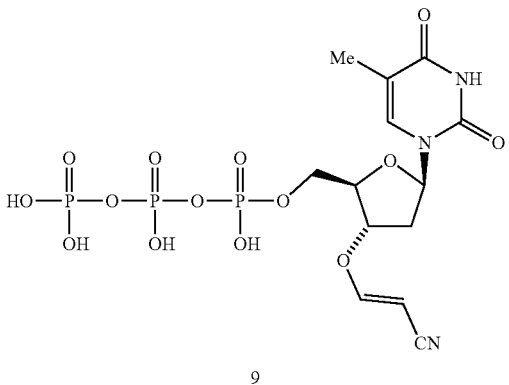

General Procedure for the Preparation of 3'-O-cyanoethenyl-5-Rox-1-amino-11,19-dioxo-3,6,9,14,17-pentaoxa-2-azatricos-12-en-22-yn-23-yl)-uridine triphosphate To a solution of linker-ROX (3 μmol) in DMF (0.5 mL) was added TSTU (6 μmol) and DIEA (6 μmol). After 20 minutes, LCMS indicated the complete formation of NHS ester. The reaction mixture in DMF was poured into 10 ml ethyl acetate-isopropanol (4:1 volume ratio) to precipitate the NHS ester. The precipitate was centrifuged, and quickly washed with 2 mL ethyl acetate-isopropanol by centrifuge and decant. The precipitate was dried under vacuum to remove solvent. The precipitate was dissolved in 0.2 mL anhydrous DMF. The resulting product was ready for coupling. To a solution of 3'-O-cyanoethenyl-dTTP-propargylamine (1.5 mg, about 1 μmol) in NaHCO3 buffer (0.1 mL, pH 8.7, 50 mM, cold on ice) was added dropwise with stirring the DMF solution of NHS ester of linker-ROX prepared above. The final reaction mixture was the stirred on ice and then kept in a fridge overnight with exclusion of light. LCMS monitoring indicated the formation of desired product. The reaction mixture was directly purified by reverse-phase prep-HPLC (C18, solvent A: 20 mM TEAB in water, solvent B: 20 mM TEAB in MeCN, 5% to 100%) to afford the final product, characterized by LC-MS, H NMR, and P NMR.

Scheme:

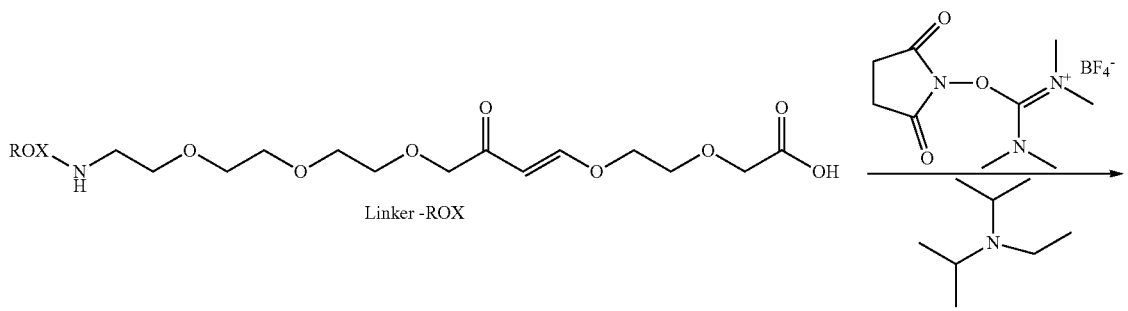

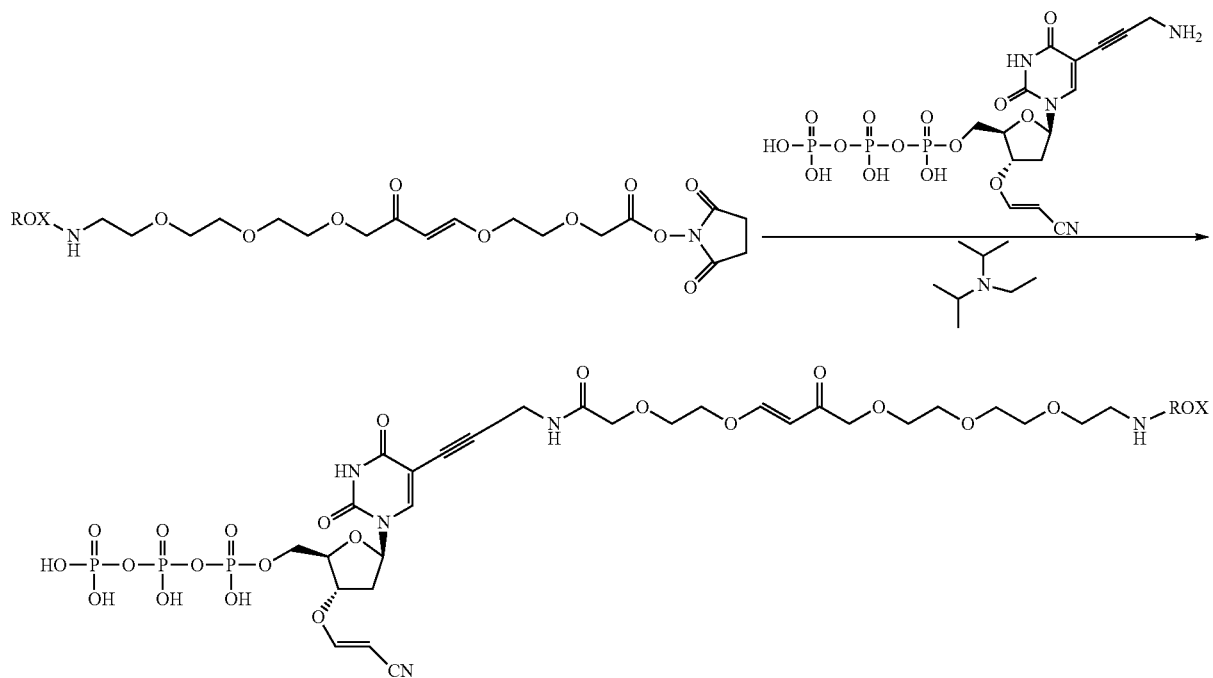

General Procedure for the Preparation of 3'-O-allenyl-thymidine triphosphate Reaction of 5'-O-TBDMS-thymidine (1) with sodium hydride followed by propargyl bromide gave 365 mg of 5'-O-TBDMS-3'-O-propargyl-thymidine (2). Reaction of (2) with potassium tert-butoxide afforded 3'-O-allenyl-thymidine (4) in acceptable yield considering that the TBDMS was also cleaved using these reaction conditions. A total of 111 mg of impure 3'-O-allenyl-thymidine (4) was prepared and after two purifications 46 mg of (4) was obtained with purity >95% by HPLC. Phosphorylation of 3'-O-allenyl-thymidine (8) (23 mg scale) was carried out using our standard conditions. After purification by semi-prep HPLC and freeze drying, formation of thymidine triphosphate was observed by HPLC (2.8%). And after a second freeze-drying, 7% thymidine triphosphate was observed. A 4 mg quantity of 3'-O-allenyl-thymidine triphosphate (90.1% purity by HPLC) containing 7% of thymidine triphosphate was obtained.

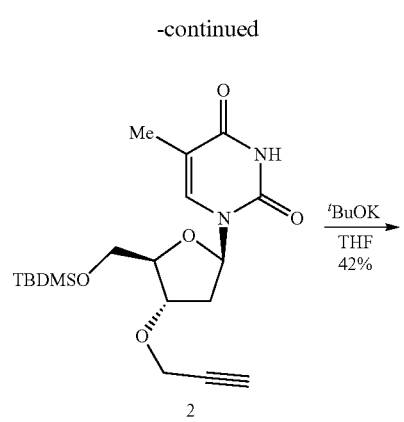

Scheme:

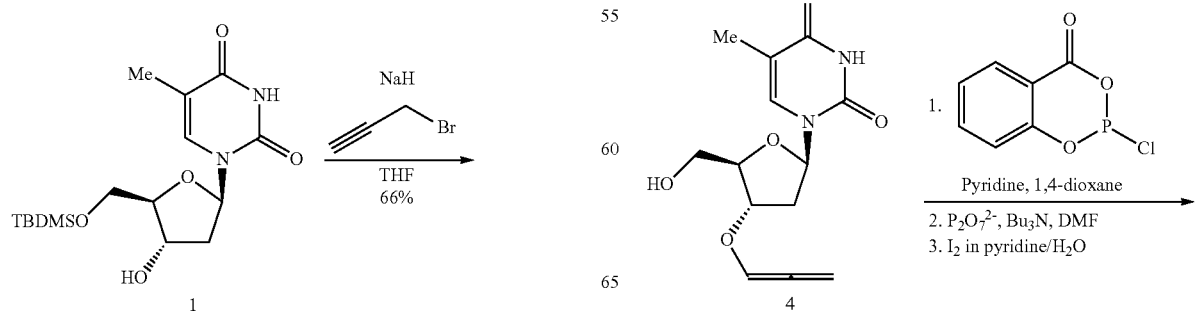

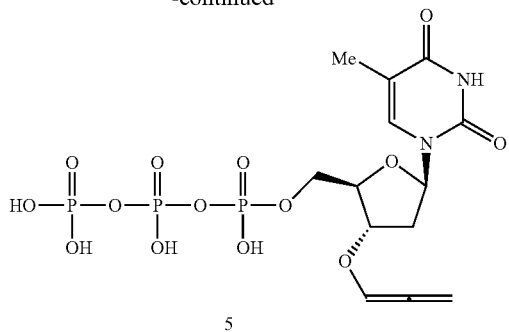

General Procedure for the Preparation of 3'-O-allenyl-5-Rox-1-amino-11,19-dioxo-3,6,9,14,17-pentaoxa-20-azatricos-12-en-22-yn-23-yl)-uridine triphosphate To a solution of linker-ROX (3 µmol) in DMF (0.5 mL) was added TSTU (6 µmol) and DIEA (6 µmol). After 20 minutes, LCMS indicated the complete formation of NHS ester. The reaction mixture in DMF was poured into 10 ml ethyl acetate-isopropanol (4:1 volume ratio) to precipitate the NHS ester. The precipitate was centrifuged, and quickly washed with 2 mL ethyl acetate-isopropanol by centrifuge and decant. The precipitate was dried under vacuum to remove solvent. The precipitate was dissolved in 0.2 ml anhydrous DMF. The resulting product was ready for coupling. To a solution of 3'-O-allenyl-dTTP-propargylamine (1.5 mg, about 1 µmol) in NaHCO3 buffer (0.1 mL, pH 8.7, 50 mM, cold on ice) was added dropwise with stirring the DMF solution of NHS ester of linker-ROX prepared above. The final reaction mixture was the stirred on ice and then kept in a fridge overnight with exclusion of light. LCMS monitoring indicated the formation of desired product. The reaction mixture was directly purified by reverse-phase prep-HPLC (C18, solvent A: 20 mM TEAB in water, solvent B: 20 mM TEAB in MeCN, 5% to 100%) to afford the final product, characterized by LC-MS, H NMR, and P NMR.

Scheme:

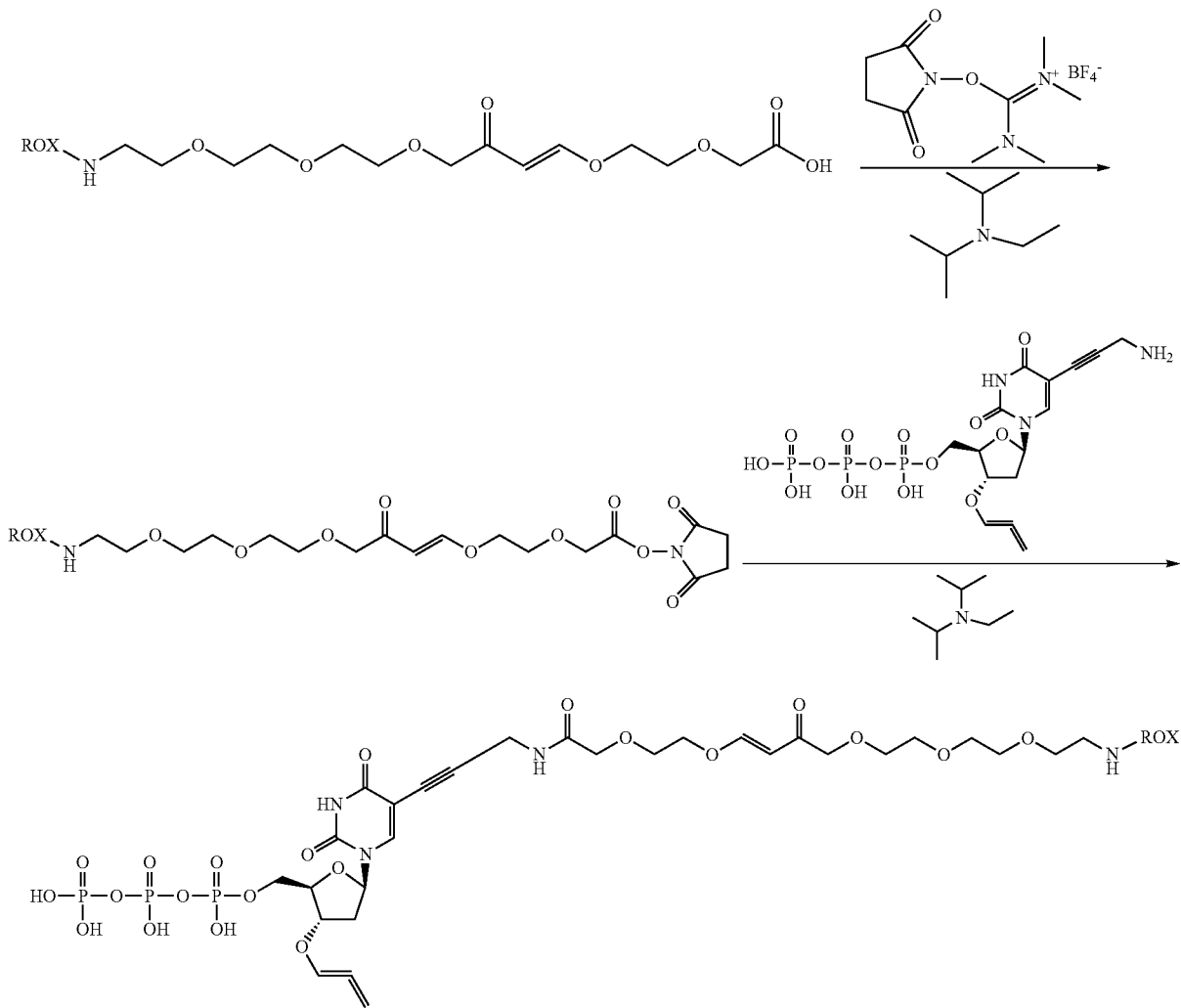

General Procedure for the Preparation of 3'-O-formaldehyde oximyl-5-Rox-2-amino-11,19-dioxo-3,6,9,14,17-pentaoxa-20-azatricos-12-en-22-yn-23-yl)-uridine triphosphate To a solution of linker-ROX (3 µmol) in DMF (0.5 mL) was added TSTU (6 µmol) and DIEA (6 µmol). After 20 minutes, LCMS indicated the complete formation of NHS ester. The reaction mixture in DMF was poured into 10 ml ethyl acetate-isopropanol (4:1 volume ratio) to precipitate the NHS ester. The precipitate was centrifuged, and quickly washed with 2 mL ethyl acetate-isopropanol by centrifuge and decant. The precipitate was dried under vacuum to remove solvent. The precipitate was dissolved in 0.2 mL anhydrous DMF. The resulting product was ready for coupling. To a solution of 3'-O-formaldehyde oximyl-dTTP-propargylamine (1.5 mg about 1 µmol) in NaHCO3 buffer (0.1 mL, pH 8.7, 50 mM, cold on ice) was added dropwise with stirring the DMF solution of NHS ester of linker-ROX prepared above. The final reaction mixture was the stirred on ice and then kept in a fridge overnight with exclusion of light. LCMS monitoring indicated the formation of desired product. The reaction mixture was directly purified by reverse-phase prep-HPLC (C18, solvent A: 20 mM TEAB in water, solvent B: 20 mM TEAB in MeCN, 5% to 100%) to afford the final product, characterized by LC-MS, H NMR, and P NMR.

Example 2: Monitoring Cleavage of 3'-O Reversible Blocker

Cleavage reactions were performed using 5 mg of compound 8 (3'-O-cyanoethyenyl-thymidine) in 0.25 mL of acetonitrile and 0.25 mL of buffer. Cleavage was monitored by LC-MS and the results are depicted in the table below.

| Entry | Nucleophile (equivalents) | Buffer | Reaction progress (monitored by LCMS) Ratio starting material:Thymidine | | | |
|---|---|---|---|---|---|---|
| | | | 10 min | 20 min | 30 min | 60 min |
| 1 | Dimethylamine (10 equivalents) | 0.1M TEAB (pH = 8.2) | 50:50 | 5:95 | 0:100 | N/A |
| 2 | Dimethylamine (40 equivalents) | 0.1M TEAB (pH = 8.2) | 0:100 | N/A | N/A | N/A |
| 3 | Dimethylamine (40 equivalents) | 1M Tris-buffer (pH = 8.1) | 0:100 | N/A | N/A | N/A |
| 4 | Dimethylamine (40 equivalents) | 0.5M Phosphate buffer (pH = 7.5) | 10:90 | 0:100 | N/A | N/A |

As indicated in the table above, complete cleavage can be achieved in about 20-30 minutes with 10 equivalents of dimethylamine in acetonitrile/0.1 M TEAB. Complete cleavage can be achieved in a about 10 minutes or less with Scheme:

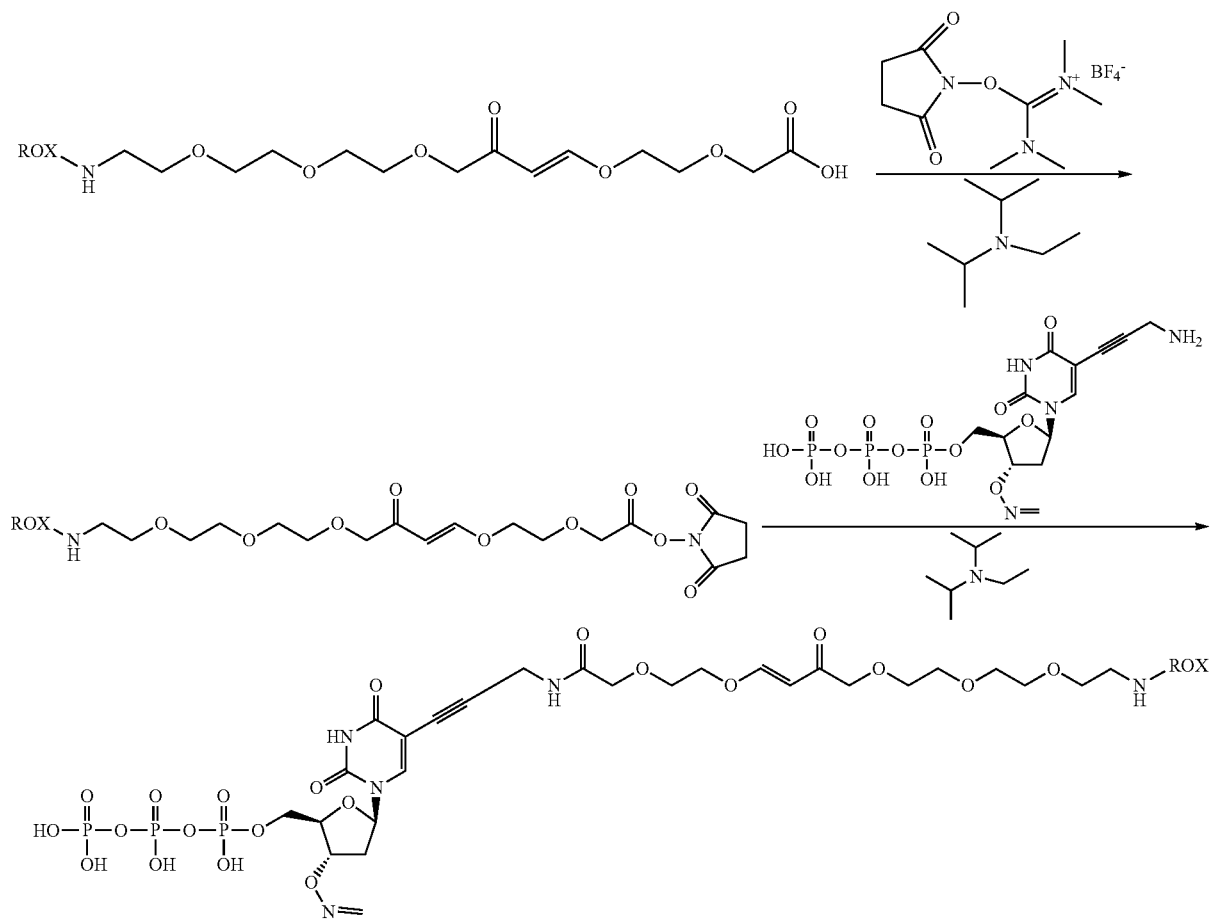

40 equivalents of dimethylamine in acetonitrile/0.1 M TEAB or acetonitrile/1 M Tris buffer. Complete cleavage can be achieved in about 10-20 minutes with 40 equivalents of dimethylamine in acetonitrile/0.5 M phosphate buffer.

Scheme:

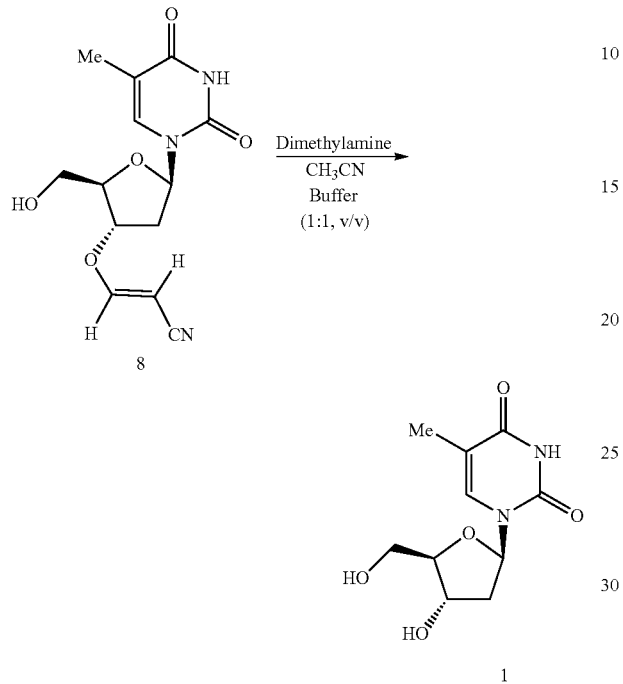

Example 3: Use of Nucleoside Analogues for Sequencing

Allenyl-dTTP and cyanoethenyl-dTTP were incubated at room temperature for 24 hours, or 65° C. for 2 hours. Fresh mixes were also made the day of the experiment. Allenyl-dTTP or cyanoethenyl-dTTP were mixed with unlabeled AGC (AGC-Cold) and used as both the hot (labeled) and cold (unlabeled) chase. Nanoball arrays were imaged to obtain a control image. Then, the array was incubated with labeled mixes to check for incorporation on unblocked ends. The results depicted in FIG. 1 show that both allenyl-dTTP and cyanoethenyl-dTTP are as effective a polymerase substrate for sequencing by synthesis as the unlabeled control 3'-O-azidomethyl-dTTP. Moreover, both allenyl-dTTP and cyanoethenyl-dTTP are stable at room temperature for 24 hours and 65° C. for 2 hours as indicated by their ability to efficiently incorporate into polymerization product and thereby block subsequent polymerization and incorporation of the hot chase label.

Example 4: Synthesis of 3'-O-Cyanoethyenyl-dTTP-Linker-ROX

Materials and Methods

Chemicals were purchased from Aldrich Chemical Company (Gillingham, Dorset), Alfa Aesar (Heysham, Morecambe, Lancashire) and Carbosynth Limited (Compton, Berkshire), unless otherwise noted, and were used without further purification. Solvents were purchased as anhydrous. Petrol was the fraction boiling between 40-60° C. TLC was carried out using aluminium plates pre-coated with silica gel (Kieselgel 60 $F_{254}$, 0.2 mm, Merck, Darmstadt, Germany). Visualization was by UV light. $^1$H NMR spectra were recorded on either a Bruker 300 MHz or 400 MHz spectrometer using the residual proton(s) in the deuterated solvents as internal standards. HPLC analyses were performed on a Shimadzu Prominence instrument with diode array detection. LCMS analyses were performed on a Shimadzu 2010EV instrument operating in positive or negative electrospray (ESI) mode. Automated chromatography was performed on a Biotage Isolera purification system.

5'-O-(tert-Butyldimethylsilyl)-2'-deoxy-5-iodouridine

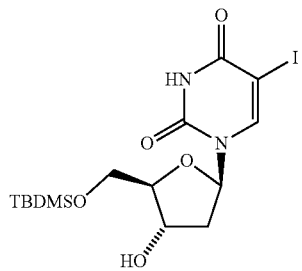 [SMILES: CC(C)(C)[Si](C)(C)OC[C@H]1O[C@@H](n2cc(I)c(=O)[nH]c2=O)C[C@@H]1O]

To an ice-cold solution of 2'-deoxy-5-iodouridine (1.00 g, 2.82 mmol), imidazole (0.58 g, 8.47 mmol), and 4-(dimethylamino)pyridine (34.5 mg, 0.28 mmol) in anhydrous DMF (13 mL) was added tert-butyldimethylsilyl chloride (0.51 g, 3.39 mmol) portionwise and the mixture was stirred for 40 minutes before allowing it to warm slowly to room temperature overnight. The resulting mixture was quenched with saturated aqueous ammonium chloride solution (50 mL) and diluted with ethyl acetate (40 mL). The layers were separated and the aqueous layer was extracted with ethyl acetate (2×40 mL). The combined organic extracts were washed with water (5×60 mL) and saturated brine (60 mL), dried over $MgSO_4$, and concentrated to give a colorless oil. This residual material was purified using a Biotage Isolera automated chromatography system under normal phase conditions (silica column, gradient of 10% to 80% ethyl acetate in dichloromethane) with detection at 254 nm to give 5'-O-(tert-butyldimethylsilyl)-2'-deoxy-5-iodouridine (0.91 g, 69%), as a white solid. $R_f$ 0.29 (dichloromethane-ethyl acetate, 6:4, v/v).

5'-O-(tert-Butyldimethylsilyl)-2'-deoxy-5-(N-trifluoroacetyl-3-aminopropynyl)uridine

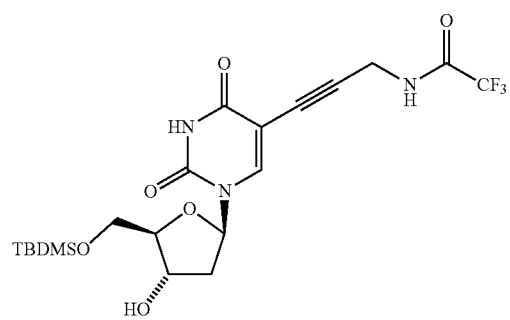 [SMILES: CC(C)(C)[Si](C)(C)OC[C@H]1O[C@@H](n2cc(C#CCNC(=O)C(F)(F)F)c(=O)[nH]c2=O)C[C@@H]1O]

5'-O-(tert-Butyldimethylsilyl)-2'-deoxy-5-iodouridine (0.64 g, 1.36 mmol), copper(I) iodide (52 mg, 0.27 mmol), and tetrakis(triphenylphosphine)palladium(0) (157 mg, 0.14 mmol) were dissolved in anhydrous DMF (7 mL) and the flask was evacuated and purged with nitrogen. Hunig's base (di-isopropylethylamine, 351 mg, 473 μL, 2.71 mmol) and N-trifluoroacetyl-propargylamine (0.62 g, 4.07 mmol) were added and the reaction mixture was stirred at room temperature overnight. The resulting mixture was concentrated under high vacuum and the residue was dissolved in ethyl acetate (30 mL). The organic solution was washed with 5% aqueous EDTA solution (3×15 mL), water (15 mL), and saturated brine (50 mL), dried over $MgSO_4$, and concentrated under reduced pressure to give an orange oil. This residual oil was purified using a Biotage Isolera automated chromatography system under normal phase conditions (silica column, gradient of 12% to 100% ethyl acetate in dichloromethane) with detection at 254 nm to give 5'-O-(tert-butyldimethylsilyl)-2'-deoxy-5-(N-trifluoroacetyl-3-aminopropynyl)uridine (0.65 g, 97%), as a yellow solid. $R_f$ 0.24 (dichloromethane-ethyl acetate, 1:1, v/v).

5'-O-(tert-Butyldimethylsilyl)-2'-deoxy-3'-O-formyl-5-(N-trifluoroacetyl-3-aminopropynyl) uridine

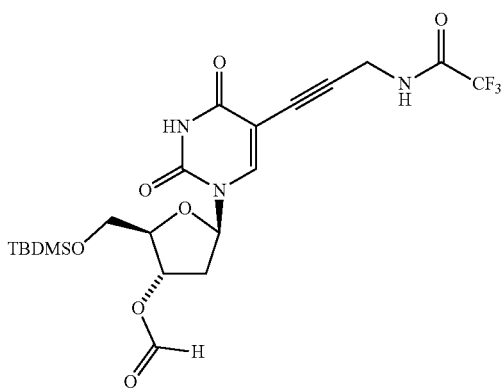 [SMILES: CC(C)(C)[Si](C)(C)OC[C@H]1O[C@@H](n2cc(C#CCNC(=O)C(F)(F)F)c(=O)[nH]c2=O)C[C@@H]1OC=O]

A solution of 5'-O-(tert-butyldimethylsilyl)-2'-deoxy-5-(N-trifluoroacetyl-3-aminopropynyl)uridine (1.00 g, 2.03 mmol), formic acid (187 mg, 154 μL, 4.07 mmol), 4-(dimethylamino)pyridine (25 mg, 0.20 mmol), N-(3-dimethylaminopropyl)-N'-ethylcarbodiimide hydrochloride (0.78 g, 4.07 mmol) and Hunig's base (1.05 g, 1.42 mL, 8.14 mmol in a mixture of dichloromethane (18 mL), and 1,4-dioxane (18 mL) was stirred at room temperature overnight. The reaction mixture was concentrated and the residue was partitioned between 1 M hydrochloric acid (50 mL) and dichloromethane (50 mL). The layers were separated and the aqueous layer was extracted with dichloromethane (2×50 mL). The combined organic extracts were washed with saturated aqueous sodium bicarbonate (50 mL) and then with saturated brine (50 mL), dried over $MgSO_4$, and concentrated under reduced pressure to give a yellow oil. This material was purified using a Biotage Isolera automated chromatography system under normal phase conditions (silica column, gradient of 12% to 100% ethyl acetate in dichloromethane) with detection at 254 nm to give 5'-O-(tert-butyldimethylsilyl)-2'-deoxy-3'-O-formyl-5-(N-trifluoroacetyl-3-aminopropynyl)uridine (0.49 g, 46%), as an off-white solid. $R_f$ 0.55 (dichloromethane-ethyl acetate, 1:1, v/v).

(E)-5'-O-(tert-Butyldimethylsilyl)-3'-O-cyanoethenyl-2'-deoxy-5-(N-trifluoroacetyl-3-amino propynyl)uridine

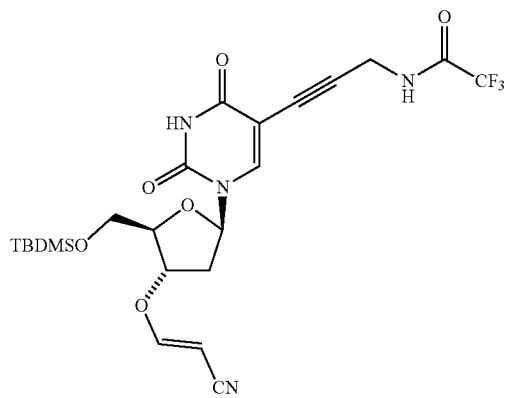 [SMILES: CC(C)(C)[Si](C)(C)OC[C@H]1O[C@@H](n2cc(C#CCNC(=O)C(F)(F)F)c(=O)[nH]c2=O)C[C@@H]1O/C=C/C#N]

A suspension of 5'-O-(tert-butyldimethylsilyl)-2'-deoxy-3'-O-formyl-5-(N-trifluoroacetyl-3-aminopropynyl)uridine (0.44 g, 0.84 mmol) and (triphenylphosphoranylidene)acetonitrile (1.02 g, 3.38 mmol) in toluene (20 mL) in a sealed microwave vial was heated at 115° C. overnight. The orange solution was concentrated under reduced pressure to give a brown solid. This material was purified using a Biotage Isolera automated chromatography system under normal phase conditions (silica column, gradient of 15-100% ethyl acetate in petrol) with detection at 254 nm to give (E)-5'-O-(tert-butyldimethylsilyl)-3'-O-cyanoethenyl-2'-deoxy-5-(N-trifluoroacetyl-3-aminopropynyl) uridine (210 mg, 46%), as an off-white solid. $R_f$ 0.55 (petrol-ethyl acetate, 4:6, v/v).

(E)-3'-O-Cyanoethenyl-2'-deoxy-5-(N-trifluoroacetyl-3-amino propynyl)uridine

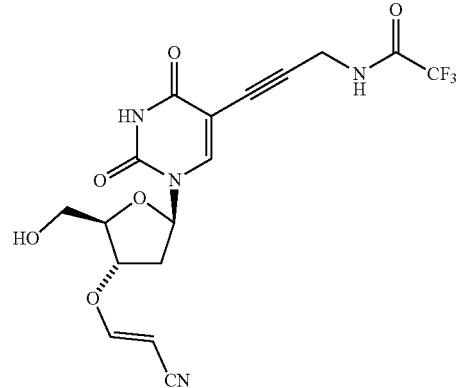 [SMILES: N#C/C=C/O[C@H]1C[C@H](n2cc(C#CCNC(=O)C(F)(F)F)c(=O)[nH]c2=O)O[C@@H]1CO]

To a solution of (E)-5'-O-(tert-butyldimethylsilyl)-3'-O-cyanoethenyl-2'-deoxy-5-(N-trifluoroacetyl-3-aminopropynyl)uridine (210 mg, 0.38 mmol) in anhydrous tetrahydrofuran (6.8 mL) was added a solution of 1 M tetrabutylammonium fluoride in tetrahydrofuran (464 μL, 0.46 mmol) and the mixture was stirred at room temperature for 50 minutes. The resulting orange-red solution was concentrated under reduced pressure to give a dark brown oil.

This residual material was purified using a Biotage Isolera automated chromatography system under normal phase conditions (silica column, gradient of 2% to 20% methanol in dichloromethane) with detection at 254 nm to give (E)-3'-O-cyanoethenyl-2'-deoxy-5-(N-trifluoroacetyl-3-amino propynyl)uridine (98 mg, 59%), as an off-white solid. $R_f$ 0.43 (dichloromethane-methanol, 9:1, v/v).

(E)-5-Aminopropargyl-3'-O-cyanoethenyl-2'-deoxy-dTTP

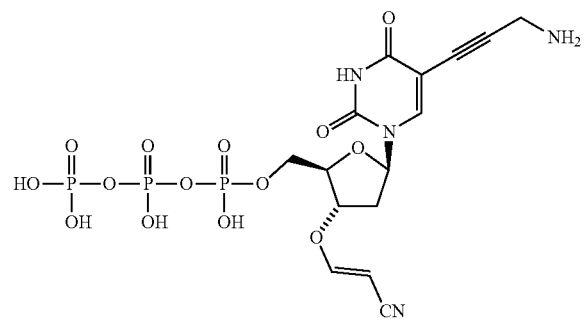 [SMILES: N#C/C=C/O[C@H]1C[C@H](n2cc(C#CCN)c(=O)[nH]c2=O)O[C@@H]1COP(=O)(O)OP(=O)(O)OP(=O)(O)O]

(E)-3'-O-Cyanoethenyl-2'-deoxy-5-(N-trifluoroacetyl-3-aminopropynyl)uridine (40 mg, 0.09 mmol) was dissolved in 1,4-dioxane (0.28 mL) and pyridine (0.11 mL) and the flask was evacuated and purged with] nitrogen. A 1.0 M salicyl chlorophosphite solution in 1,4-dioxane (103 µL, 0.10 mmol) was added and the reaction mixture was stirred for 10 min. A 0.5 M tributylammonium pyrophosphate solution in DMF (0.28 mL, 0.14 mmol) and tributylamine (73 mg, 93 µL, 0.39 mmol) were added and the reaction mixture was stirred for 15 min. A 1% iodine solution in pyridine and water (1.98 mL, 98:2) was added and the solution was stirred for 15 minutes before being quenched with 5% aqueous sodium thiosulfate solution (0.15 mL) and concentrated under reduced pressure. The residual material obtained was purified using a Biotage Isolera automated chromatography system under reversed-phase conditions ($C_{18}$ column, gradient of 0% to 100% acetonitrile in 0.1 M TEAB at pH 7.0) with detection at 254 nm to afford, after lyophilizing, impure (E)-3'-O-cyanoethenyl-2'-deoxy-5-(N-trifluoroacetyl-3-aminopropynyl)dTTP (54 mg). This crude material was purified by semi-preparative HPLC injecting 100 µL portions and collecting the eluent containing the pure substance. The combined fractions were reduced in volume by removing the acetonitrile and most of the water and finally lyophilized to give tri-triethylammonium (E)-3'-O-cyanoethenyl-2'-deoxy-5-(N-trifluoroacetyl-3-aminopropynyl)dTTP (36 mg), as a white solid. The HPLC conditions were as follows: column: ES Industries Sonoma C18 10µ, 15 mm×250 mm; solvent gradient: 89% 0.1 M aqueous TEAB (pH 7) to 87.2% 0.1 M aqueous TEAB (pH 7) over 27 minutes with the balance being acetonitrile; flow rate: 7.8 mL/min; temp: 30° C.; and detection: UV at 315 nm. Under these conditions the product had a retention time of ~21 min.

To a solution of di-triethylammonium (E)-3'-O-cyanoethenyl-2'-deoxy-5-(N-trifluoroacetyl-3-aminopropynyl)dTTP (36 mg) in water was added concentrated ammonia (1.5 mL, 35% in water) and the mixture was stirred at room temperature for 2.5 hours. The resulting material was purified by semi-preparative HPLC, injecting 100 µL portions and collecting the eluent containing the pure substance. The combined fractions were reduced in volume by removing the acetonitrile and most of the water and finally lyophilized to give di-triethylammonium (E)-5-aminopropargyl-3'-O-cyanoethenyl-2'-deoxy-dTTP (17 mg, 24%), as a white solid. The HPLC conditions were as follows: column: Phenomenex Luna C18(2), 15 mm×250 mm; solvent gradient: 94% 0.1 M aqueous TEAB (pH 7) to 93.1% 0.1 M aqueous TEAB (pH 7) over 18 min with the balance being acetonitrile; flow rate: 7.8 mL/min; temp: 30° C.; and detection: UV at 315 nm. Under these conditions the product had a retention time of ~14.5 min.

Di-triethylammonlum 3'-O-cyanoethenyl-dTTP-Linker-ROX

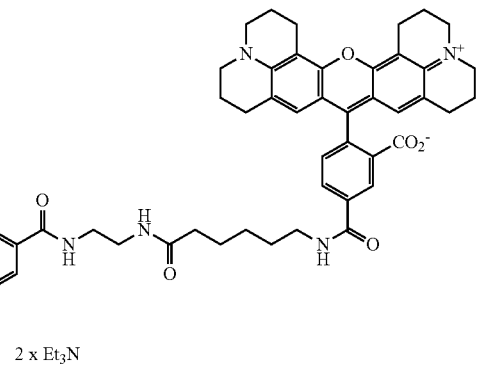

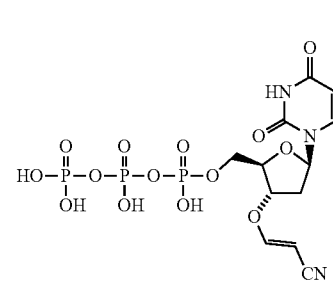

2 x $Et_3N$

To a solution of ROX-linker-OH (10 mg, 0.01 mmol) in DMF (1 mL) was added N,N'-disuccinimidyl carbonate (3.9 mg, 0.015 mmol) and 4-(dimethylamino)pyridine (1.8 mg, 0.015 mmol) and the mixture was stirred at room temperature for 3 hours. After this time, TLC (dichloromethane-methanol, 75:25, v/v) showed the disappearance of the starting material. A solution of di-triethylammonium (E)-5-aminopropargyl-3'-O-cyanoethenyl-2'-deoxy-dTTP (5.4 mg, 0.007 mmol) in 0.1 M TEAB solution at pH=8 was added and the mixture was stirred at room temperature for 3 hours.

The solution was concentrated under reduced pressure to give a purple solid. This material was purified by semi-preparative HPLC injecting 90 μL portions and collecting the eluent containing the pure substance. The combined fractions were reduced in volume by removing the acetonitrile and most of the water and finally lyophilized to give di-triethylammonium 3'-O-cyanoethenyl-dTTP-linker-ROX (6.5 mg, 50%), as a purple solid. The HPLC conditions were as follows: column: ES Industries Sonoma C18 10μ, 15 mm×250 mm; solvent gradient: 90% 0.1 M aqueous TEAB (pH 7) to 60% 0.1 M aqueous TEAB (pH 7) over 24 min with the balance being acetonitrile; flow rate: 7.8 mL/min; temp: 30° C.; and detection: UV at 530 nm. Under these conditions the product had a retention time of ~22.5 min Example 5: Synthesis of Analogues Synthesis of 3'-O-Cyanofluoroethenyl-thymidine Triphosphate 6

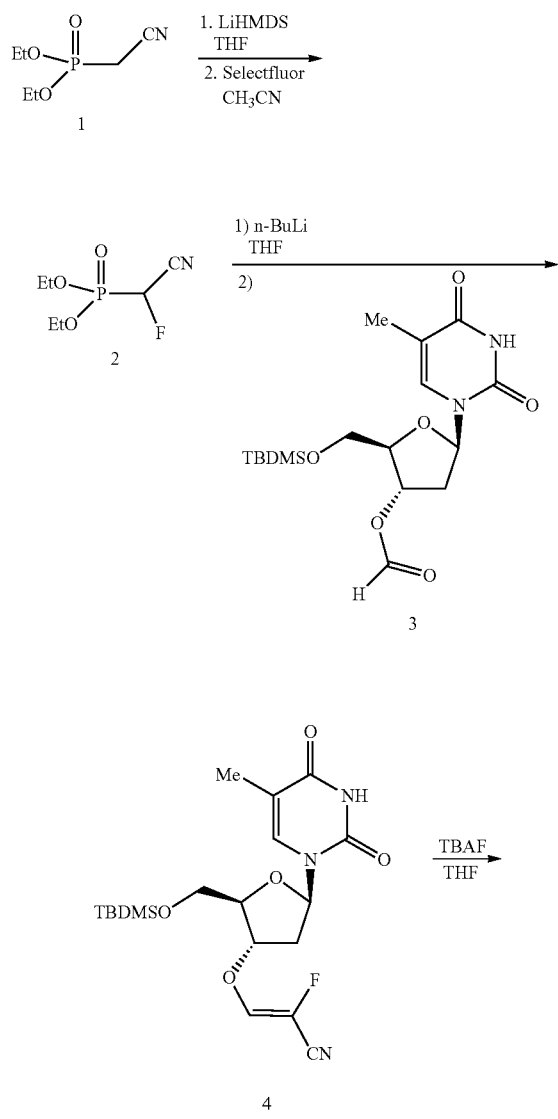

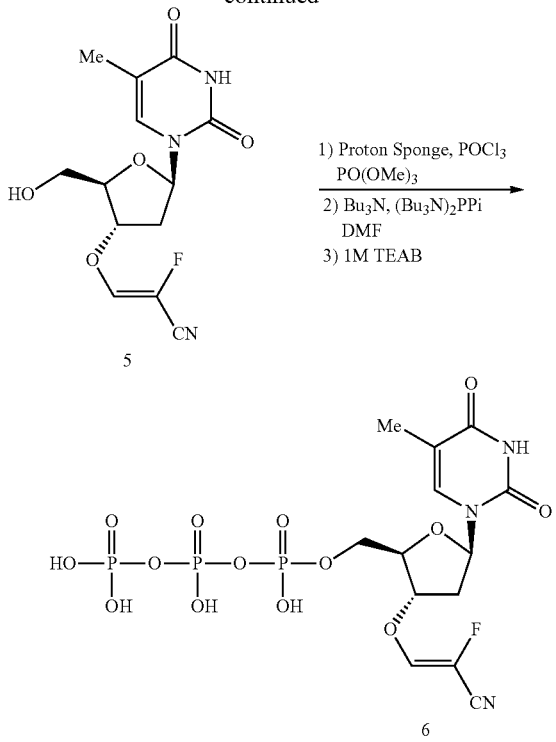

1 to 2: Diethyl (cyanomethyl)phosphonate 1 was dissolved in tetrahydrofuran (THF). LiHMDS (1.2 eq) was added and then the slow addition of a solution of Selecfluor (2 eq) in acetonitrile gave the fluorinated Horner-Wadsworth Emmons reagent 2 in 22% yield after column chromatography.

2 to 4: 2 was dissolved in THF and then BuLi (1.2 eq) was added and stirred for 30 minutes at 0° C. Then, 3'-O-formyl-5'-O-TBDMS-thymidine 3 was added and stirred overnight at room temperature to afford 5'-O-TBDMS-3'-O cyanofluoroethenyl-thymidine 4 in 50% yield (isolated yield) as a cis (JHF=4.1 Hz) and trans (JHF=19.1 Hz) mixture in a 65 to 35 ratio.

4 to 5: To a solution of 4 in anhydrous tetrahydrofuran was added a solution of 1 M tetrabutylammonium fluoride (TBAF) in tetrahydrofuran (1.2 eq) and the mixture was stirred at room temperature for 50 minutes. The resulting solution was concentrated under reduced pressure and was purified by silica column to give 5 in 92% yield.

5 to 6: Nucleoside 5 and proton sponge (2.0 eq) were dissolved in dry acetonitrile (ACN) and rotovaped to dryness to remove H$_2$O. This was repeated 3 times. The mixture was further dried under high vacuum overnight. The mixture was then dissolved in 3 mL PO(OMe)$_3$ under N$_2$. To this solution was added POCl$_3$ (1.5 eq) at 0° C. and stirring was continued for 4 hours at 0° C. In another flask, (Bu$_3$N)$_2$PPi (5 eq) was dissolved in 3 mL dry DMF under N$_2$ and Bu$_3$N (10 eq) was then added. The nucleoside reaction mixture was taken up in a syringe and added to the solution of (Bu$_3$N)$_2$PPi at 0° C. and stirring was continued for 30 minutes at 0° C. The reaction was quenched with 10 mL TEAB (1 M, pH=7.5) at 0° C. and stirring was continued for 1 hour at 0° C. The final reaction mixture was diluted with deionized-H$_2$O loaded on a DEAE column (GE healthcare DEAE Sephadex A-25). The column was eluted with 100 mL deionized-H$_2$O then TEAB solution (0.1 M to 0.2 M to 0.4 M to 0.6 M to 0.8 M). The fractions were collected using UV monitor. The combined fractions were rotovaped or lyophilized to remove the TEAB buffer. The residue was further purified with $C^{18}$ Prep RP-HPLC.

Synthesis of 3'-O-Biscyanoethenyl-thymidine Triphosphate 17

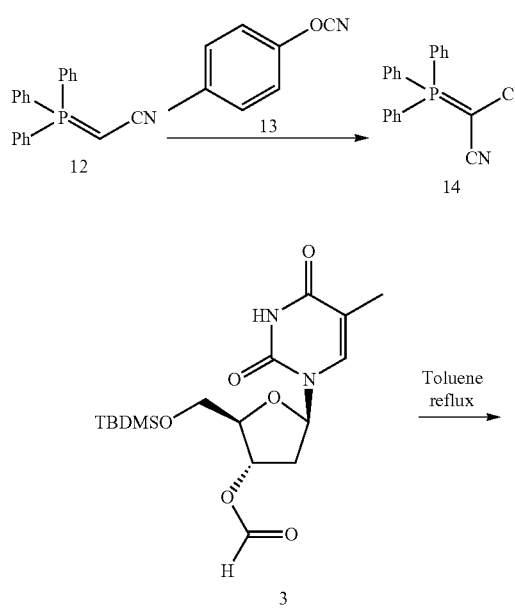

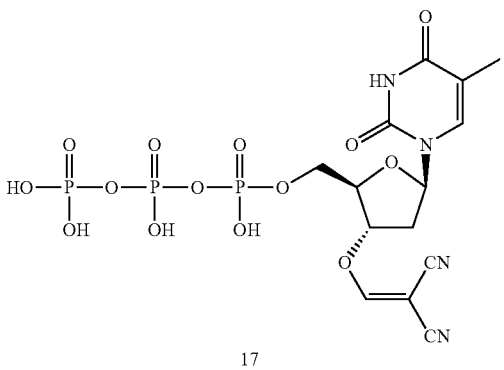

12 to 14: 12 and 13 were mixed to give 14.

14 to 15: A suspension of 3 and 14 (4 eq) in toluene in a sealed microwave vial was heated at 115° C. overnight. The resulted solution was concentrated under reduced pressure and purified by silica column to give 15.

15 to 16: To a solution of 15 in anhydrous tetrahydrofuran was added a solution of 1 M tetrabutylammonium fluoride (TBAF) in tetrahydrofuran (1.2 eq) and the mixture was stirred at room temperature for 50 minutes. The resulting solution was concentrated under reduced pressure and was purified by silica column to give 16.

16 to 17: The same procedure used above for the conversion of 5 to 6 in the synthesis of 3'-O-Cyanofluoroethenyl-thymidine Triphosphate was used.

Synthesis of 3'-O-Propenyl-thymidine Triphosphate 21

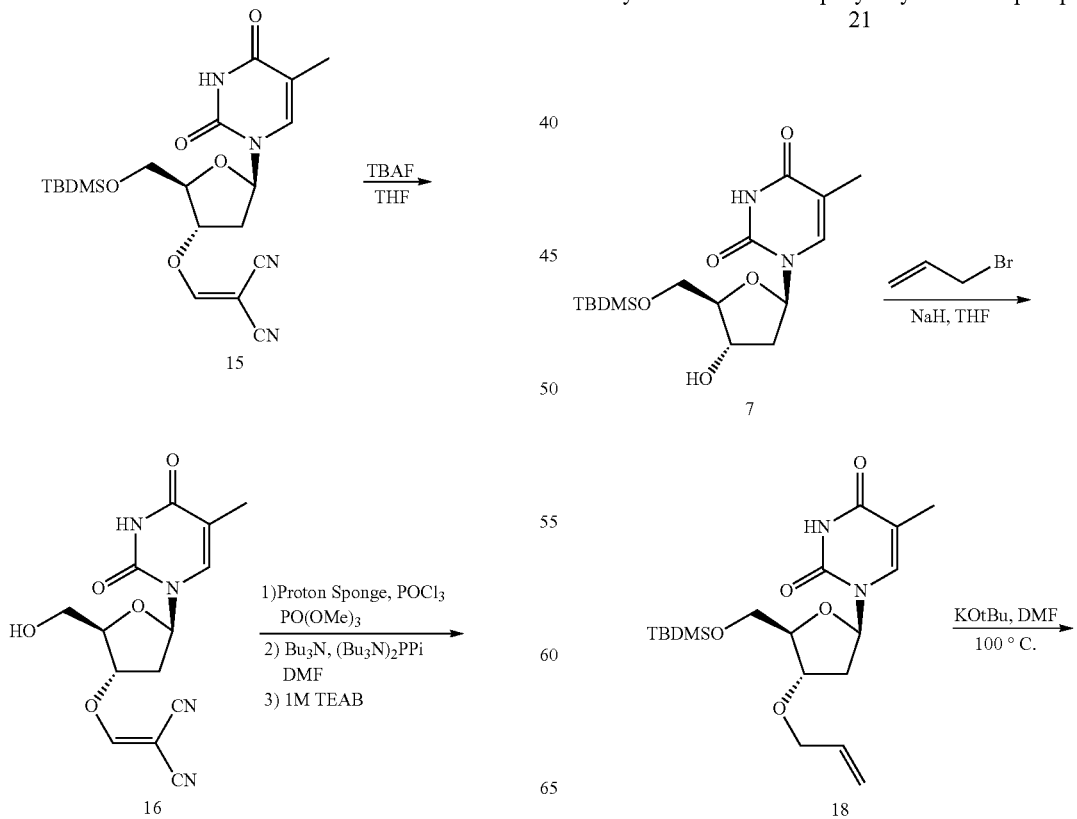

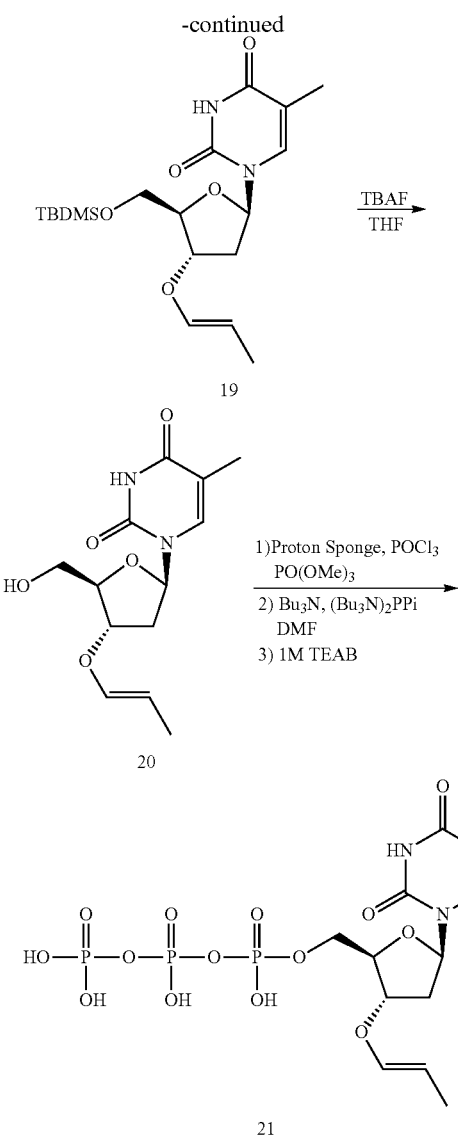

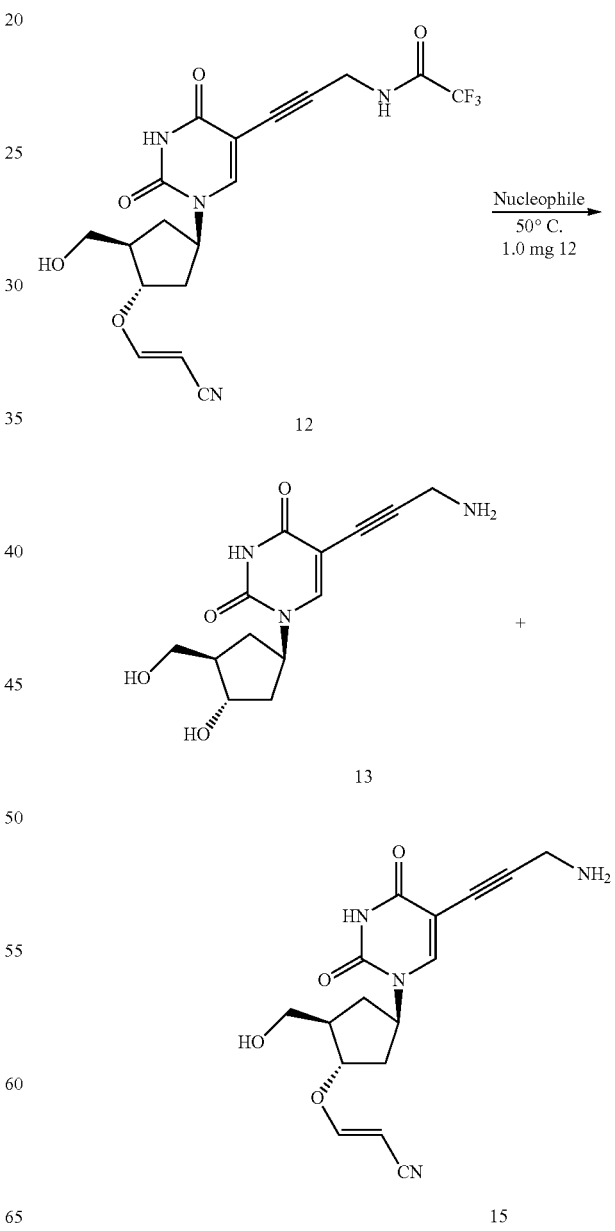

20 to 21: The same procedure used above for the conversion of 5 to 6 in the synthesis of 3'-O-Cyanofluoroethenyl-thymidine Triphosphate was used.

Example 6: Cleavage Studies

Cleavage studies were performed according to the scheme shown below using a variety of nucleophiles. The nucleophiles, concentration, pH, and solvent are indicated for each study. The nucleoside analogue containing a 3'-O-blocking group and a linking group were treated with a nucleophile at 50° C. in solvent to form analogues having both the blocking group and linking group cleaved 13 and only the linking group cleaved 15. The amount of the product obtained after 0.15 hours, 0.5 hours, 1 hour, and 18 hours is indicated in the table. SM indicates starting material.

7 to 18: Thymidine 7 was dissolved in THF and was cooled to 0° C. To the cooled mixture was added NaH (2 eq) and the resulting mixture was stirred at room temperature for 0.5 hours. Then allyl bromide 8 was added at 0° C. and stirred overnight at room temperature. The reaction was quenched with NaHCO$_3$(aq) at 0° C. and extracted with EtOAC. The organic phase was collected and concentrated for purification by silica gel column chromatography to give 18.

18 to 19: 18 was dissolved in DMF and was cooled to 0° C. To the resulting mixture was added 0.2 eq KOtBu and the mixture was stirred at 100° C. overnight. The reaction was cooled and quenched with NaHCO$_3$(aq) at 0° C., and was extracted with EtOAC. The organic phase was collected and concentrated for purification by silica gel column chromatography to give 19.

19 to 20: To a solution of 19 in anhydrous tetrahydrofuran was added a solution of 1 M tetrabutylammonium fluoride (TBAF) in tetrahydrofuran (1.2 eq) and the mixture was stirred at room temperature for 50 minutes. The resulting solution was concentrated under reduced pressure and was purified by silica gel column chromatography to give 20.

Table of Results
(Experimental Conditions: T = 50° C.; 1.0 mg 12/mL solvent).

| Entry | Nucleophile | Concn/M | pH | Solvent | t = 0.15 h | t = 0.5 h | t = 1 h | t = 18 h |
|---|---|---|---|---|---|---|---|---|
| 1 | L-Proline | 1.0 | 6.7 | Water + 20% MeCN | SM | SM | N/A | unidentified species (mass = 299) |
| 2 | L-Proline | 1.0 | 9.0 | Water + 20% MeCN | SM | SM + 5% of unidentified species | SM + 30% of unidentified species | unidentified species as main product (mass = 299) |
| 3 | L-Proline | 5.0 | 9.0 | Water + 20% MeCN | SM + 5% of unidentified species | SM + 15% of unidentified species | 30% SM + multiple peaks | No SM. Two peaks with mass = 299 and 183? |
| 4 | L-Proline | 100 | 9.0 | Water + 20% MeCN | SM + 5% of unidentified species | SM + 15% of unidentified species | 30% SM + multiple peaks | No SM. Two peaks with mass = 299 and 183? |
| 5 | 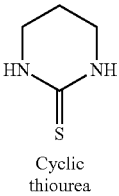 Cyclic thiourea | 1.0 | 7.5 | Water + 20% MeCN | SM | SM | SM | SM |
| 6 | 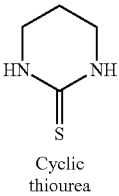 Cyclic thiourea | 1.0 | 7.5 | Water/MeOH 1:1 | SM | SM | SM | SM |
| 7 | L-Cysteine | 1.0 | 7.0 | Water | No SM unidentified species | No SM unidentified species | No SM unidentified species | Product (?) mass = 281 |
| 8 | L-Cysteine | 1.0 | 9.0 | Water | No SM unidentified species | No SM unidentified species | No SM unidentified species | Product (?) mass = 281 |
| 9 | Pyrrolidine | 1.0 | 7.0 | Water | SM | SM | SM + 2% of unidentified species | 15% SM + unidentified species |
| 10 | Pyrrolidine | 1.0 | 9.0 | Water | SM | SM + 15% and 10% of unidentified species | 25% SM + 20%, 25% and 20% of unidentified species | No SM + 80% unidentified species (mass = 299) |
| 11 | Dimethylamine (control) | 40 eq. | 12.0 | Water/MeCN (1:1) | No SM. 1 to1 mixture of 13 and 14 | One peak corresponds to 13 mass = 281 | N/A | N/A |
| 12 | $Na_2S_2O_3$ Thiosulfate | 1.0 | 7.0 | Water + 10% MeCN | SM | SM | N/A | Mixture of SM and 15 (7:3) |
| 13 | $Na_2S_2O_3$ Thiosulfate | 1.0 | 9.0 | Water + 10% MeCN | SM | SM | N/A | Mixture of SM and 15 (8:2) |
| 14 | $Na_2SO_3$ Sodium Sulfite | 1.0 | 7.0 | Water + 10% MeCN | No SM unidentified species | No SM unidentified species | N/A | No SM unidentified species |
| 15 | $Na_2SO_3$ Sodium Sulfite | 1.0 | 9.0 | Water + 10% MeCN | No SM unidentified species | No SM unidentified species | N/A | No SM unidentified species |
| 16 | $NaN_3$ Sodium azide | 1.0 | 7.0 | Water + 10% MeCN | SM | SM | N/A | Mixture of SM and 15 (4:6) |
| 17 | $NaN_3$ Sodium azide | 1.0 | 9.0 | Water + 10% MeCN | SM | SM | N/A | Mixture of SM and 15 (1:9) |

-continued

Table of Results
(Experimental Conditions: T = 50° C.; 1.0 mg 12/mL solvent).

| Entry | Nucleophile | Concn/M | pH | Solvent | t = 0.15 h | t = 0.5 h | t = 1 h | t = 18 h |
|---|---|---|---|---|---|---|---|---|
| 18 | EtNO$_2$ Nitroethane | 1.0 | 7.0 | Water + 10% MeCN | 40% SM + 50% and 10% of unidentified species | 40% SM + 50% and 10% of unidentified species | N/A | 30% SM + 55% and 15% of unidentified species |
| 19 | EtNO$_2$ Nitroethane | 1.0 | 9.0 | Water + 10% MeCN | 40% SM + 5% and 55% of unidentified species | 40% SM + 5% and 55% of unidentified species | N/A | 40% SM + 5% and 55% of unidentified species |
| 20 | CH$_2$(CN)$_2$ Malononitrile | 1.0 | 7.0 | Water + 10% MeCN | 35% SM + 65% of unidentified species | 25% SM + 75% of unidentified species | N/A | 20% SM + 80% of unidentified species |
| 21 | CH$_2$(CN)$_2$ Malononitrile | 1.0 | 9.0 | Water + 10% MeCN | 5% SM + 90% and 5% of unidentified species | 5% SM + 90% and 5% of unidentified species | N/A | 5% SM + 90% and 5% of unidentified species |
| 22 |  Morpholine | 1.0 | 9.0 | Water + 10% MeCN | N/A | N/A | 25% SM + 40% of (15) + 35% of unidentified species | No SM + 40% of (15) + 60% of unidentified species |
| 23 | Diethylamine | 1.0 | 9.0 | Water + 10% MeCN | N/A | N/A | 90% SM + 10% of (15) | 20% SM + 50% of (15) + 30% of unidentified species |
| 24 | 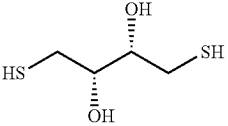 Cleland's reagent (dithiothreitol) | 1.0 | 9.0 | Water + 10% MeCN | N/A | N/A | 5% SM + 95% of unidentified species | No SM + unidentified species |
| 25 | 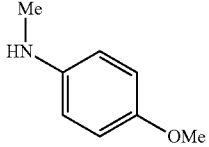 4-Methoxy-N-methylaniline | 1.0 | 8.3 | Water/MeCN (1:2) | N/A | N/A | 95% SM + 5% of unidentified species | 95% SM + 5% of unidentified species |
| 26 | 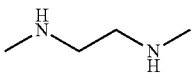 N,N'-Dimethylene diamine | 1.0 | 9.0 | Water + 10% MeCN | N/A | N/A | 5% SM + 20% of (15) + 75% of unidentified species | No SM + 20% of (15) + 80% of unidentified species |
| 27 | 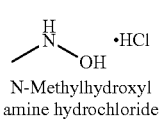 N-Methylhydroxyl amine hydrochloride | 1.0 | 9.0 | Water + 10% MeCN | N/A | N/A | 16% Product (13) + 10% of (15) + 74% of unidentified species | 10% of (15) + 90% of unidentified species |

Table of Results
(Experimental Conditions: T = 50° C.; 1.0 mg 12/mL solvent).

| Entry | Nucleophile | Concn/M | pH | Solvent | t = 0.15 h | t = 0.5 h | t = 1 h | t = 18 h |
|---|---|---|---|---|---|---|---|---|
| 28 | 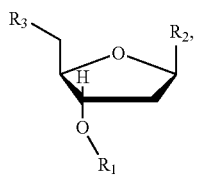<br>N,N'-dimethyl-cis-cyclohexane-1,2-diamine | 1.0 | 9.0 | Water/MeCN (2:1) | N/A | N/A | 60% SM + 35% of (15) + 5% of unidentified species | 30% SM + 50% of (15) + 20% of unidentified species |

The 3'-O-Cyanoethyl group could be cleaved in each of the following buffers in solution or on Biochips: (1) 6M Dimethylamine (DMA), pH=10.4, pH was adjust by adding NaOH, 55-60° C., 10 minutes; (2) 2. 2.5M MeNHOH, pH=8, pH was adjust by adding NaOH, 55-60° C., 10 mins; (3) 200 mM THPP, 0.2 M Tris, pH=9.5, 1.5 M NaCl, 55-60° C., 10 mins; or (4) 200 mM THPP, 1 M K$_2$HPO$_4$, 1M KCl, pH=9.5, 55-60° C., 5 mins. K$_4$PPi and F$^-$ also showed an improved effect for cleavage efficiency; however, the reagents resulted in damage on the biochip surface. See FIGS. 2 and 3. The increase of THPP concentration (FIG. 4), cleavage time (FIG. 5) and higher pH (no more than 10; FIG. 6) resulted in higher cleavage efficiency. Other reagents tested for 3'-O-Cyanoethyl-dNTP cleavage on biochips, as shown in FIG. 7, all showed very poor efficiency.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A nucleoside analogue of the following formula:

wherein
R$_1$ is a reversible blocking group selected from the group consisting of cyanoethenyl, allenyl, formaldehyde oximyl, acrylaldehyde oximyl, propionaldehyde oximyl, cyanoethenaldehyde oximyl, cis-cyanoethenyl, trans-cyanoethenyl, cis-cyanofluoroethenyl, trans-cyanofluoroethenyl, biscyanoethenyl, bisfluoroethenyl, cis-propenyl, trans-propenyl, nitroethenyl, acetoethenyl, methylcarbonoethenyl, amidoethenyl, methylsulfonoethenyl, methylsulfonoethyl, formimidate, formhydroxymate, vinyloethenyl, ethylenoethenyl, cyanoethylenyl, nitroethylenyl, amidoethylenyl,

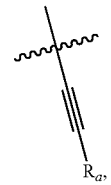

wherein R$_a$ is hydrogen, cyano, halogen, nitro, alkoxy, substituted or unsubstituted amino, substituted or unsubstituted alkyl, substituted or unsubstituted alkenyl, or substituted or unsubstituted alkynyl; and R$_b$ is hydrogen, substituted or unsubstituted alkyl, or substituted or unsubstituted alkoxy; and wherein R$_a$ is hydrogen, cyano, halogen, nitro, alkoxy, substituted or unsubstituted amino, substituted or unsubstituted sulfonyl, substituted or unsubstituted alkyl, substituted or unsubstituted alkenyl, substituted or unsubstituted alkynyl, and substituted or unsubstituted carbonyl;

R$_2$ comprises a nucleobase; and

R$_3$ is a cleavable linking moiety comprising at least three phosphates, or analogues thereof.

2. The nucleoside analogue of claim 1, wherein R$_3$ comprises a 5'-O-1-thio triphosphate.

3. The nucleoside analogue of claim 1, wherein the nucleoside analogue has the formula of Formula VIII:

Formula VIII

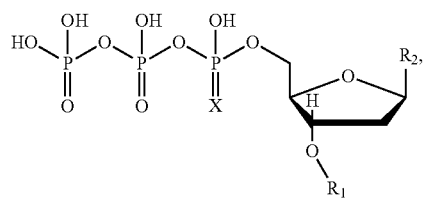

wherein X is O or S and the nucleoside analogue is a substrate for a DNA polymerase; or

73 wherein the nucleoside analogue has the following formula:

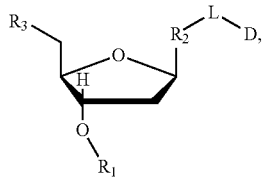

wherein
R₂ consists of the nucleobase;
L is a linker; and
D is a detectable fluorescent label; or

74 wherein the nucleoside analogue has the following formula:

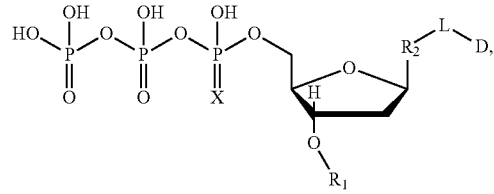

wherein
X is selected from the group consisting of O and S; or
wherein the nucleoside analogue comprises the following formula:

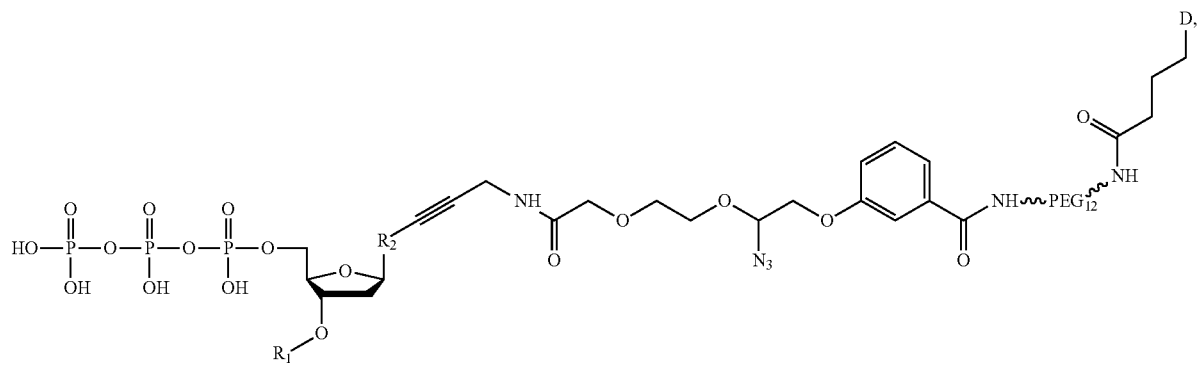

wherein R₂ is the nucleobase and D comprises a rhodamine dye or a derivative thereof; or
wherein the nucleoside analogue comprises the following formula:

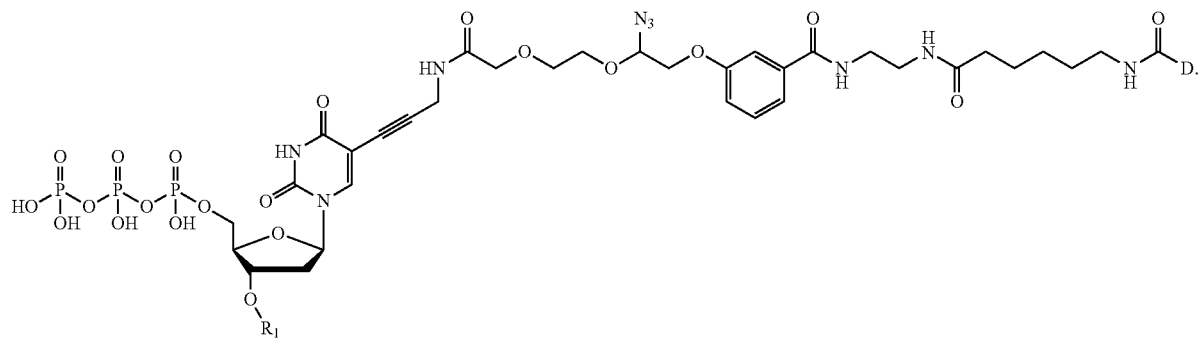

4. A nucleoside analogue of Formula VI:

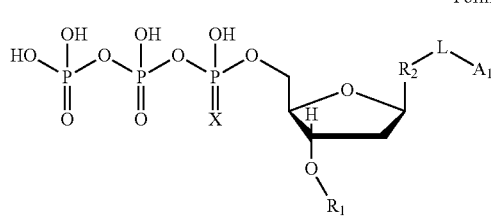

Formula VI wherein
- R₁ is a reversible blocking group selected from the group consisting of cyanoethenyl, allenyl, formaldehyde oximyl, acrylaldehyde oximyl, propionaldehyde oximyl, and cyanoethenaldehyde oximyl;
- R₂ is a nucleobase;
- L is a linker;
- A₁ comprises an affinity tag;
- X is selected from the group consisting of O and S; and
- the nucleoside analogue is a substrate for a DNA polymerase.

5. The nucleoside analogue of claim 4, wherein L is a cleavable linker.

6. The nucleoside analogue of claim 5, wherein R₁ and L can be cleaved from the nucleoside analogue under the same conditions.

7. The nucleoside analogue of claim 4, wherein A₁ comprises a nitrilotriacetic acid (NTA) affinity tag, a peptide affinity tag comprising at least six contiguous histidine amino acids, an affinity tag selected from the group consisting of biotin, a small molecule antigen, and a peptide.

8. The nucleoside analogue of claim 7, wherein the small molecule antigen is selected from the group consisting of a fluorophore, an amphetamine, a barbituate, a benzodiazepine, a cocaine metabolite, a cannabinoid, a cannabinoid metabolites, tetrahydrocannabinol, methadone, an opiate, propoxyphene, phencyclidine, digoxigenin, and DNP.

9. The nucleoside analogue of claim 7, wherein the peptide is selected from the group consisting of a His tag, a Myc tag, a Flag tag, an HA tag, a V5 tag, an AviTag, a calmodulin tag, an E tag, an S tag, an SBP tag, a Softag, a Strep tag, a TC tag, a VSV tag, an Xpress tag, glutathione, an isopeptag, and a SpyTag.

10. The nucleoside analogue of claim 4, wherein the nucleoside analogue comprises the following formula:

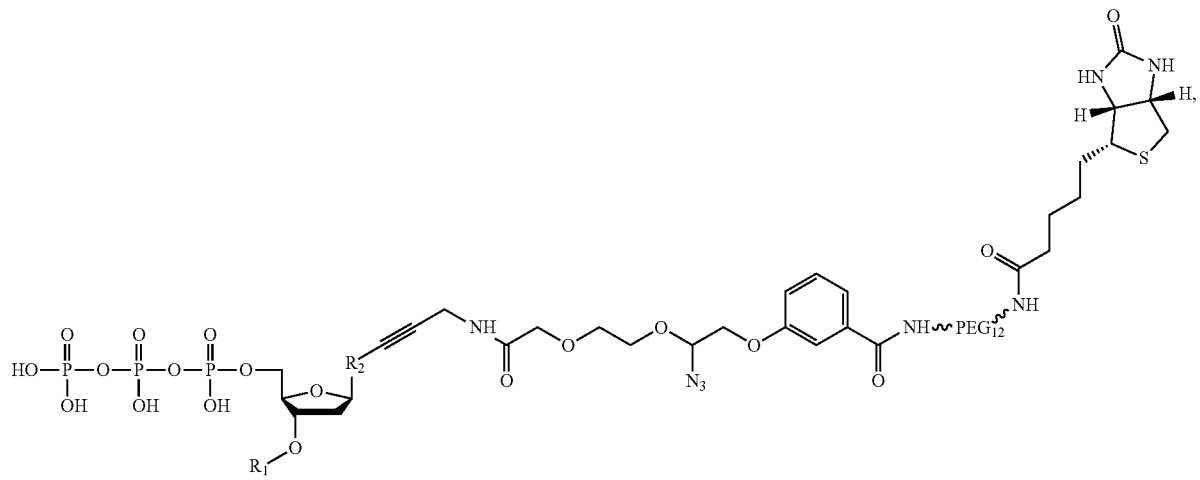

wherein R₂ is the nucleobase.

11. The nucleoside analogue of claim 10, wherein the nucleobase is selected from the group consisting of a 7-substituted 7-deaza adenine analogue, a 7 substituted 7-deaza guanine analogue, a 5-substituted thymine, and a 5-substituted cytosine.

12. A composition comprising a nucleoside analogue of the following formula:

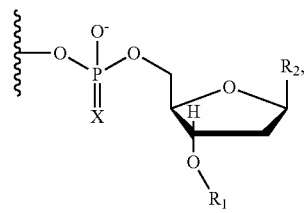

wherein
- R₁ is a reversible blocking group selected from the group consisting of cyanoethenyl, allenyl, formaldehyde oximyl, acrylaldehyde oximyl, propionaldehyde oximyl, and cyanoethenaldehyde oximyl;

X is selected from the group consisting of O and S; and $R_2$ comprises a nucleobase, and optionally a linker and a detectable label or affinity agent, wherein the nucleoside analogue is covalently linked via the 5' phosphate or thiophosphate to an oligonucleotide.

13. The composition of claim 12, wherein $R_2$ comprises a nucleobase, a linker, and a detectable label or affinity agent.

14. A composition comprising
i) a nucleoside analogue of the following formula:

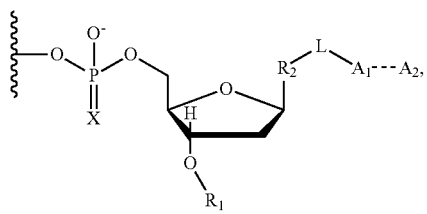

or
ii) a nucleoside analogue of Formula IX:

Formula IX

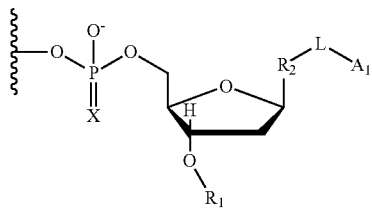

wherein
$R_1$ is a reversible blocking group selected from the group consisting of cyanoethenyl, allenyl, formaldehyde oximyl, acrylaldehyde oximyl, propionaldehyde oximyl, and cyanoethenaldehyde oximyl;

X is selected from the group consisting of O and S;

$R_2$ is a nucleobase;

L is a linker;

$A_1$ comprises an affinity tag; and $A_2$ comprises a detectably labeled affinity agent that forms a specific and non-covalent complex with $A_1$, wherein the nucleoside analogue is covalently linked via the 5' phosphate or thiophosphate to an oligonucleotide.

15. The composition of claim 14, wherein $A_1$ comprises a fluorescent dye selected from the group consisting of a fluorone dye, a rhodamine dye, a cyanine dye, a coumarin dye, a phycoerythrin, and an allophycocyanine.

16. A method of sequencing comprising:
i) providing a reaction mixture comprising template nucleic acid, a primer, a polymerase, and a first nucleoside analogue of claim 4;
ii) extending the primer by incorporating the first nucleoside analogue with the polymerase;
iii) contacting the incorporated first nucleoside analogue with a detectably labeled affinity agent that forms a specific and non-covalent complex with $A_1$ of the incorporated first nucleoside analogue, thereby specifically labeling the incorporated first nucleoside analogue; and
iv) detecting the specifically labeled incorporated first nucleoside analogue.

17. A nucleoside analogue of the following formula:

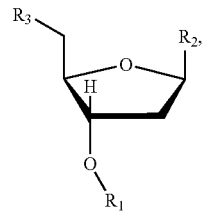

wherein:
$R_1$ is

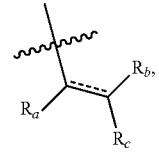

wherein $R_a$, $R_b$, and $R_c$ are each individually selected from the group consisting of hydrogen, cyano, halogen, nitro, alkoxy, substituted or unsubstituted amino, substituted or unsubstituted sulfonyl, substituted or unsubstituted alkyl, substituted or unsubstituted alkenyl, substituted or unsubstituted alkynyl, and substituted or unsubstituted carbonyl; and --- is a double bond;

$R_2$ comprises a nucleobase; and $R_3$ is a cleavable linking moiety comprising at least three phosphates, or analogues thereof.

18. The nucleoside analogue of claim 1, wherein $R_1$ is cis-cyanoethenyl or trans-cyanoethenyl.

* * * * *

UNITED STATES PATENT AND TRADEMARK OFFICE
CERTIFICATE OF CORRECTION

Page 1 of 2

PATENT NO. : 10,988,501 B2
APPLICATION NO. : 16/094845
DATED : April 27, 2021
INVENTOR(S) : Li et al.

It is certified that error appears in the above-identified patent and that said Letters Patent is hereby corrected as shown below:

On the Title Page

Column 1, Item (73), Assignee:
Delete "MGI Tech Co., Ltd.; BGI Shenzhen"
Insert -- MGI Tech Co., Ltd., (CN); BGI Shenzhen, (CN) --

In the Claims

In Column 72, Line 26, Claim 1:
Delete "alkenyl;"
Insert -- alkynyl; --

In Column 74, Line 18, Claim 3:
Delete "0"
Insert -- O --

In Column 75, Line 8, Claim 4, after:

"
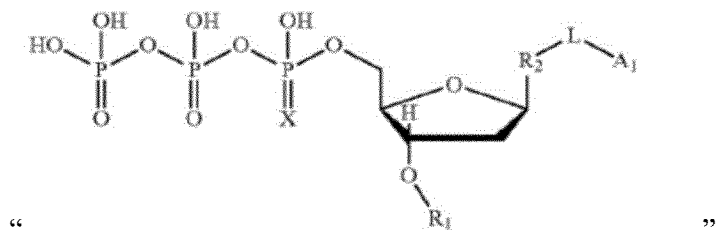
"

Insert -- , --

Signed and Sealed this
Thirteenth Day of September, 2022

Katherine Kelly Vidal
*Director of the United States Patent and Trademark Office*

In Column 77, Line 30, Claim 14, after:
" 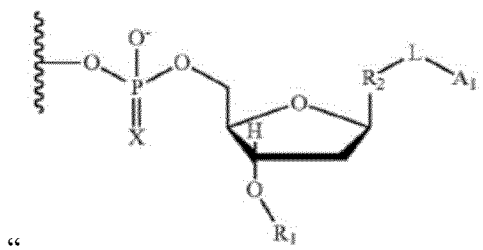 "
Insert -- ; --